United States Patent
Roy et al.

(10) Patent No.: US 11,753,624 B2
(45) Date of Patent: Sep. 12, 2023

(54) METHODS FOR GENERATING FUNCTIONAL THERAPEUTIC B CELLS EX-VIVO

(71) Applicant: Georgia Tech Research Corporation, Atlanta, GA (US)

(72) Inventors: Krishnendu Roy, Atlanta, GA (US); Kyung-Ho Roh, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1315 days.

(21) Appl. No.: 15/766,657

(22) PCT Filed: Oct. 6, 2016

(86) PCT No.: PCT/US2016/055688
§ 371 (c)(1),
(2) Date: Apr. 6, 2018

(87) PCT Pub. No.: WO2017/062578
PCT Pub. Date: Apr. 13, 2017

(65) Prior Publication Data
US 2019/0249141 A1    Aug. 15, 2019

Related U.S. Application Data

(60) Provisional application No. 62/393,698, filed on Sep. 13, 2016, provisional application No. 62/237,799, filed on Oct. 6, 2015.

(51) Int. Cl.
*G01N 33/53* (2006.01)
*C12N 5/0781* (2010.01)
*A61K 39/00* (2006.01)

(52) U.S. Cl.
CPC ............ *C12N 5/0635* (2013.01); *A61K 39/00* (2013.01); *A61K 2039/5158* (2013.01); *A61K 2039/575* (2013.01); *C12N 2501/231* (2013.01); *C12N 2501/2302* (2013.01); *C12N 2501/2304* (2013.01); *C12N 2501/2305* (2013.01); *C12N 2501/2321* (2013.01); *C12N 2501/25* (2013.01); *C12N 2501/52* (2013.01); *C12N 2537/00* (2013.01)

(58) Field of Classification Search
None
See application file for complete search history.

(56) References Cited

U.S. PATENT DOCUMENTS

| | | | | |
|---|---|---|---|---|
| 8,669,105 B2 * | 3/2014 | Sukumar | ................ | C07K 16/44 435/375 |
| 2006/0246477 A1 | 11/2006 | Hermans et al. | | |
| 2010/0184148 A1 | 7/2010 | Sukumar et al. | | |

OTHER PUBLICATIONS

Wan et al. The Journal of Immunology, vol. 190, pp. 4661-4675 (Year: 2009).*
Wu et al (Virology Journal, 2010, vol. 7, No. 370, pp. 1-7). (Year: 2010).*
Purwada, et al., "Ex vivo Engineered Immune Organoids for Controlled Germinal Center Reactions," Biomaterials, 2015 vol. 63, pp. 24-34.
Guichard, et al., "Rationally-Designed Multivalent Architectures for Mimicking Homotrimers of CD40L, a Member of the TNF Superfamily," Peptides for Youth: The Proceedings of the 20th American Peptide Symposium 2009, pp. 354-357.
Klein, et al., "Transcriptional Analysis of the B Cell Germinal Center Reaction," PNAS Mar. 4, 2003, vol. 100, No. 5, pp. 2639-2644.
Lipman, et al., "Monoclonal Versus Polyclonal Antibodies: Distinguishing Characteristics, Applications, and Information Resources,".
International Search Report and Written Opinion from PCT application No. PCT/US2016/55688 dated Feb. 23, 2017 (17 pages).
International Preliminary Report on Patentability from PCT application No. PCT/US2016/55688 dated Apr. 19, 2018 (12 pages).

* cited by examiner

*Primary Examiner* — Celine X Qian
(74) *Attorney, Agent, or Firm* — Troutman Pepper Hamilton Sanders LLP; Ryan A. Schneider; Chris N. Davis

(57) ABSTRACT

The various embodiments of the disclosure relate generally to processes, methods, and systems for generating functional B cells ex vivo. It is particularly useful for ex vivo generation of antigen-specific germinal-center (GC) like B cells that are capable of efficient B cell expansion, immunoglobulin (Ig) class switching/class switching recombination (CSR), expression of germinal B cell phenotypes, antibody secretion, and somatic hypermutation (SHM) and resulting affinity maturation center phenotypes.

18 Claims, 40 Drawing Sheets

Specification includes a Sequence Listing.

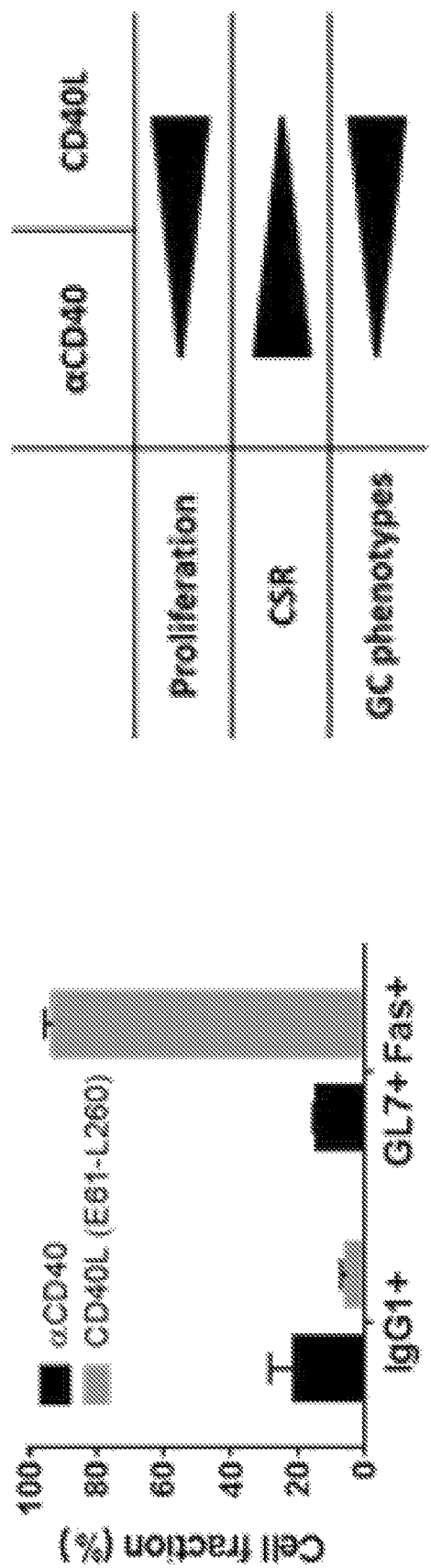
Figure 2D
Figure 2E
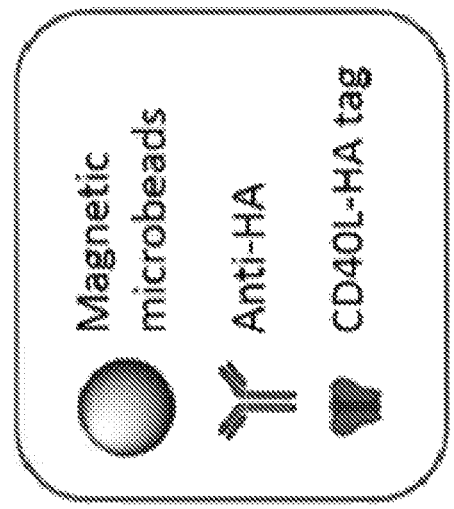
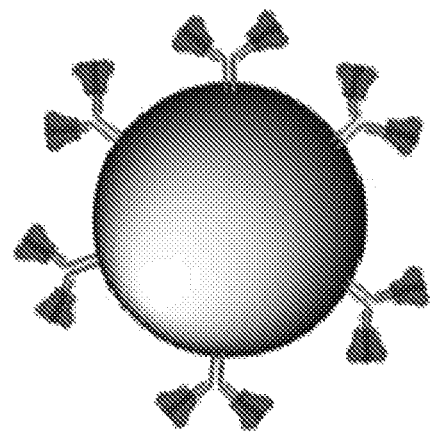
Figure 3A

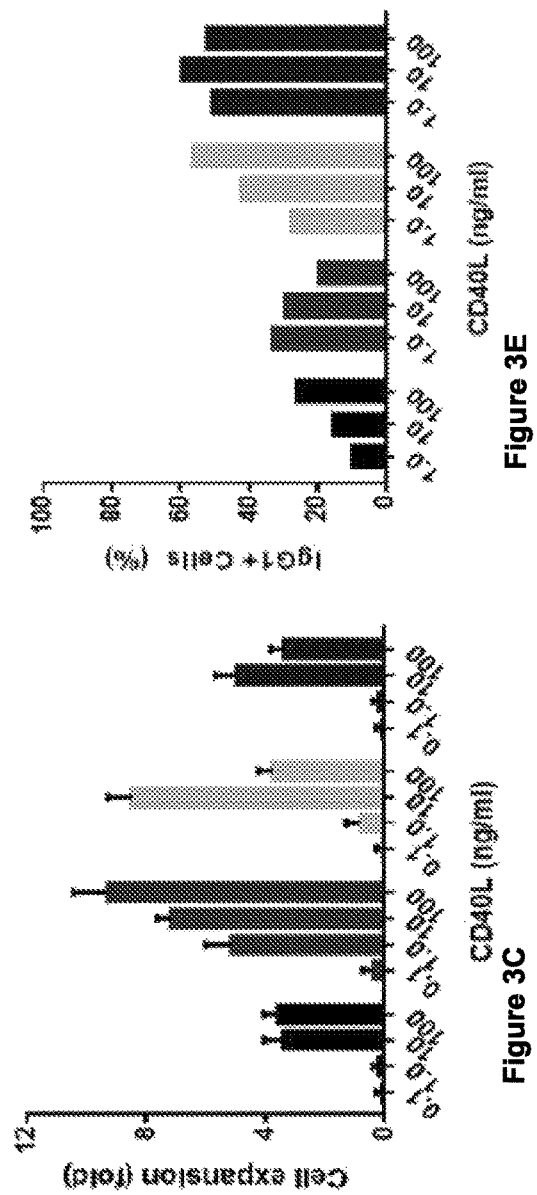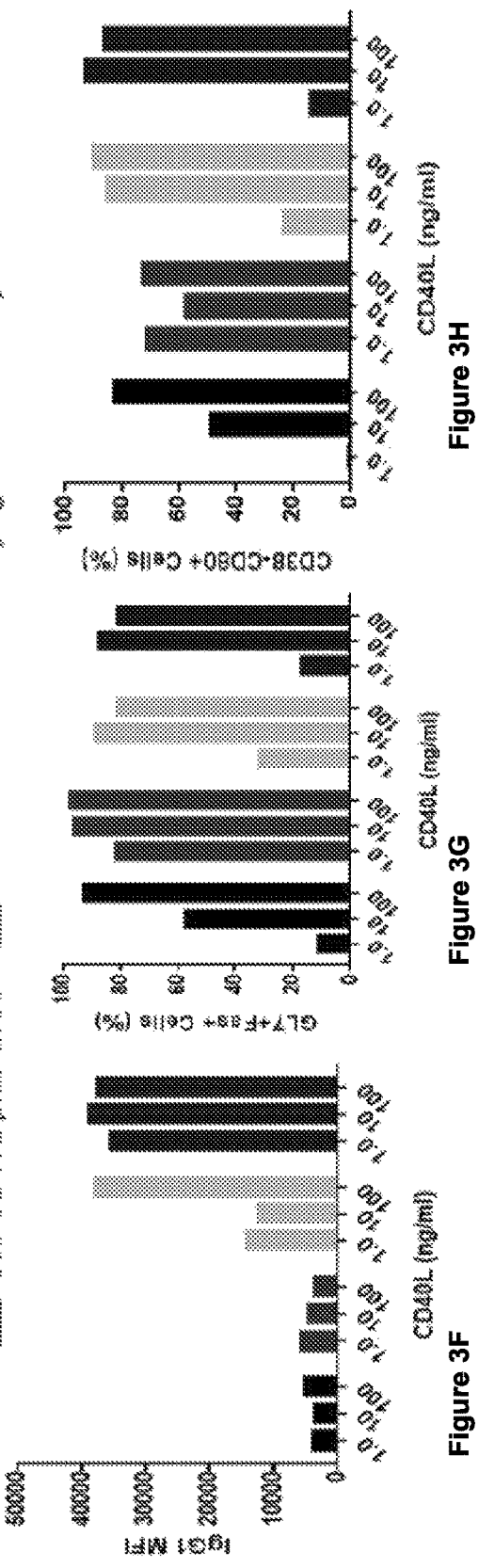
Figure 3C, Figure 3E, Figure 3F, Figure 3G, Figure 3H

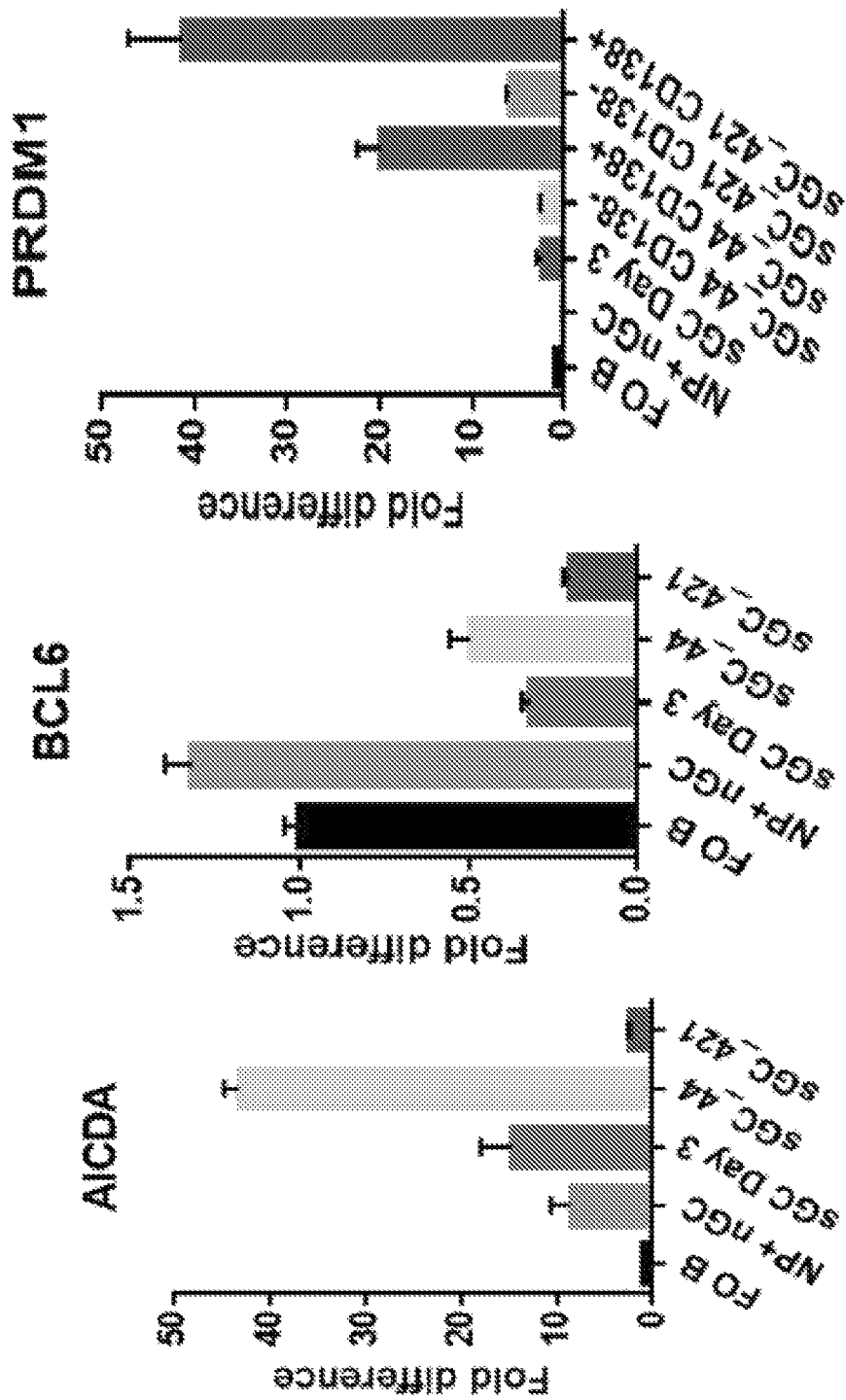

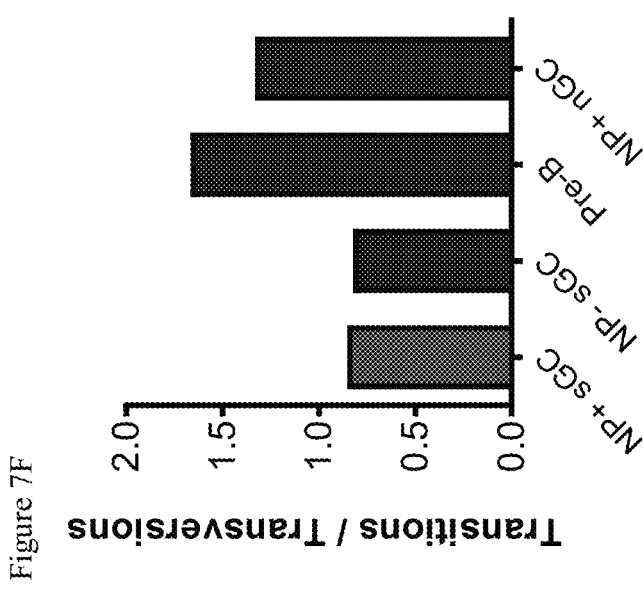
Figure 7F
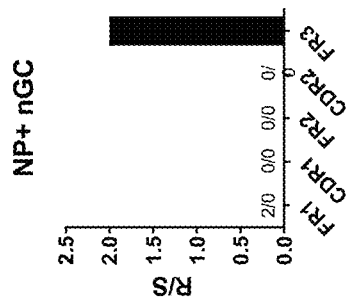
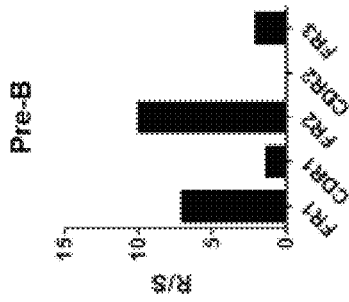
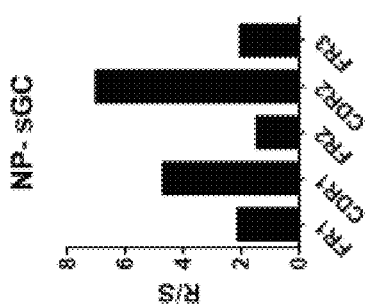
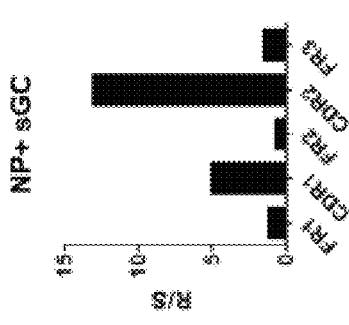
Figure 7G

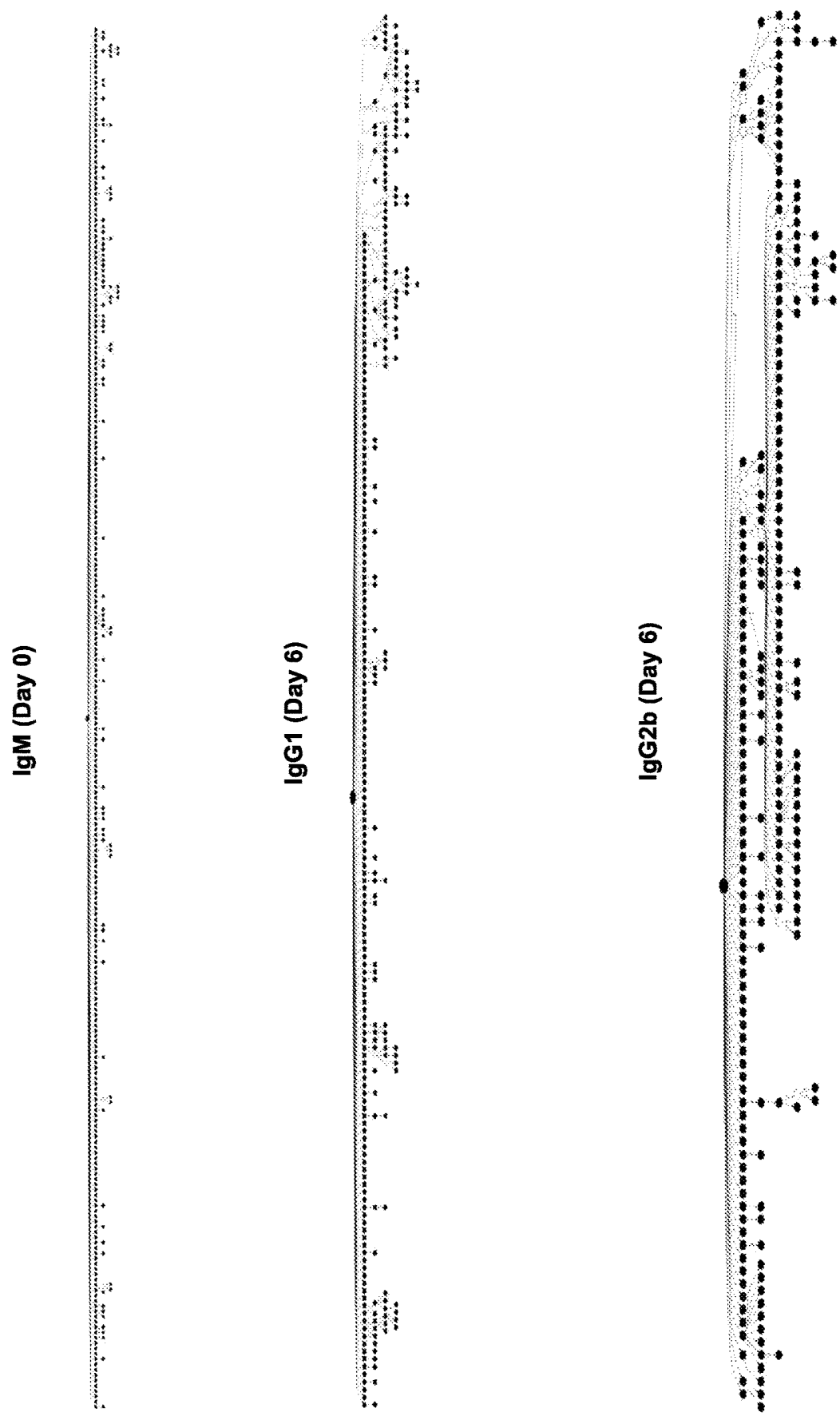

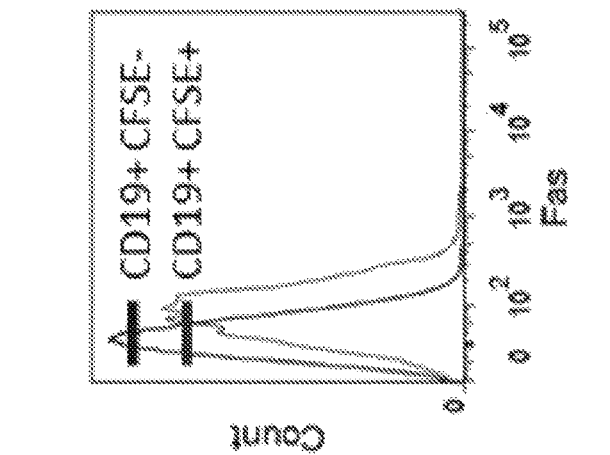
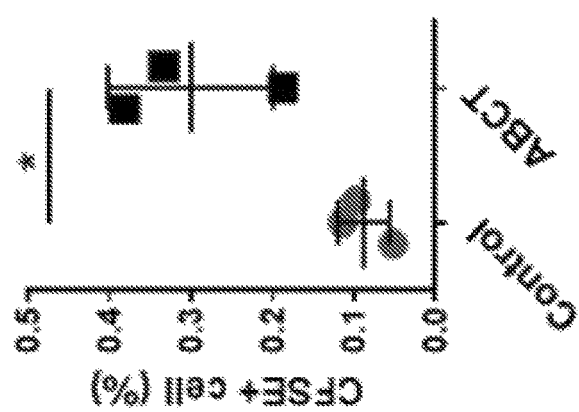
Figure 9B
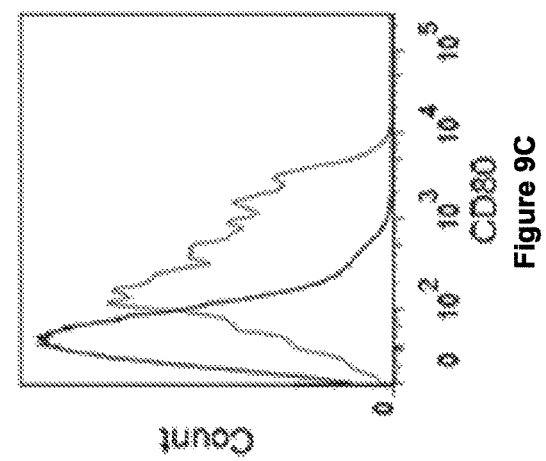
Figure 9C
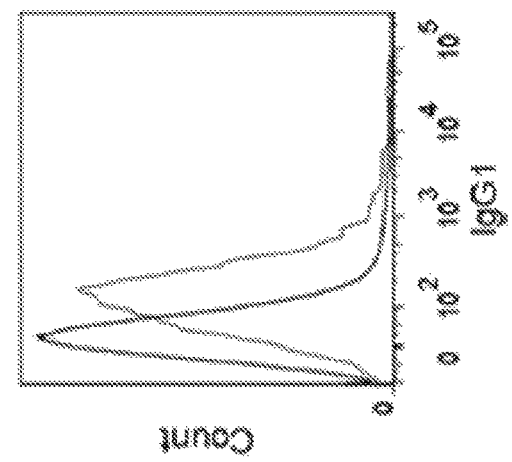

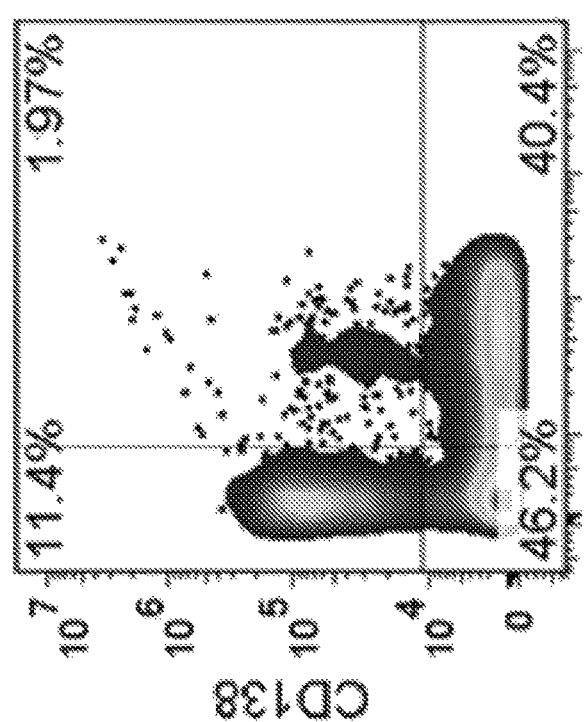
Figure 13A
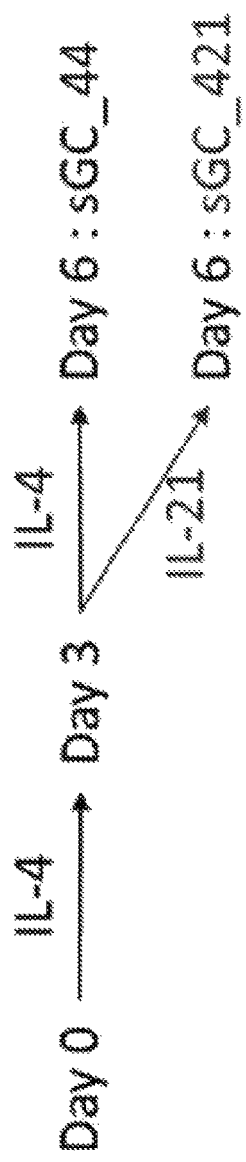
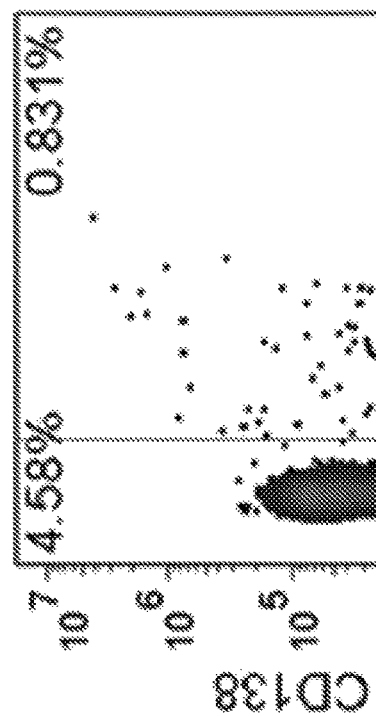
Figure 13B

Day 0
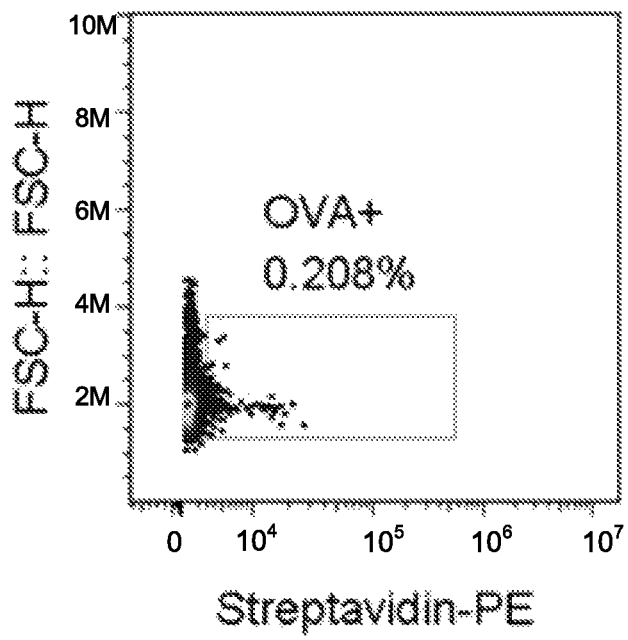
Day 6
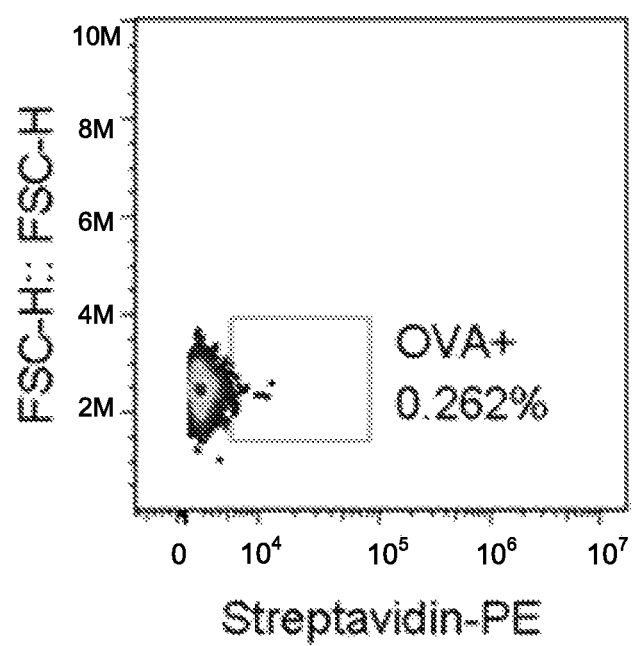
No OVA in the culture
Figure 14

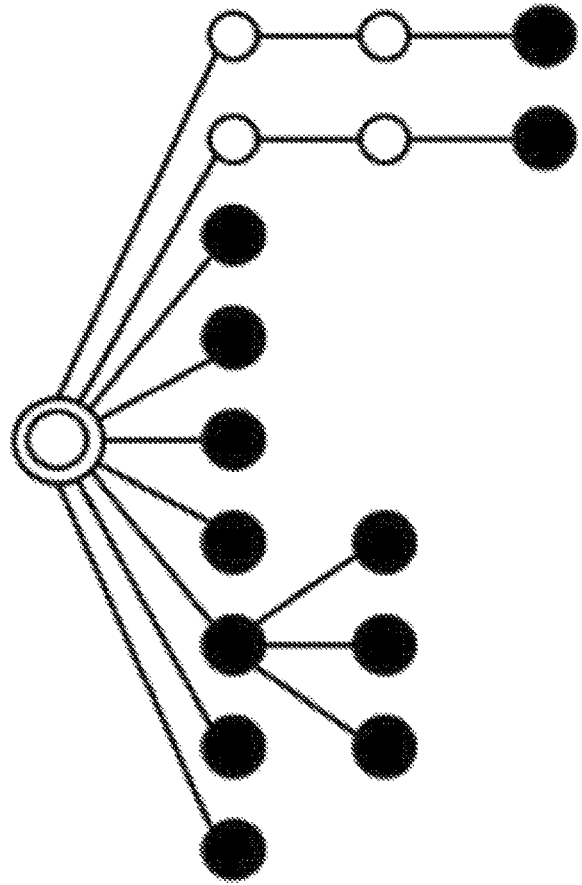
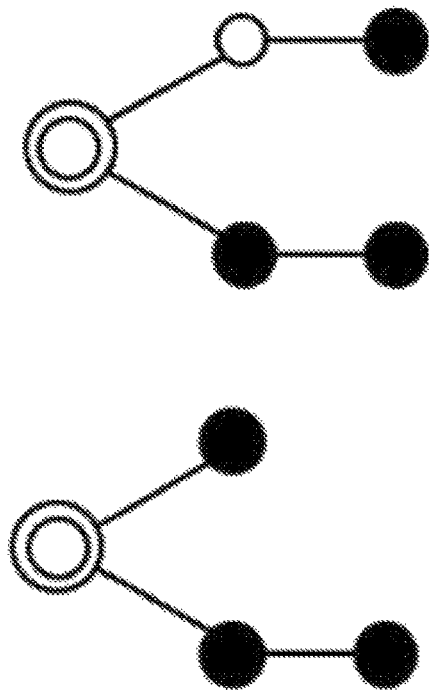
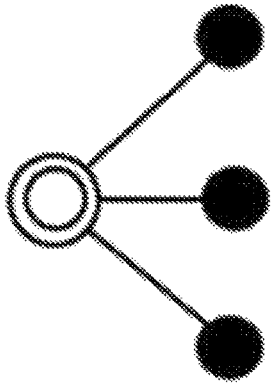
Figure 16A
Figure 16B
Figure 16C

SEQUENCE LISTING

```
<160> NUMBER OF SEQ ID NOS: 19

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Ile Ser Gln Ala Val His Ala Ala His Ala Glu Ile Asn Glu Ala Gly
1               5                   10                  15

Arg

<210> SEQ ID NO 2
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 2

Tyr Pro Tyr Asp Val Pro Asp Tyr Ala
1               5

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
gggaattcga ggtgcagctg caggagtctg g                              31

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4 aggggggctct cgcaggagac gagg                                     24

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
ggaaggtgtg cacaccgctg gac                                       23

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
cgtatcgcct ccctcgcgcc atcag                                     25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
ctatgcgcct tgccagcccg ctcag                                     25

<210> SEQ ID NO 8
<211> LENGTH: 10
<212> TYPE: DNA
<213> ORGANISM: Artificial Sequence
<220> FEATURE:
<223> OTHER INFORMATION: Synthetic

<400> SEQUENCE: 8
```
acgagtgcgt          10

<210> SEQ ID NO 9
<211> LENGTH: 10
<212> TYPE: DNA
<213> ORGANISM: Artificial Sequence
<220> FEATURE:
<223> OTHER INFORMATION: Synthetic

<400> SEQUENCE: 9
acgctcgaca          10

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10 aggggaaga catttgggaa ggac          24

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
gctcagggaa atagcccttg ac          22

<210> SEQ ID NO 12
<211> LENGTH: 67
<212> TYPE: DNA
<213> ORGANISM: Artificial Sequence
<220> FEATURE:
<223> OTHER INFORMATION: Synthetic

<400> SEQUENCE: 12
cgtatccctc cctcgcgcca tcagacacga gtgcgtggga attcgaggtg cagctgcagg          60
agtctgg          67

<210> SEQ ID NO 13
<211> LENGTH: 68
<212> TYPE: DNA
<213> ORGANISM: Artificial Sequence
<220> FEATURE:
<223> OTHER INFORMATION: Synthetic

<400> SEQUENCE: 13
cgtatcgcct ccctcgcgcc atcagacacg ctcgacaggg aattcgaggt gcagctgcag          60
gagtctgg          68

<210> SEQ ID NO 14
<211> LENGTH: 59
<212> TYPE: DNA
<213> ORGANISM: Artificial Sequence
<220> FEATURE:
<223> OTHER INFORMATION: Synthetic

<400> SEQUENCE: 14
ctatgcgcct tgccagcccg ctcagacgag tgcgtagggg aagacattt gggaaggac          59

-continued

```
<210> SEQ ID NO 15
<211> LENGTH: 59
<212> TYPE: DNA
<213> ORGANISM: Artificial Sequence
<220> FEATURE:
<223> OTHER INFORMATION: Synthetic

<400> SEQUENCE: 15
ctatgcgcct tgccagcccg ctcagacgct cgacaagggg gaagacattt gggaaggac      59

<210> SEQ ID NO 16
<211> LENGTH: 57
<212> TYPE: DNA
<213> ORGANISM: Artificial Sequence
<220> FEATURE:
<223> OTHER INFORMATION: Synthetic

<400> SEQUENCE: 16
ctatgcgcct tgccagcccg ctcagacgag tgcgtgctca gggaaatagc ccttgac        57

<210> SEQ ID NO 17
<211> LENGTH: 57
<212> TYPE: DNA
<213> ORGANISM: Artificial Sequence
<220> FEATURE:
<223> OTHER INFORMATION: Synthetic

<400> SEQUENCE: 17
ctatgcgcct tgccagcccg ctcagacgct cgacagctca gggaaatagc ccttgac        57

<210> SEQ ID NO 18
<211> LENGTH: 189
<212> TYPE: PRT
<213> ORGANISM: Artificial Sequence
<220> FEATURE:
<223> OTHER INFORMATION: Synthetic

<400> SEQUENCE: 18

Ile Glu Lys Lys Ile Glu Ala Ile Glu Lys Lys Ile Glu Ala Ile Glu
1               5                   10                  15

Lys Lys Ile Glu Ala Ile Glu Lys Lys Ile Glu Ala Gly Gly Gly Ser
            20                  25                  30

Gly Gly Gly Ser Gly Gly Gly Ser Met Gln Arg Gly Asp Glu Asp Pro
        35                  40                  45

Gln Ile Ala Ala His Val Val Ser Glu Ala Asn Ser Asn Ala Ala Ser
    50                  55                  60

Val Leu Gln Trp Ala Lys Lys Gly Tyr Tyr Thr Met Lys Ser Asn Leu
65                  70                  75                  80

Val Met Leu Glu Asn Gly Lys Gln Leu Thr Val Lys Arg Glu Gly Leu
                85                  90                  95

Tyr Tyr Val Tyr Thr Gln Val Thr Phe Cys Ser Asn Arg Glu Pro Ser
            100                 105                 110

Ser Gln Arg Pro Phe Ile Val Gly Leu Trp Leu Lys Pro Ser Ser Gly
        115                 120                 125

Ser Glu Arg Ile Leu Leu Lys Ala Ala Asn Thr His Ser Ser Ser Gln
    130                 135                 140

Leu Cys Glu Gln Gln Ser Val His Leu Gly Gly Val Phe Glu Leu Gln
145                 150                 155                 160

Ala Gly Ala Ser Val Phe Val Asn Val Thr Glu Ala Ser Gln Val Ile
                165                 170                 175

His Arg Val Gly Phe Ser Ser Phe Gly Leu Leu Lys Leu
```

```
                180             185

<210> SEQ ID NO 19
<211> LENGTH: 198
<212> TYPE: PRT
<213> ORGANISM: Artificial Sequence
<220> FEATURE:
<223> OTHER INFORMATION: Synthetic

<400> SEQUENCE: 19

Tyr Pro Tyr Asp Val Pro Asp Tyr Ala Ile Glu Lys Lys Ile Glu Ala
1               5                   10                  15

Ile Glu Lys Lys Ile Glu Ala Ile Glu Lys Lys Ile Glu Ala Ile Glu
            20                  25                  30

Lys Lys Ile Glu Ala Gly Gly Ser Gly Gly Gly Ser Gly Gly Gly
        35                  40                  45

Ser Met Gln Arg Gly Asp Glu Asp Pro Gln Ile Ala Ala His Val Val
65          50              55                  60

Ser Glu Ala Asn Ser Asn Ala Ala Ser Val Leu Gln Trp Ala Lys Lys
65                  70                  75                  80

Gly Tyr Tyr Thr Met Lys Ser Asn Leu Val Met Leu Glu Asn Gly Lys
                85                  90                  95

Gln Leu Thr Val Lys Arg Glu Gly Leu Tyr Tyr Val Tyr Thr Gln Val
                100                 105                 110

Thr Phe Cys Ser Asn Arg Glu Pro Ser Ser Gln Arg Pro Phe Ile Val
                115                 120                 125

Gly Leu Trp Leu Lys Pro Ser Ser Gly Ser Glu Arg Ile Leu Leu Lys
        130                 135                 140

Ala Ala Asn Thr His Ser Ser Ser Gln Leu Cys Glu Gln Gln Ser Val
145                 150                 155                 160

His Leu Gly Gly Val Phe Glu Leu Gln Ala Gly Ala Ser Val Phe Val
                165                 170                 175

Asn Val Thr Glu Ala Ser Gln Val Ile His Arg Val Gly Phe Ser Ser
                180                 185                 190

Phe Gly Leu Leu Lys Leu
            195
```

METHODS FOR GENERATING FUNCTIONAL THERAPEUTIC B CELLS EX-VIVO

CROSS-REFERENCE TO RELATED APPLICATIONS

This application is a U.S. National Stage Entry of PCT/US2016/055688, filed on Oct. 6, 2016, which claimed the benefit of U.S. Provisional Patent Application Ser. Nos. 62/393,698, filed Sep. 13, 2016, entitled "METHODS FOR GENERATING FUNCTIONAL THERAPEUTIC B CELLS EX VIVO," and 62/237,799, filed Oct. 6, 2015, entitled "METHODS FOR GENERATING FUNCTIONAL THERAPEUTIC B CELLS EX VIVO," the entire contents and substance of each of which are hereby incorporated by reference as if fully set forth below.

SEQUENCE LISTING

The instant application contains a Sequence Listing which has been submitted electronically in ASCII format and is hereby incorporated by reference in its entirety. Said ASCII copy, created on 5 Oct. 2016, is named GTRC7080pct_ST25.txt and is 7,178 bytes in size.

TECHNICAL FIELD

The various embodiments of the disclosure relate generally to processes, methods, and systems for generating functional B cells ex vivo. It is particularly useful for ex vivo generation of antigen-specific germinal-center (GC) like B cells, memory-type B cells, and plasma cells that are capable of efficient B cell expansion, immunoglobulin (Ig) class switching/class switching recombination (CSR), expression of germinal B cell, memory-type B cell, or plasma cell phenotypes, antibody secretion, and somatic hypermutation (SHM) and resulting affinity maturation center phenotypes.

BACKGROUND

B cells play a major role in the adaptive immune response by producing antigen-specific antibodies against pathogens and imparting immunological memory. For this successful generation of B cell immunity, naïve B cell populations with membrane immunoglobulin receptors (B cell receptors, BCRs) recognizing the specific antigens are selectively activated in a specialized microenvironment called the germinal center (GC) in secondary lymphatic organs such as lymph nodes and the spleen. These B cells in GC rapidly proliferate and their BCRs undergo isotype switching (class switching recombination, CSR) and somatic hypermutations (SHM) with resulting affinity maturation. Following infection or vaccination, antibody-secreting B cells and memory B cells are generated in specialized regions of lymph nodes and spleens, called germinal centers.

As a critical arm of adaptive immunity, B cells provide humoral immunity by producing antibodies towards various pathogens. In particular, the generation of memory B cells and long-lived plasma cells (LLPCs) is critical to immune memory and protection from recurring infection. Memory B cells recognize and are rapidly activated by recurring antigens to secrete antigen-specific high-affinity antibodies. LLPCs produce and maintain the protective level of these antibodies in the serum.

Memory B cells and LLPCs are typically generated inside special sub-anatomical microenvironments called germinal centers (GCs) within secondary lymphoid organs such as lymph nodes and the spleen. In these lymphoid tissues, a small fraction of naïve B cells recognize a given antigen presented by follicular dendritic cells (FDCs); they then process and present the antigen to follicular helper T ($T_{FH}$) cells. B cells forming close interactions with $T_{FH}$ cells are further activated by costimulatory signals provided by $T_{FH}$ cells, and these activated B cells proliferate rapidly, expanding populations of responding B cell clones within the GC. Mimicking this complex set of events ex vivo has proven elusive. Such ex vivo synthetic GCs (sGC) could not only provide new insights in B cell biology, but also allow generation of antigen-specific B cells for antibody production and adoptive immunotherapies.

Herein is discussed a method of biomaterials-based artificial lymph node or GC-like reactions that allow both (i) rapid expansion of B cells, and (ii) essential phenotypic differentiations including CSR and/or SHM. These reactions can be induced by either anti-CD40 antibodies or recombinant CD40L proteins, or both, as a soluble or as a surface-bound form. The surface presentation can be achieved on a three-dimensional structure, such as for example and not limitation, microbeads, and further the structure may or may not include a fluid lipid bilayer to mimic a cell membrane. Similarly, the antigens of proteins, peptides, DNAs, RNAs, lipids, glycoproteins or glycolipids can be presented as either soluble or surface-bound forms. The antigens may be presented in a multivalent form. The B cells are preferably cultured in a media supplemented with various cytokines (e.g., interleukins), growth factors (e.g., BAFF), and/or ligands for toll-like receptors (e.g., LPS, CpG). The antigen-specific B cell populations can be sorted/enriched, for example and not limitation, by fluorescence-activated cell sorting (FACS) and/or magnetic-activated cell sorting (MACS) before or after the GC reaction. The starting B cell populations can be isolated from secondary lymphoid organs such as for example and not limitation, the spleen, or peripheral blood mononuclear cells (PBMCs), or can be induced from hematopoietic stem/progenitor cells isolated from, e.g., bone marrow or cord blood. The resulting GC B cells can be used for adoptive B cell transfer immunotherapy for infectious diseases, cancer, autoimmune diseases; and for the production of human antibodies.

BRIEF SUMMARY

The various embodiments of the disclosure relate generally to processes, methods, and systems for generating functional B cells, memory-type B cells, and plasma cells ex vivo.

In one aspect, the disclosure provides a method of ex vivo generation of B cells in a synthetic germinal center comprising the steps of:

a) isolating naïve B cells from a primary source (e.g., PMBC, spleen, lymph node, stem/progenitor cell);

b) exposing the B cell to CD40L and to an antigen in the synthetic germinal center, at least one of which is presented on a three dimensional surface;

c) eliminating dead B cells and the three dimensional surface; and d) obtaining antigen-specific B cells with at least three characteristics selected from the group consisting of: efficient B cell expansion/proliferation, class switching recombination (CSR), expression of germinal center B cell or plasma cell phenotypes, antibody secretion, and somatic hypermutation (SHM) and resulting affinity maturation.

In another aspect, the disclosure provides a method of ex vivo generation of B cells in a synthetic germinal center comprising the steps of:

a) isolating naïve B cells from a primary source (e.g., PMBC, spleen, lymph node, stem/progenitor cell);

b) exposing the B cell to CD40L and to an antigen in the synthetic germinal center, at least one of which is in a soluble form;

c) eliminating dead B cells; and d) obtaining antigen-specific B cells with at least three characteristics selected from the group consisting of: efficient B cell expansion/proliferation, class switching recombination (CSR), expression of germinal center B cell or plasma cell phenotypes, antibody secretion, and somatic hypermutation (SHM) and resulting affinity maturation.

In one embodiment of any of the foregoing aspects, the three dimensional surface comprises a microbead or a microcarrier.

In a further embodiment of any of the foregoing, at least one of the CD40L and the antigen are present in multivalent form.

In yet another embodiment of any of the foregoing, step (a) further comprises sorting, classifying or purifying the naïve B cell population prior to step (b).

In one embodiment of any of the foregoing, at least one of the CD40L and the antigen is bound to the microbead or microcarrier.

In still another embodiment of any of the foregoing, at least one of the CD40L and the antigen is bound to the microbead or microcarrier.

In one embodiment of any of the foregoing, step (b) further comprises adding soluble factors to the synthetic germinal center.

In another embodiment of any of the foregoing, the soluble factors comprise cytokines, B cell growth or activation factors, and/or toll-like receptor ligands.

In a further embodiment, the cytokines comprise IL-2, IL-4, IL-5, IL-10, and/or IL-21.

In another embodiment of any of the foregoing, step (c) comprises centrifugation, fluorescence-activated cell sorting (FACS), magnetic-activated cell sorting (MACS), enzymatic degradation, various filtrations, microfluidic cell sorting, and/or size exclusion chromatography to eliminate dead cells and/or three dimensional structures.

In yet another embodiment of any of the foregoing, step (c) further comprises purifying antigen-specific B cells.

In a further embodiment, purifying the antigen-specific B cells comprises cell sorting, centrifugation, microfluidic cell sorting, and/or size exclusion chromatography.

In further embodiment of any of the foregoing, the disclosure provides for use of the antigen-specific B cells resulting from any of the above embodiments to treat the disease or condition related to the antigen.

In a related aspect, the disclosure provides for use of antigen-specific B cells obtained by an ex vivo production method, said method comprising the steps of:

a) isolating naïve B cells from a primary source (e.g., PMBC, spleen, lymph node, stem/progenitor cell);

b) exposing the B cell to CD40L and to an antigen in the synthetic germinal center, at least one of which is presented on a three dimensional surface;

c) eliminating dead B cells and the three dimensional surface; and d) obtaining the antigen-specific B cells.

In one embodiment, the three dimensional surface comprises a microbead or a microcarrier.

In another embodiment, at least one of the CD40L and the antigen are present in multivalent form.

In yet another embodiment, step (a) further comprises sorting, classifying or purifying the naïve B cell population prior to step (b).

In still another embodiment, at least one of the CD40L and the antigen is bound to the microbead or microcarrier.

In one embodiment of any of the foregoing, step (b) further comprises adding soluble factors to the synthetic germinal center.

In another embodiment of any of the foregoing, the soluble factors comprise cytokines, B cell growth or activation factors, and/or toll-like receptor ligands.

In a further embodiment, the cytokines comprise IL-2, IL-4, IL-5, IL-10, and/or IL-21.

In another embodiment of any of the foregoing, step (c) comprises centrifugation, fluorescence-activated cell sorting (FACS), magnetic-activated cell sorting (MACS), enzymatic degradation, various filtrations, microfluidic cell sorting, and/or size exclusion chromatography to eliminate dead cells and/or three dimensional structures.

In one embodiment of any of the foregoing, step (c) further comprises purifying antigen-specific B cells.

In a further embodiment, purifying the antigen-specific B cells comprises cell sorting, centrifugation, and/or size exclusion chromatography.

In another embodiment of any of the foregoing, the antigen-specific B cells have at least three characteristics selected from the group consisting of: efficient B cell expansion/proliferation, class switching recombination (CSR), expression of germinal center B cell or plasma cell phenotypes, antibody secretion, and somatic hypermutation (SHM) and resulting affinity maturation.

In another embodiment of any of the foregoing, the CD40L is a protein comprising the amino acid sequence of SEQ ID NO: 18.

These and other objects, features and advantages of the present invention will become more apparent upon reading the following specification in conjunction with the accompanying description, claims and drawings.

BRIEF DESCRIPTION OF THE DRAWINGS

FIG. 2a-2e. Incompetence of soluble anti-CD40 antibody and CD40L in induction of full B cell activation. (2a) Schematic of B cell activation in a germinal center (GC). (2b) Cumulative fold increase in the number of live B cells. The squares (αCD40) and circles (CD40L) are mean values of each time point and the error bars are standard deviation (s.d.) from 3 experiments. (2c) Representative sets of flow cytometry analysis for the indicated markers before (day 0) and after (day 6) of B cell cultures using soluble αCD40 or CD40L in conjunction with IL-4 and BAFF. Numbers indicate the percentages of cells in the respective quadrants. (2d) Summary of flow cytometry analysis plotted for the percentages of cells in the indicated gates on day 6 with mean±s.d. from three separate experiments. (2e) Comparison of different quality and quantity that soluble αCD40 or CD40L induce on B cells.

FIG. 3a-3h. Artificial $T_{FH}$ design for induction of full activation of B cells and development of artificial GC structure and phenotypes. (3a) Schematic representation of artificial $T_{FH}$ cell design. Surface density can be controlled simply by varying incubation concentration of CD40L molecules. (3b) Phase-contrast light microscope images of artificial GC structures. Splenic naïve B cells complexed with artificial $T_{FH}$ microbeads develop into these spheroid structures within 48 hours of culture. It is often that darker areas enriched with microbeads (artificial T cell zone) coexist with lighter artificial B cell zones. Scale bar (left) is 300 µm. Right image is an enlargement of dotted-line inset area of the left image. (3c-3h) Direct comparison of soluble CD40L and microbead-bound CD40L for activation of B cells and induction of GC reaction. For each indicated method of CD40-engagement method, the dose of CD40L was varied. (3c) B cell fold expansion plot showing mean and s.d. of the number of live cells on day 6 of culture. Data was acquired from 5 wells per group from a single experiment. (3d-3f) Flow cytometry analysis for isotype class switching recombination (CSR) of B cells on day 6 of culture for each indicated condition. Percentage of IgG1+ B cell (3e) and IgG1 MFI (3f) were calculated and plotted from the representative flow cytometry chart (3d). (3g, 3h) Differentiation into GC-like B cells on day 6 of culture for each indicated condition. Percentage of B cells possessing two typical GC B cell phenotypes, GL7+Fas+(3g) and CD38-CD80+(3h), were calculated and plotted from respective flow cytometry analysis chart (FIG. 10, 11).

FIG. 4a-4c. Transcriptional differentiation of sGC B cells. Quantitative real-time PCR analysis of AICDA (4a), BCL6 (4b), and PRDM1 (4c) transcripts in each indicated cells. FO B: Splenic follicular B cells from unimmunized C57BL/6J mice sorted by FACS (CD19+, CD43−, CD21+, CD23$^{high}$, CD138−), NP+ nGC: physiological (natural) GC B cells purified by FACS (NP+, CD19+, CD43−, GL7+, Fas+) from the spleen of C57BL/6J mice vaccinated with NP$_{45}$-CGG/Alum 2 weeks before, sGC Day3: total sGC B cells after initial 3-day cultures performed under IL-4, sGC_44 and sGC_21: IL-4 used in the initial 3 days of sGC cultures was either maintained (sGC_44) or switched to IL-21 (sGC_421) for the rest of the sGC cultures up to Day 6. CD138+ or CD138− of sGC_44 and sGC_421 cells were also purified by FACS, accordingly. Representative data from two independent experiments are reported as the fold differences in expression levels relative to that in follicular B cells (FO B, set as 1). Error bars represent s.d. of triplicates.

FIG. 7a-7g. Potential affinity maturation by somatic hypermutation (SHM) in sGC reaction with multimeric epitopes. (7a, 7b) Flow cytometry analysis of the B cells stained with PE-conjugated peptide-OVA (pOVA) tetramers after 6-day sGC culture. (7a) pOVA-specific B cell populations are gated and the percentages are notified. (7b) The histograms of pOVA tetramer-positive B cells were compared between the B cells cultured after initial FACS enrichment step (FACS+) in the presence (grey) or absence (black) of the unconjugated tetramer pOVA during the sGC cell cultures. (7c) Number of mutations per heavy chain sequence for the pOVA-specific B cells cultured with or without the unconjugated tetramer pOVA during the sGC cell cultures. Samples contain both IgM as well as class switched IgG sequences. The values of indicated mean±s.e.m. are 3.186±0.2637, 1.650±0.1123, 3.310±0.6896, and 8.833±0.9028, for No tetOVA_IgM, tetOVA_IgM, No tetOVA_Fwd, and tetOVA_Fwd, respectively. (7d) The ratio of total number of transitions over transversions was calculated and graphed for each sequencing dataset. The values indicated in a bar graph are 0.529, 1.069, 0.944, and 3.969 for No tetOVA_IgM, tetOVA_IgM, No tetOVA_Fwd, and tetOVA_Fwd, respectively. (7e) Number of mutations per heavy chain sequence for the NP-specific B cells or pre-B cell control. NP-specific B cells were sGC cultured with (NP+ sGC) or without (NP− sGC) the NP$_{45}$-CGG. NP-specific physiological (natural) GC B cells (NP+ nGC) were purified by FACS (NP+, CD19+, CD43−, GL7+, Fas+) from the spleen of C57BL/6J mice vaccinated with NP$_{45}$-CGG/Alum 2 weeks before. Bone-marrow-derived pre-B cells (Pre-B) were purified from unimmunized mice by FACS (B220+, CD19+, CD43−, CD24+, CD138−). The values of indicated mean±s.e.m. are 2.475±0.1524, 1.810±0.1747, 1.000±02153, and 4.75±0.4787, for NP+ sGC, NP− sGC, Pre-B, and NP+ nGC, respectively. (7f) The ratio of total number of transitions over transversions was calculated and graphed for each sequencing dataset. The values indicated in a bar graph are 2.54, 2.67, 0.917, and 2.00 for NP+ sGC, NP− sGC, Pre-B, and NP+ nGC, respectively. (7g) The ratio of replacement mutations over silent mutations (R/S) calculated for the complementarity determining regions (CDRs) and the frameworks (FRs) of each dataset. Within (7c) and (7e), statistical significance from ordinary one-way ANOVA followed by Tukey's multiple comparisons test were represented as * (p<0.05),  (p<0.01), and ** (p<0.0001).

FIG. 8. Clonal tree analysis of B1-8 B cells before and after sGC culture. Clonal trees were formulated from 598 IgM, 470 IgG1, and 338 IgG2b unique sequences isolated from either naïve B cells (Day 0) for IgM or sGC B cells (Day 6) for IgG1 and IgG2b. The IgM tree is very wide and shallow, which indicates that the detected mutations are mostly random and potentially originated from sequencing- and PCR-error. Compared to the IgM tree, IgG trees clearly demonstrate an accumulation of mutations in many sub-lineages.

FIG. 9a-9f. Fate of adoptively transferred B cells generated by sGC cell culture. (9a-9c) Flow cytometry analyses of the lymph nodes harvested from the recipient C57BL/6J mice 4 days after adoptive B cell transfer (ABCT) of sGC B cells derived from syngeneic donor mice and from the control mice without ABCT (saline injection). For ABCT, $1 \times 10^7$ sGC B cells after 6-day sGC culture loaded with CFSE were adoptively transferred via tail vein. Percentage of CFSE positive cells were gated and notified from the representative flow cytometry plots for control and ABCT mice (9a). (9b) Collection of percentages of CFSE+ cells in the pooled lymph nodes harvested from control mice (circle) and mice 4 days after ABCT (square). Each circle and square represent a mouse. * represents statistical significance ($p<0.05$) in Student's t-test. (9c) Expression levels of the indicated markers, IgG1, CD80, and Fas, on the CD19+ CFSE− (host endogenous B cells, black) and the CD19+ CFSE+(adoptively transferred donor B cells, grey) in the lymph nodes harvested from a mouse 4 days after ABCT. (9d) Immunofluorescence micrograph of a section of an inguinal lymph node harvested from a mouse 4 days after ABCT. White: CFSE; Light grey: B220 (B cells); Dark grey: CD4 (T cells); and the scale bar is 100 µm. (9e, 9f) Representative data of flow cytometry analyses of the splenocytes isolated from the recipient C57BL/6J mice 4 weeks after ABCT and from the control mice without ABCT. Approx. $1 \times 10^7$ sGC B cells derived from C56BL/6-CD45.1 mice were adoptively transferred to congenic C57BL/6J mice (CD45.2+) following non-lethal irradiation (6.5 Gy). The control mice were also non-lethally irradiated (6.5 Gy) 4 weeks before the flow cytometry. For CD19+CD45.1− (host B cells) and CD19+CD45.1+(donor B cells) populations, the relative composition of IgM+ and IgG1+ cells were enumerated. Expression levels of the other indicated markers, GL7, CD80, CD38, and Fas, on CD19+CD45.1 (host B cells, black) and CD19+CD45.1− (donor B cells, grey) populations were also compared.

FIG. 13a-13c. Effects of switching cytokines from IL-4 to IL-21 during sGC cell culture. (13a) Schematic diagram depicting two sGC culture conditions: In sGC_44 condition, IL-4 (20 ng ml$^{-1}$) is maintained for the whole period of 6-day sGC culture. In sGC_421 condition, IL-4 (20 ng ml$^{-1}$) is used for the initial 3 days, and switched to IL-21 (10 ng ml$^{-1}$) on Day 3. (13b) Flow cytometry analysis for the B cells after 6-day culture of sGC_44 (left) and sGC_421 (right). Expression levels of IgG1 and CD138 were tested and numbers indicate the percentages of cells in the respective quadrants. (13c) Cell percentages of indicated gates were plotted with mean and s.d. acquired from triplicates.

FIG. 16a-16c. Clonal tree analysis of antigen-specific sGC B cells. Representative shapes of phylogenetic trees containing the most rounds of mutations identified within pOVA-specific (16a) and NP-specific (16b) sGC B cells are depicted. (16c) Examples of majority of the calculated trees in both datasets containing less than 2 generations of mutations. Each tree node represents each clonal sequences, the line connecting each nodes represents a single mutation excluding deletions, insertions, or gaps. Double-circled nodes represent germ line sequence of shared VH-family within each tree. Empty nodes represent clones that were calculated but not detected experimentally. Filled nodes represent clones that were actually detected in sequencing experiments.

DETAILED DESCRIPTION

Figures 1A, 1B:
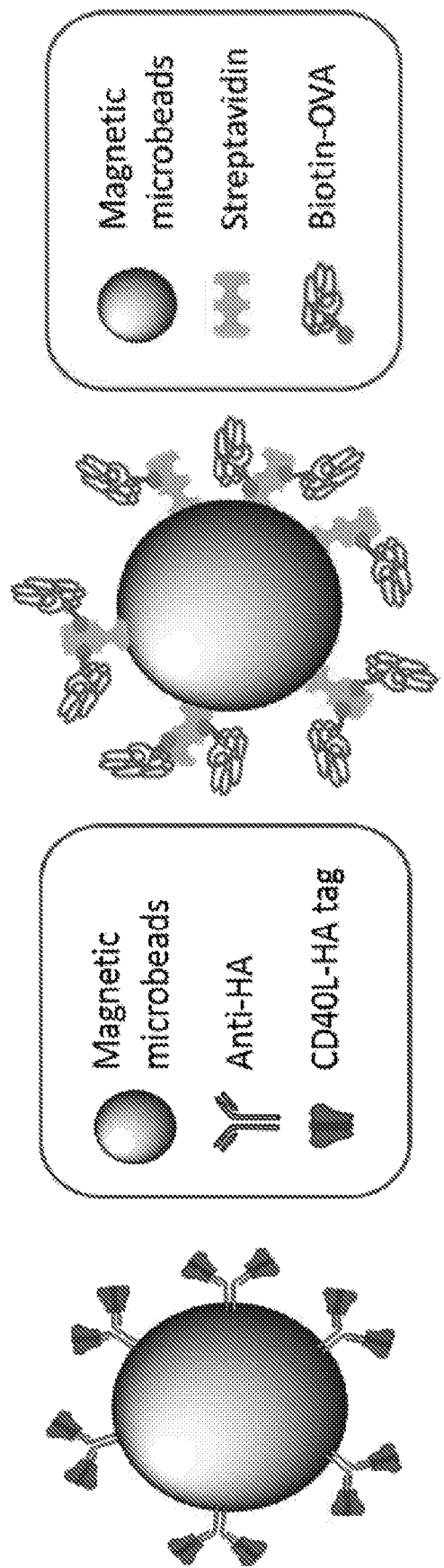
FIG. 1a-1d. Schematic of an Exemplary Embodiment of the Described Method. (1a) Diagram of a synthetic follicular T helper cell presenting CD40L (sT$_{FH}$). (1b) Diagram of a synthetic follicular dendritic cell (sFDC) presenting an antigen (sFDC). (1c) Diagram of a synthetic germinal center (sGC) according to an exemplary embodiment of the invention, containing a naïve B cell, sT$_{FH}$, and sFDC in the presence of necessary soluble factors, such as for example and not limitation, cytokines (such as IL-4 and IL-21), and B-cell activating factor (BAFF). (1d) Flowchart describing an exemplary embodiment of the described method.
Figure 1C:
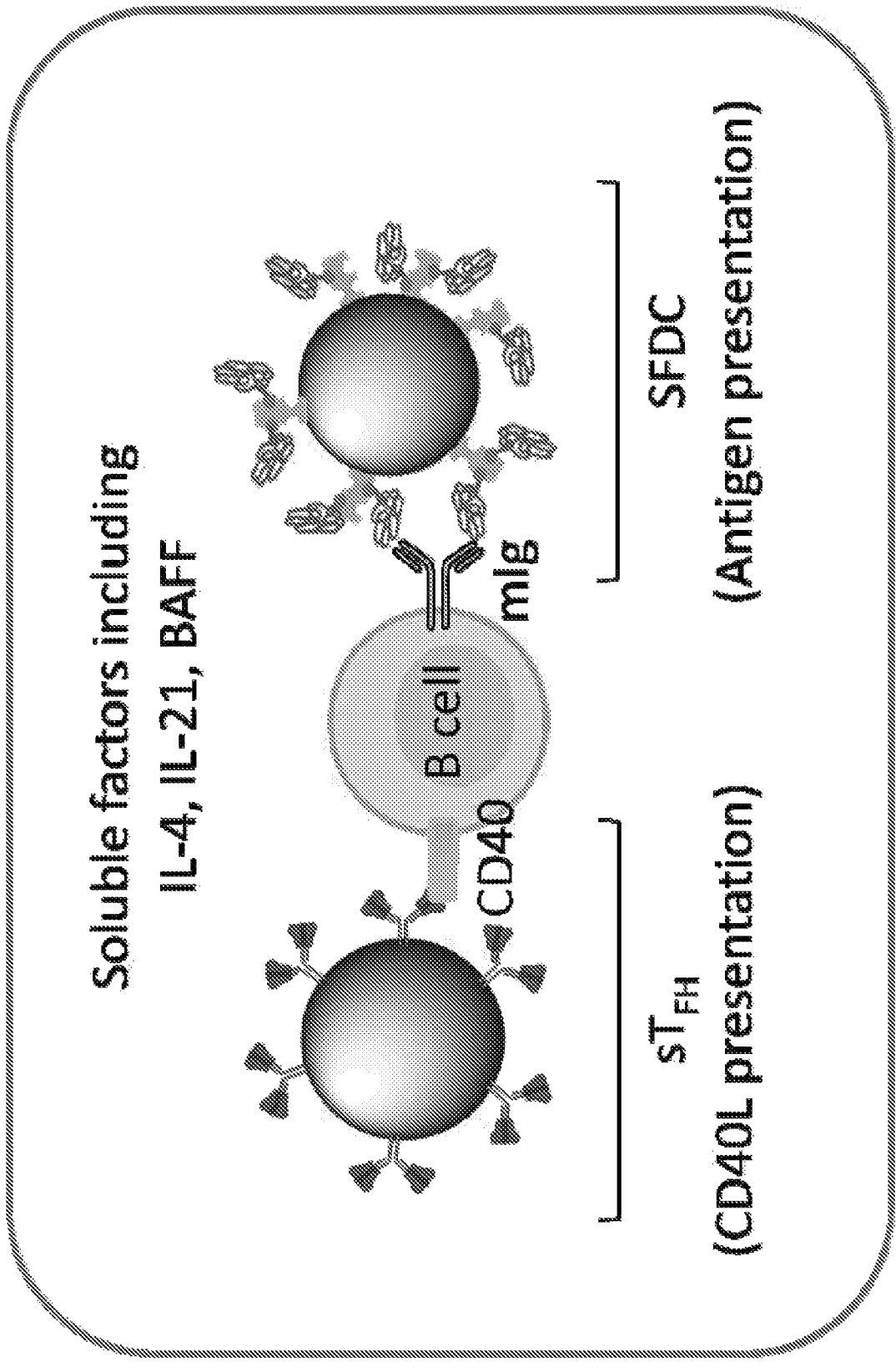
Figure 1D:
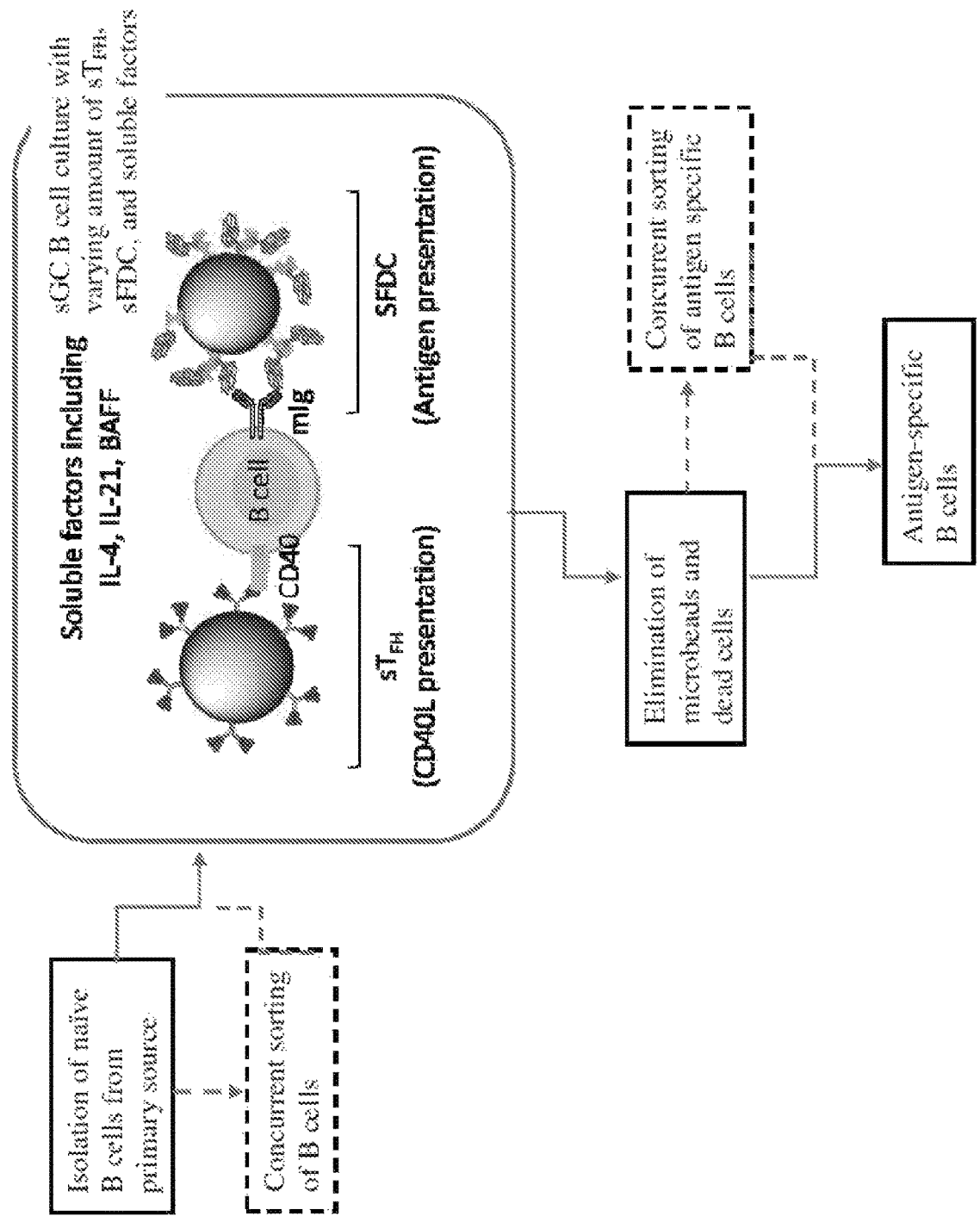

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Herein is described a fully synthetic ex vivo system that generates antigen-specific germinal-center (GC) like B cells. An exemplary version of the described synthetic germinal center (sGC) reaction was effectively induced using artificial "follicular T helper cells ($T_{FH}$)" that provided both natural CD40-CD40L ligation as well as crosslinking of CD40; and by mimicking artificial "follicular dendritic cells (FDC)" to provide efficient antigen presentation. The artificial sGC reaction resulted in efficient B cell expansion, immunoglobulin (Ig) class switching, CSR, SHM, and expression of germinal center phenotypes. Antigen presentation during sGC reaction selectively enhanced the antigen-specific B cell population and induced somatic hyper-mutations, indicating potential affinity maturation. The resulting B cell population consisted primarily of GC-like B cells (centrocytes) as well as some plasma-like B cells expressing CD138. With concurrent cell sorting, highly enriched (~100 fold) populations of antigen-specific B cells were successfully created. Adoptive transfer of these GC-like B cells into non-irradiated isogeneic or non-lethally irradiated congenic recipient mice showed successful engraftment and survival of the sGC B cells for 4 weeks. Herein it is shown that this sGC system can be successfully applied to not only splenic B cells but also B cells isolated from more therapeutically relevant sources such as peripheral blood mononuclear cells (PBMCs), thus making the described method an exciting prospect in the new era of personalized medicine and custom-immunotherapy.

It was hypothesized that the GC reaction can be recapitulated ex vivo by effectively synthesizing the critical signaling events provided by $T_{FH}$ cells and FDCs (FIG. 1a-1d, FIG. 2a) in the presence of an antigen. Traditionally, in vitro B cell activation has been achieved by engagement of CD40 molecules on B cell membrane using anti-CD40 antibodies[1], recombinant (CD40L)[2-4], or co-culture with supporting cell lines that have been genetically modified to express CD40L[5,6]. Recently, Kitamura and colleagues have developed a fibroblast-based feeder cell line that expresses both CD40L and B-cell activating factor (BAFF), particularly for the purpose of generating ex vivo GC reactions[7,8]. It was also reported that culturing these feeder cells in a hydrogel composed of Arg-Gly-Asp(RGD)-presenting extracellular matrix enhanced the co-cultured B cell survival and differentiation[9]. Despite these previous efforts, it has not been explored whether a purely synthetic, biomaterials-based design can effectively recapitulate CD40L presentation by $T_{FH}$ cells and antigen-presentation by FDCs in the context of modulation of GC reaction and generation of antigen-specific, functional B cells. Enabling mimicry of GC reactions ex vivo without the use of genetically-modified feeder cell lines offers significant advancement in designing potential applications of a sGC reaction such as i) providing a simpler, cheaper, and more rapid model for studying GC B cell physiology and pathology of B cell malignancies, ii) development of multiplex screening platforms for drugs and immunotherapeutics, and iii) ex vivo induction of effective humoral immunity in the form of therapeutic B cells as a potential B cell immunotherapy regimen.

The selective expansion of antigen-specific B cell clones is initiated by the effective antigen presentation by FDC. As these B cell clones proliferate in the GCs, the affinities toward antigenic epitopes are increased by somatic hyper-mutation (SHM) of immunoglobulin (Ig) antigen receptor genes under a concurrent selection mechanism[10-12] for high-affinity clones (affinity maturation). There has been little effort to emulate this critical aspect of the GC reaction ex vivo. If successful, such sGC reaction and ex vivo generation of high quality and high affinity antigen-specific B cells could provide significant advancement in treating various diseases that require antigen-specific humoral immunity.

The present disclosure demonstrates that GC reactions can be effectively recapitulated ex vivo by purely biomaterials-based artificial $T_{FH}$ and FDCs, as described further herein. By testing and comparing various CD40 ligation methods for their capability to induce expansion, class switch recombination, and expression of GC B cell-specific phenotypes, it was found that surface-density controlled CD40L presentation by a three dimensional structure such as microbeads were the most effective as artificial $T_{FH}$ cells. Additionally, microbead surface-bound or multimeric antigen presentation methods were successfully employed to create enriched populations of antigen-specific B cells that had undergone class-switching and somatic hypermutation, though soluble antigen presentation is also contemplated herein. These sGC reactions were successfully applied to not only spleen-isolated B cells but also the B cells isolated from peripheral blood mononuclear cells (PBMCs), a critical aspect for clinical translation. Ex vivo sGC-generated B cells engrafted to the spleen and the lymph nodes following adoptive transfer, suggesting that these cells possess a tremendous potential in immunotherapy as a novel means to confer antigen-specific humoral immunity.

Method of Ex Vivo Generation of B Cells

In one embodiment, a method of ex vivo generation of B cells in a sGC comprises the steps of:

a) isolating naïve B cells from a primary source (e.g., PMBCs, spleen, lymph node, stem/progenitor cells);

b) exposing the B cell to CD40L and to an antigen in a synthetic germinal center, at least one of which is presented on a three dimensional surface;

c) eliminating dead B cells and the three dimensional surface; and d) obtaining antigen-specific B cells with at least three characteristics selected from the group consisting of: efficient B cell expansion/proliferation, class switching recombination (CSR), antibody secretion, expression of germinal center B cell or plasma cell and somatic hypermutation (SHM) and resulting affinity maturation.

In another embodiment, a method of ex vivo generation of B cells in a sGC comprises the steps of:

a) isolating naïve B cells from a primary source (e.g., PMBCs, spleen, lymph node, stem/progenitor cells);

b) exposing the B cell to CD40L and to an antigen in a synthetic germinal center, at least one of which is presented on a microbead;

c) eliminating dead B cells and microbeads; and d) obtaining antigen-specific B cells with at least three characteristics selected from the group consisting of: efficient B cell expansion/proliferation, class switching recombination (CSR), antibody secretion, expression of germinal center B cell or plasma cell and somatic hypermutation (SHM) and resulting affinity maturation.

In another embodiment, a method of ex vivo generation of B cells in a sGC comprises the steps of:

a) isolating naïve B cells from a primary source (e.g., PMBCs, spleen, lymph node, stem/progenitor cells);

b) exposing the B cell to CD40L and to an antigen in a synthetic germinal center, at least one of which is in a soluble form;

c) eliminating dead B cells; and d) obtaining antigen-specific B cells with at least three characteristics selected from the group consisting of: efficient B cell expansion/proliferation, class switching recombination (CSR), antibody secretion, expression of germinal center B cell or plasma cell and somatic hypermutation (SHM) and resulting affinity maturation.

In an embodiment of any of the methods described above, the antigen may be present in multivalent form. In another embodiment, CD40L may be present in multivalent form. In yet another embodiment, both the antigen and CD40L are present in multivalent form.

In an embodiment of any of the above methods, step (a) further comprises sorting, classifying or purifying the naïve B cell population prior to step (b). In an embodiment of any of the above methods, the naïve B cell population can be isolated from secondary lymphoid organs such as for example and not limitation, the spleen or lymph nodes, or peripheral blood mononuclear cells (PBMCs), or can be induced from hematopoietic stem/progenitor cells isolated from, e.g., bone marrow or cord blood.

In an embodiment of any of the above methods, the CD40L is presented on an artificial/synthetic T follicular helper cell ($sT_{FH}$). In another embodiment, the $sT_{FH}$ comprises a microbead or microcarrier. In one embodiment, the CD40L is bound to the microbead or microcarrier. In one embodiment, the $sT_{FH}$ comprises a microbead coated with antibodies, and the CD40L is bound to the $sT_{FH}$ via a tag designed to interact with the antibodies. In an alternative embodiment, the $sT_{FH}$ comprises a microbead coated with streptavidin, and the CD40L is bound to the $sT_{FH}$ via a biotin tag. In a further embodiment, the $sT_{FH}$ comprises a microbead coated with anti-HA antibodies, and the CD40L is bound to the $sT_{FH}$ via a HA tag. In yet a further embodiment, the HA-tagged or biotinylated CD40L is present in multivalent form.

In an embodiment of any of the above methods, the antigen is presented on an artificial/synthetic follicular dendritic cell (sFDC). In another embodiment, the sFDC comprises a microbead or microcarrier. In one embodiment, the antigen is bound to the microbead or microcarrier. In a further embodiment, the sFDC comprises a microbead coated with streptavidin, and the antigen is bound to the sFDC via a biotin tag. In an alternative embodiment, the sFDC comprises a microbead coated with antibodies, and the antigen is bound to the sFDC via a tag designed to interact with the antibodies. In yet a further embodiment, the biotinylated or tagged antigen is present in multivalent form. In still a further embodiment, the biotinylated or tagged antigen is still capable of producing an immune response and/or activating the B cell.

In an embodiment of any of the above methods, step (b) further comprises adding soluble factors to the synthetic germinal center. In a further embodiment, the soluble factors comprise cytokines (e.g., interleukins such as for example and not limitation, IL-2, IL-4, IL-5, IL-10, IL-21), B cell growth or activation factors (e.g., BAFF), and/or ligands for toll-like receptors (e.g., LPS, CpG).

In an embodiment of any of the above methods, step (c) comprises centrifugation, fluorescence-activated cell sorting (FACS), magnetic-activated cell sorting (MACS), enzymatic degradation, various filtrations, microfluidic cell sorting, and/or size exclusion chromatography to eliminate dead cells and/or three dimensional structures.

In an embodiment of any of the above methods, step (c) further comprises purifying antigen-specific B cells. In a further embodiment, step (c) comprises cell sorting (e.g., antibody-based cell sorting such as FACS or MACS), centrifugation, microfluidic cell sorting, various filtrations, and/or size exclusion chromatography.

In an embodiment of any of the above methods, the antigen-specific B cells are used to treat the disease or condition related to the antigen. For example, B cells that were exposed to the HER2 antigen in step (b) are specific to HER2, can raise an immune response against HER2, and can be used to treat breast cancer, or other cancers associated with the HER2 antigen. Similarly, B cells that were exposed to a streptococcal antigen in step (b) are now capable of recognizing that streptococcal antigen, raising an immune response against it, and thereby treating the streptococcal infection (e.g., strep throat, impetigo, necrotizing fasciitis).

In an embodiment of any of the above methods, the resulting antigen-specific B cells can be used for adoptive B cell transfer immunotherapy for infectious diseases, cancer, autoimmune diseases; and for the production of human antibodies.

In an embodiment of any of the above methods, the CD40L is a recombinant CD40L. In another embodiment, the CD40L comprises a protein having SEQ ID NO: 18. In a further embodiment, the CD40L is tagged such that it associates with the microbead. In a specific embodiment, the CD40L comprises a protein having SEQ ID NO: 19.

Antigen Presentation

In any of the methods described above, the antigen can be presented in a soluble form or associated with a three-dimensional structure. For example and not limitation, the antigen may be associated with (e.g., bound to) a microbead (e.g., magnetic or paramagnetic microbead, polymeric microbead, polystyrene microbead, collagen bead, or glass microbead), and/or a 3-D scaffold, such as for example and not limitation, a microcarrier.

In any of the methods described above, the antigen may further be presented in a multivalent form.

In any of the methods described above, the three-dimensional support may comprise a lipid bilayer or synthetic cell membrane.

CD40 Presentation

In any of the methods described above, the CD40L can be presented in a soluble form or associated with a three-dimensional structure. For example and not limitation, the CD40L may be associated with (e.g., bound to) a microbead (e.g., magnetic or paramagnetic microbead, polymeric microbead, or glass microbead), and/or a 3-D scaffold, such as for example and not limitation, a microcarrier.

In any of the methods described above, the CD40L may further be presented in a multivalent form.

In any of the methods described above, the three-dimensional support may comprise a lipid bilayer or synthetic cell membrane.

Antigens Useful in the Disclosure

Antigens that can be utilized in the methods disclosed above include, for example and not limitation, antigens associated with and/or specific to cancers/tumors, infectious diseases, inflammatory and autoimmune diseases. The antigens may also be specific to the patient/subject from whom the B cells are isolated. Antigens include, for example and not limitation, proteins, lipids, glycolipids, nucleic acids, glycoproteins, peptides, etc.

Non-limiting examples of such cancers/tumors include, e.g., breast cancer (HER2, VGEFR), pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, brain cancers of all histopathologic types, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, Ewing's sarcoma, rhabdomyosarcoma, carcinoma of unknown primary (CUP), squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, testicular tumor, glioma, glioblastoma, astrocytoma, medulloblastoma, craniopharyngioma, ependymoma, pinealoma, hemangioblastoma, acoustic neuroma, oligodendroglioma, meningioma, retinoblastoma, leukemia, neuroblastoma, small cell lung carcinoma, bladder carcinoma, lymphoma, multiple myeloma, medullary carcinoma, B cell lymphoma, T cell lymphoma, NK cell lymphoma, large granular lymphocytic lymphoma or leukemia, gamma-delta T cell lymphoma or gamma-delta T cell leukemia, mantle cell lymphoma, myeloma, leukemia, chronic myeloid leukemia, acute myeloid leukemia, chronic lymphocytic leukemia, acute lymphocytic leukemia, hairy cell leukemia, hematopoietic neoplasias, thymoma, sarcoma, non-Hodgkin's lymphoma, Hodgkin's lymphoma, Epstein-Barr virus (EBV) induced malignancies of all types including but not limited to EBV-associated Hodgkin's and non-Hodgkin's lymphoma, all forms of post-transplant lymphomas including post-transplant lymphoproliferative disorder (PTLD), uterine cancer, renal cell carcinoma, hepatoma, hepatoblastoma, etc.

Non-limiting examples of infectious diseases include, e.g., bacterial diseases, viral diseases, fungal diseases, protozoal/parasitic diseases, etc.

Non-limiting examples of inflammatory and autoimmune diseases include, e.g., inflammatory bowel disease (IBD), graft-versus host disease (GVHD), ulcerative colitis (UC), Crohn's disease, diabetes (e.g., diabetes mellitus type 1), multiple sclerosis, arthritis (e.g., rheumatoid arthritis), Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions, autoimmune neuropathies, etc.

Non-limiting examples of bacterial diseases include, e.g., Lyme disease, granuloma inguinale, bacterial vaginosis, gonorrhea, syphilis, congenital syphilis, mycobacterium avium complex, melioidosis, anthrax, leptospirosis, whooping cough, leprosy, tetanus, plague, bubonic plague, pneumonic plague, scarlet fever, streptococcal infections, invasive Group A streptococcal disease, streptococcal toxic shock syndrome, meningococcal disease, bacteremia, strep throat, cholera, dysentery, amebic dysentery, shigellosis, diphtheria, cutaneous diphtheria, respiratory diphtheria, Legionnaires' disease, tuberculosis, latent tuberculosis, Hemophilus influenzae B infection, typhoid fever, Rocky Mountain spotted fever, vibrio infections, yersiniosis, Whipple's disease, bacterial digestive infections, acute appendicitis, meningitis, bacterial meningitis, encephalitis, impetigo, cellulitis, carbuncle, boil, acne, sepsis, septicemia, pneumonia, ptomaine food poisoning, *Salmonella* food poisoning, Staphylococcal infection, *Staphylococcus aureus* food poisoning, botulism food poisoning, *E. coli* food poisoning, rheumatic fever, brucellosis, ehrlichiosis, psittacosis, relapsing fever, diarrheagenic *Escherichia coli*, listeriosis, scombrotoxic fish poisoning, trachoma. *Chlamydia pneumonia* infections, *Mycoplasma pneumoniae* infections, mycobacterial infections, Q fever, STARI, Yaws, actinomycosis, Lymphogranuloma venereum, conjunctivitis, prostatitis, pericarditis, abscess, endocarditis, myelitis, osteomyelitis, dermatitis, fever, pertussis, urinary tract infection, etc.

Non-limiting examples of viral diseases include, e.g., common cold, chickenpox, flu (influenza), herpes, human immunodeficiency virus (HIV/AIDS), human papillomavirus (hpv), infectious mononucleosis, mumps, measles, rubella, shingles, viral gastroenteritis (stomach flu), viral hepatitis (Hepatitis A, Hepatitis B, and/or Hepatitis C), viral meningitis, viral pneumonia, Herpes simplex virus 1 infection, Herpes simplex virus 2 infection, Kaposi sarcoma, multicentric Castleman disease, Reye syndrome, poliomyelitis, rabies, etc.

Non-limiting examples of fungal diseases include, e.g., aspergillosis, blastomycosis, candidiasis, coccidioidomycosis (Valley fever), *Cryptococcus neoformans* infection, *Cryptococcus gattii* infection, keratitis, endophthalmitis, histoplasmosis, mucormycosis, *Pneumocystis* pneumonia, ringworm, sporotrichosis, *Exserohilum* and *Cladosporium* infections, etc.

Non-limiting examples of protozoal/parasitic diseases include, e.g., *Acanthamoeba* infection, granulomatous amebic encephalitis, *Naegleria* infection, amoebiasis, giardiasis, African sleeping sickness, Leishmaniasis, toxoplasmosis, malaria, babesiosis, trichomoniasis, Chagas disease, trypanosomiasis, ancylostomiasis, cercarial dermatitis, filariasis, lymphatic filariasis, enterobiasis, roundworm infection, hookworm infection, tapeworm infection, whipworm infection, onchocerciasis, etc.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1—Development of Ex Vivo System

Ligation of CD40 by Either Soluble Anti-CD40 Antibody or Soluble Recombinant CD40L (CD154) Induces Incomplete B Cell Activation and GC Reaction.

Figure 2B:
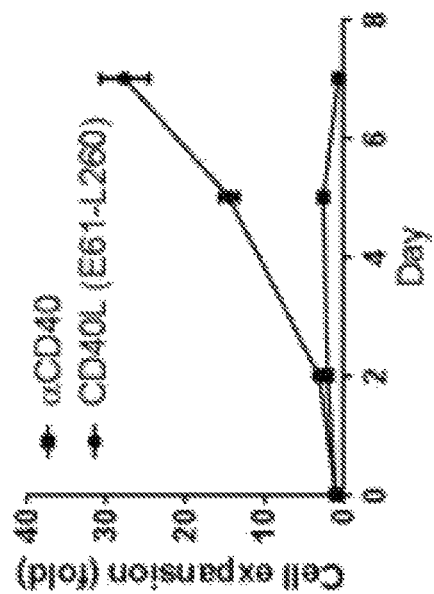
Figure 2A:
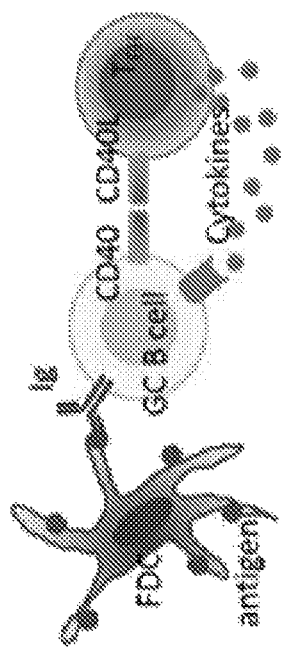
Figure 2C:
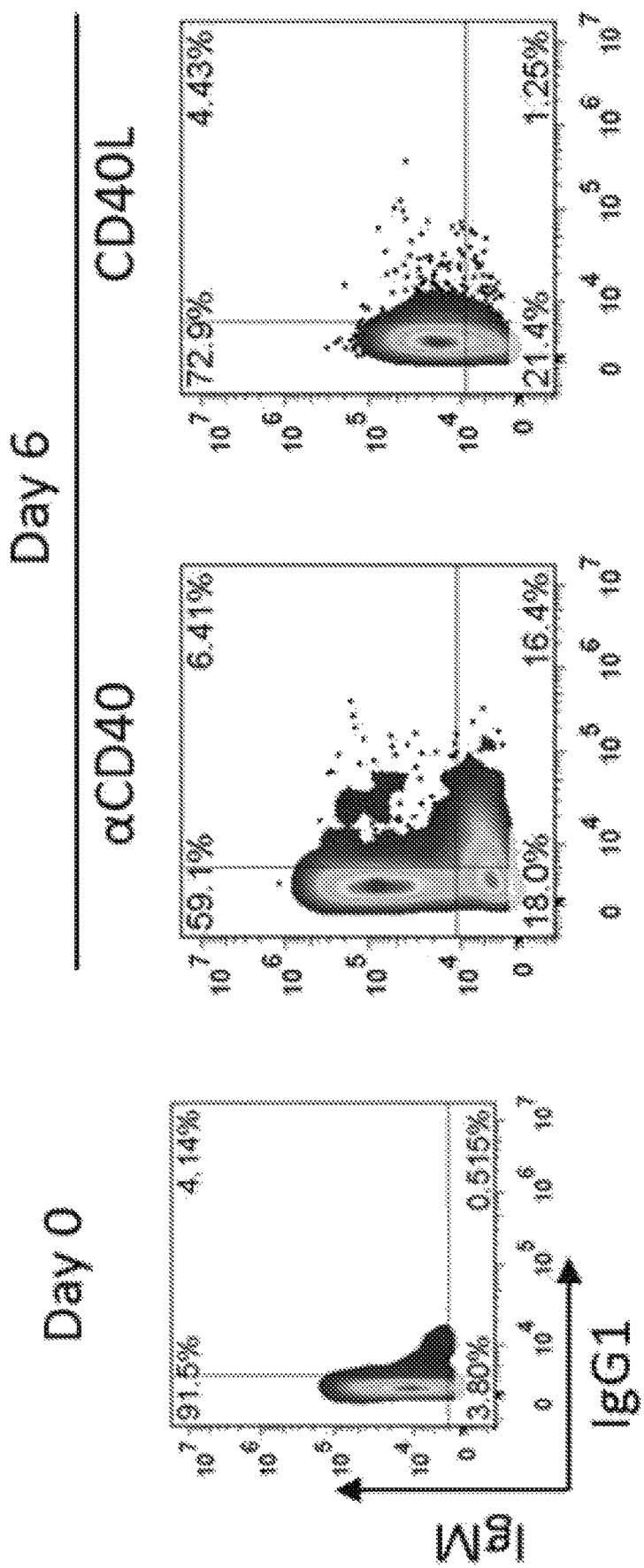
Figure 2C:
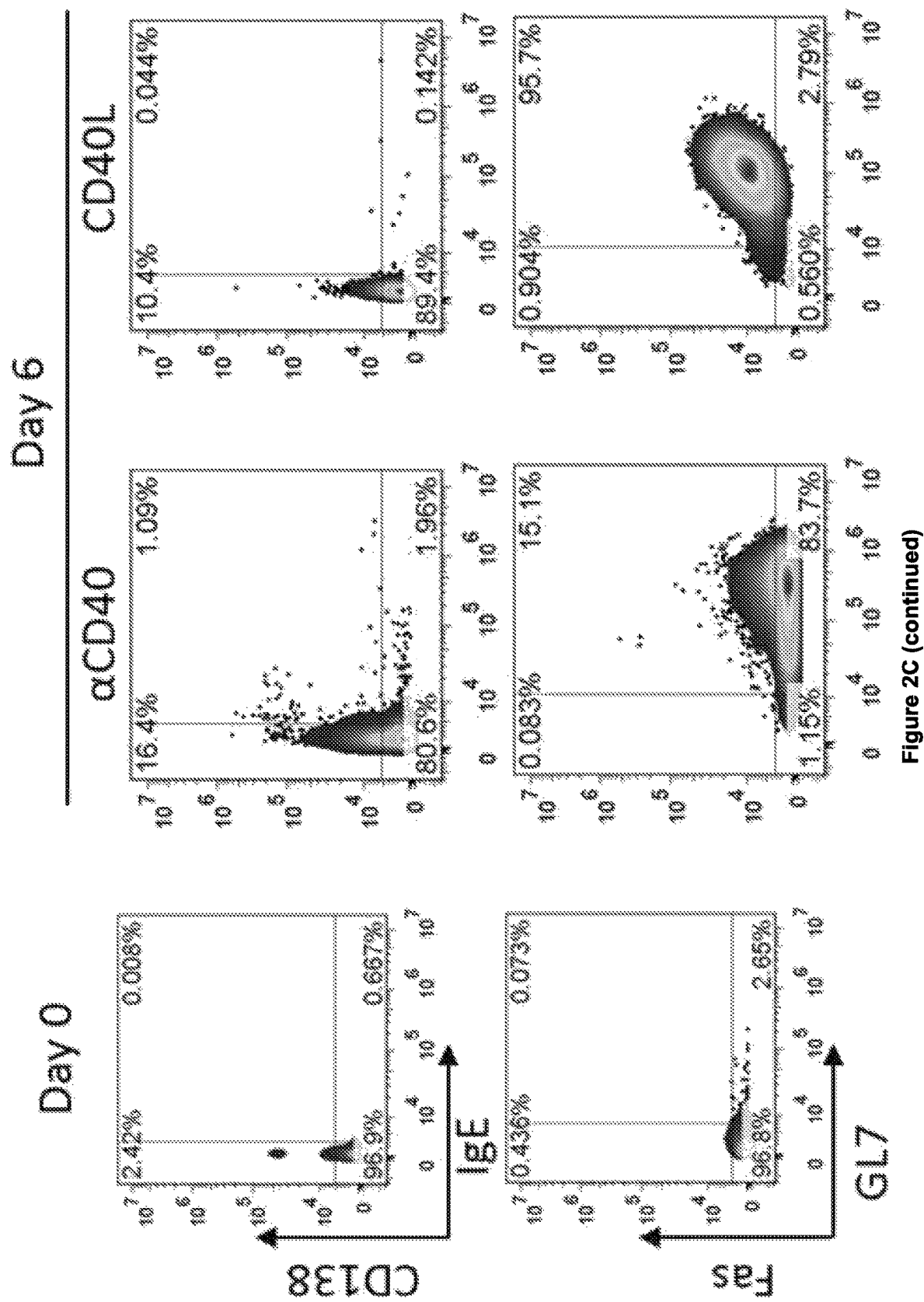

For effective activation of B cells in the GC reaction, both CD40-CD40L (CD154) interaction and the soluble factors secreted by $T_{FH}$ and FDCs—including interleukins (e.g. IL-4) and B cell activating factor (BAFF)—provide critical signals[13]. (FIG. 1a-1d, FIG. 2a). As soluble anti-CD40 antibody (αCD40) or recombinant CD40L have traditionally been used for B cell activation, the quality and quantity of B cell activation that these soluble CD40 ligations induce was first tested. In the presence of IL-4 and BAFF, splenic B cells were cultured with either αCD40 (Clone 1C10) or CD40L (E61-L260) for 7 days. In both cultures, B cells formed spheroid-looking aggregates within 2 days. However, only the culture with CD40L yielded significant B cell expansion (FIG. 2b). For B cells activated by αCD40, cell viability measured on Day 6 was only about 2 to about 5%, thus implying that αCD40 culture induces apoptosis. Flow cytometry was employed to examine class switch recombination (CSR), differentiation into plasma cells, and expression of GC phenotypes (FIG. 2c, 2d). A moderate level of CSR from IgM to IgG1 and expression of CD138, the plasma cell marker, was achieved in the culture using αCD40 compared to the minimal CSR and CD138 expression in the culture with CD40L. Conversely, CD40L was superior in induction of GC phenotypes (GL7+ Fas+) to αCD40. Thus in the perspective of GC reaction, αCD40 was more effective in induction of CSR than CD40L, but CD40L was superior to αCD40 in B cell expansion and in differentiation to GC-like B cells (FIG. 2e). Therefore, both natural ligation of CD40 using CD40L and crosslinking of CD40 may be necessary to induce an effective synthetic GC (sGC) reaction.

Microbead-Based Artificial $T_{FH}$ Design Presenting CD40L with a Controlled Surface Density Effectively Induced sGC Reaction.

Figure 3B:
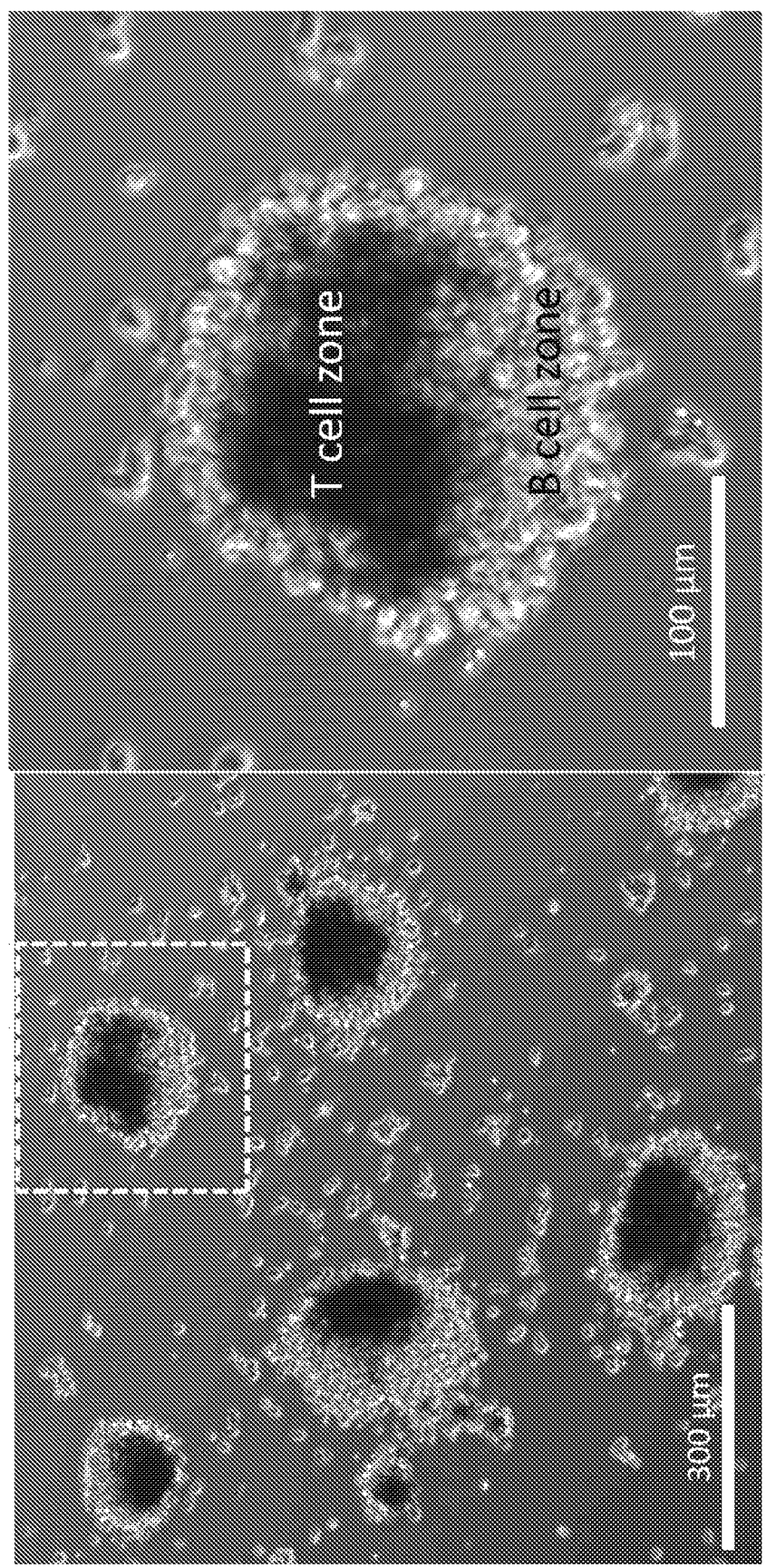

In order to induce effective crosslinking of CD40 while leveraging the natural CD40-CD40L ligation, a microbead-based artificial $T_{FH}$ cell was designed using recombinant CD40L tagged with HA peptide and iron oxide microbeads coated with anti-HA antibodies (FIG. 3a). Using this artificial $T_{FH}$, sGC reaction was induced in presence of BAFF and IL-4. Splenic B cells quickly formed a complex with these artificial $T_{FH}$, and grew as an organoid structure mimicking physiological germinal centers within 48 hours (FIG. 3b). As these sGC structures developed, areas enriched with artificial $T_{FH}$ microbeads (darker under phase contrast optical microscope) often separated from the areas enriched with B cells.

The unique advantage of such a biomaterial-based sGC design is that critical reaction parameters can be quantitatively controlled and tested. Specifically, it was investigated how the sGC reaction can be modulated by controlling the dose of CD40L, the surface density of CD40L, and the ratio of B cells to artificial $T_{FH}$ microbeads. sGC reaction conditions using soluble CD40L, with or without the soluble crosslinking antibody, were also tested for direct comparisons. First, the dose of CD40L was optimized by testing a range of densities over several orders of magnitude—from 0.1 to 100 ng ml$^{-1}$ per $10^5$ cells. Microbeads were coated with CD40L molecules at a maximum density, approximately $2.7 \times 10^4$ molecules $\mu m^{-2}$. To achieve the maximum dose (100 ng ml$^{-1}$ for $10^5$ cells), approximately 100 microbeads per B cell were needed. Two different methods were employed to test lower doses—first by lowering the cell to bead ratio while keeping the maximum CD40L surface density constant, and second by lowering the CD40L surface density while keeping the cell to bead ratio constant (at 1 to 100). B cell expansion, measured by live cell count on Day 6 of sGC culture (FIG. 3c), showed a clear CD40L-dose dependence. Further, the presence of soluble crosslinking antibody for soluble CD40L significantly increased cellular expansions. The expansion of B cells in sGC culture with microbead surface-bound CD40L increased in a dose dependent manner up to 10 ng ml$^{-1}$, but decreased at the maximum dose. This decrease in B cell expansion at the maximum dose is likely due to cytotoxicity from high number of microbeads, which is supported by the fact that better B cell expansion was achieved by lowering [cell:bead] ratio to 1:10 compared to lowering the surface density of CD40L for the same dose of 10 ng ml$^{-1}$.

Figure 3D:
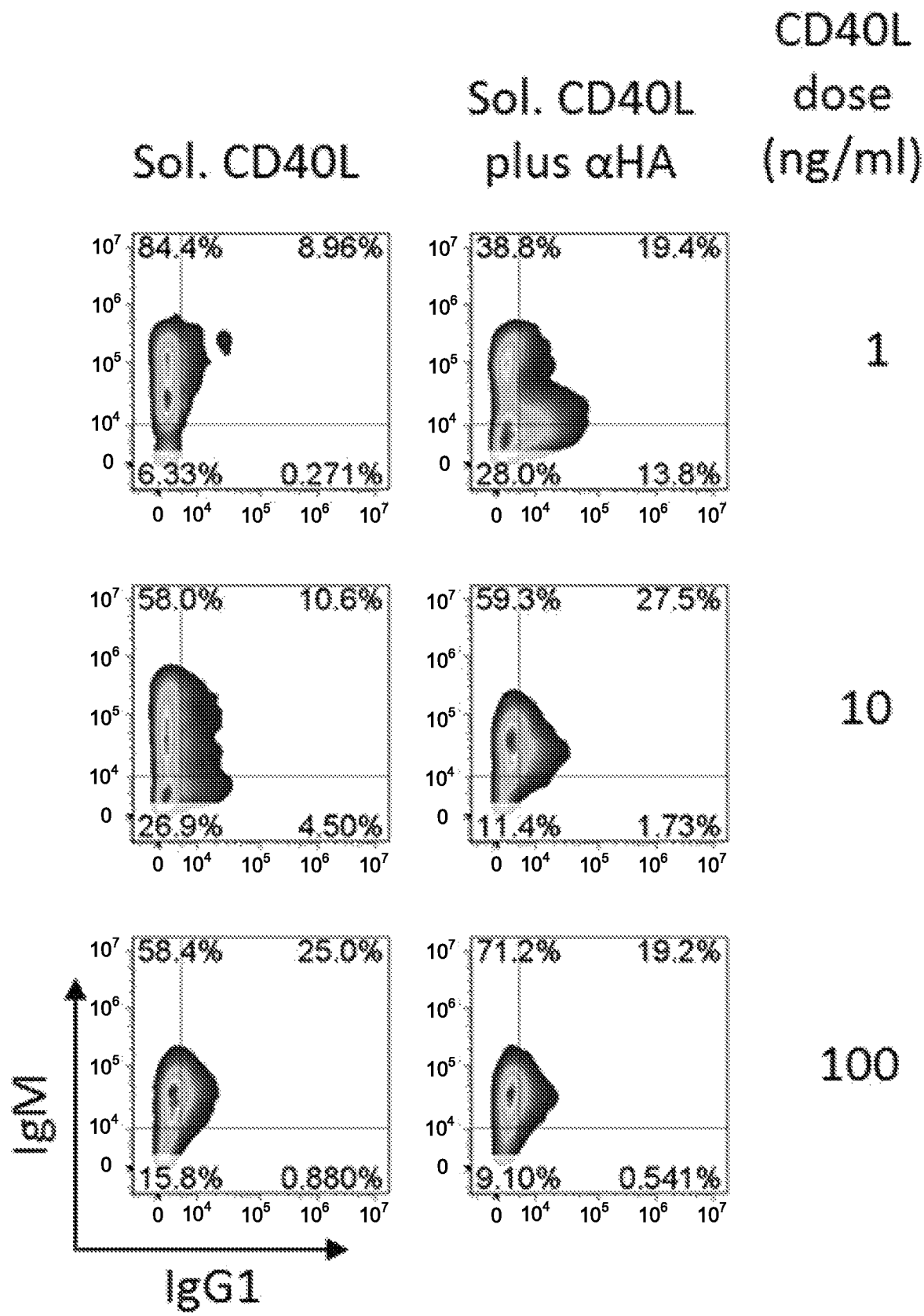
Figure 3D:
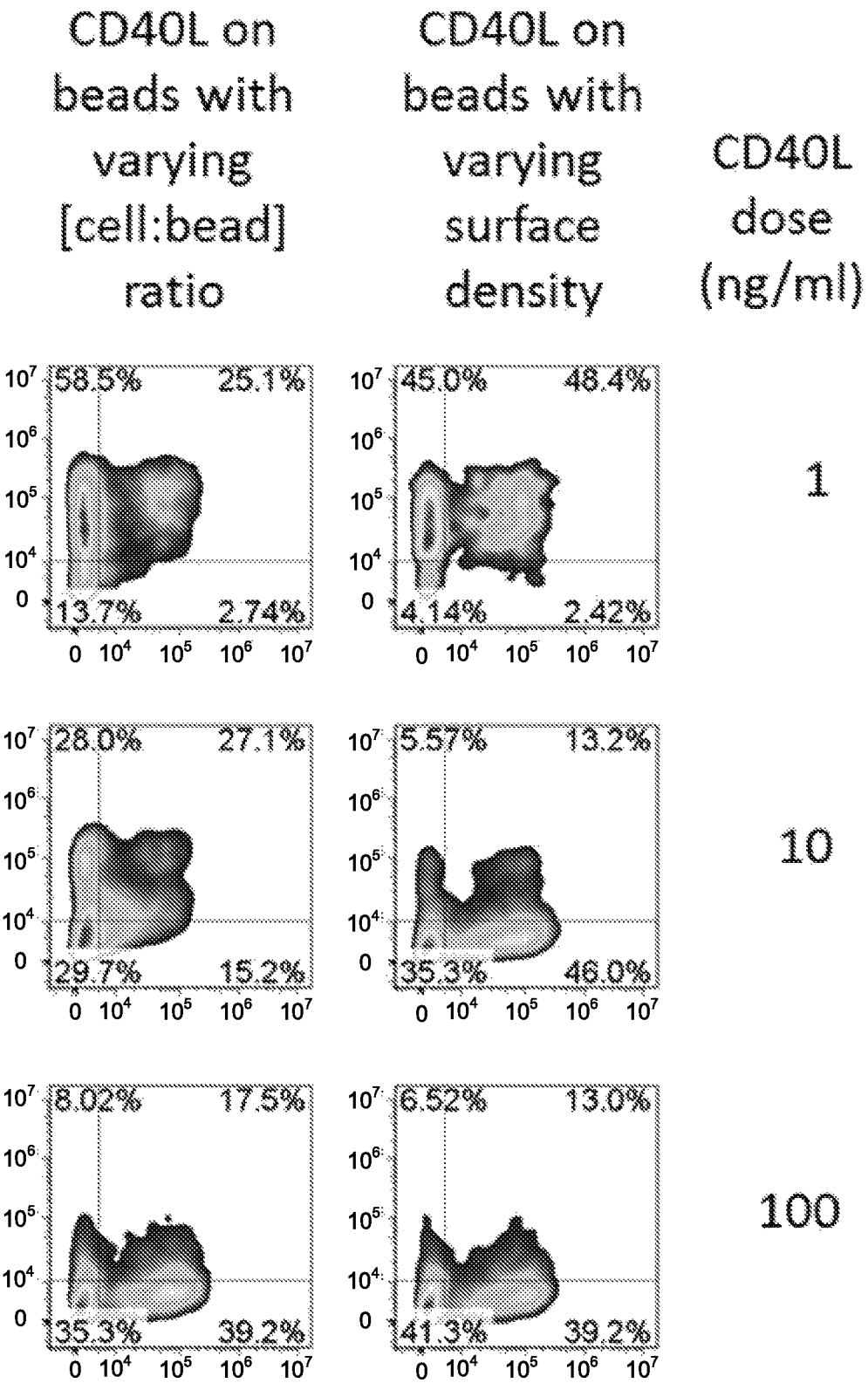

Next, using flow cytometry, the CSR and differentiation status of the B cells harvested at Day 6 of each sGC culture was investigated. First, the use of microbeads-bound CD40L as artificial $T_{FH}$ significantly improved the CSR, compared to the soluble systems (FIG. 3d-3f). Interestingly, in the case of soluble CD40L plus soluble crosslinking antibody, the CSR to IgG1 was inversely proportional to the dose of CD40L. However, microbeads-presented CD40L not only enhanced the percentage of IgG1+ cells with increasing dose of CD40L but also induced more complete switching of isotypes, indicated by an increasing shift from IgM+IgG1+ double positive to IgM−IgG1+ single positive populations and significant increased the expression of the IgG1 isotype.

Second, the differentiation status of resulting B cells was also tested by checking the expression of typical GC B cell markers, GL7+Fas+ and CD38-CD80+(FIG. 3g-3h, FIG. 10 and FIG. 11). When the two highest CD40L doses of all the culture conditions were compared, cultures with microbeads based artificial $T_{FH}$ cells induced equivalent (GL7+Fas+) or more (CD38-CD80+) GC B cell populations (>80%) compared to the number generated in culture conditions with soluble CD40L. Altogether, it was concluded that effective recapitulation of $T_{FH}$ cell functions was most likely achieved by using controlled surface presentation of CD40L on the microbeads to modulate the quality and strength of CD40-CD40L ligations. The T cell dependent critical aspects of germinal center reaction, i.e., B cell expansion, CSR, and expression of GC B cell phenotypes, were successfully achieved in vitro.

Figure 12A:
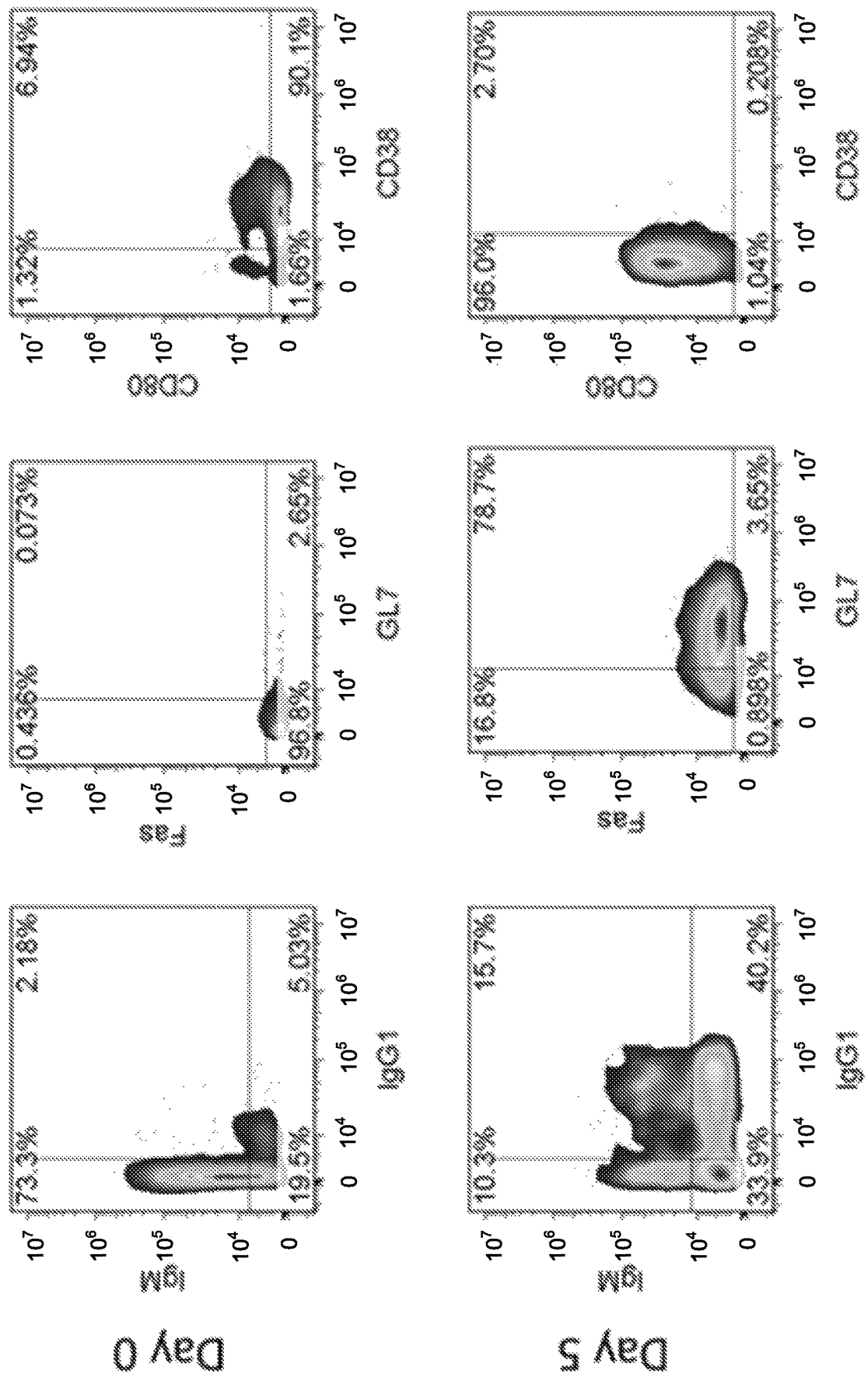
FIG. 12a-12b. Outcome of 5-day sGC culture applied to PBMC isolated B cells. (12a) Flow cytometry analysis to determine class switching recombination (CSR) and expression of GC B cell phenotypes by examining the expression levels of IgG1 and IgM (left), GL7 and Fas (middle), and CD38 and CD80 (right), for before (Day 0, upper) and after (Day 5, lower) the sGC culture. (12b) Percentage of indicated populations were plotted with the means and s.d. acquired from triplicates.
Figure 12B:
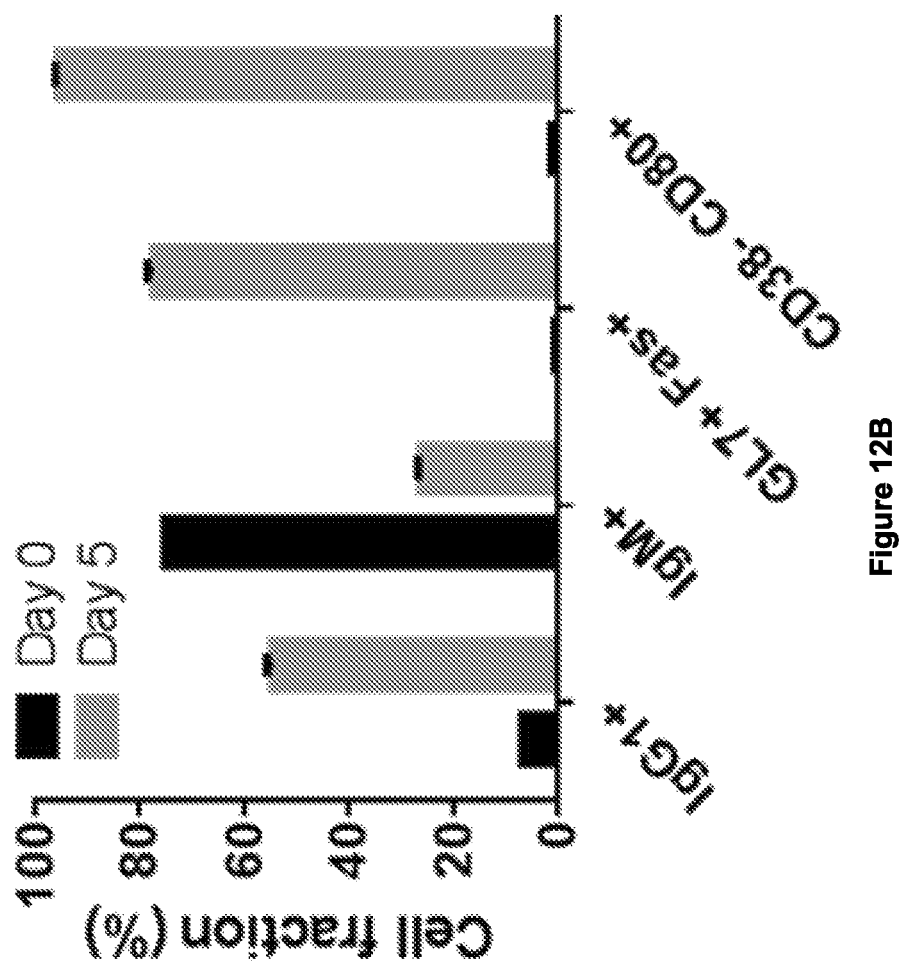

It is noteworthy that this sGC reaction was also successfully applicable to B cells isolated from PBMCs (FIG. 12), and completely transformed the majority of non-class switched naïve B cell populations to IgG1+GC B cells within 5 days of culture.

IL-4 Induced sGC B Cells are Transcriptionally Similar to Centrocytes and Commit to Plasma Cell Lineage Upon Incubation in IL-21.

The transcriptional programs involved in the sGC B cell differentiation process were investigated by using real-time quantitative PCR (RT-PCR) analysis. First, the expression level of activation induced cytidine deaminase (AICDA or AID), which is known to be highly expressed in GC B cells and is involved in both CSR and SHM, was tested.[14-16] As expected, sGC B cells expressed high levels of AICDA mRNA within 3 days of culture, compared to naïve follicular B cells as well as antigen-specific natural GC (nGC) B cells isolated 2 weeks after vaccination (FIG. 4a). BCL6 is known to be a critical transcriptional factor involved in GC reaction, as mice deficient in BCL6 are characterized by lack of GC formation and inability to produce affinity-matured antibodies.[17,18] However, expression levels of BCL6 mRNA in sGC B cells are lower than total natural GC B cells and even lower than follicular B cells (FIG. 4b). This data can be explained by the fact that GC B cells are composed of two sub-stages, centroblasts and centrocytes, in early and later stages of GC reactions, respectively. BCL6 is upregulated in rapidly proliferating centroblasts and is involved in transcriptional repression of many genes to suppress the premature activation and apoptosis of early GC B cells. However, only a small percentage of centroblasts are further activated by T-cell dependent CD40 signaling, proceeding into centrocytes in which BCL6 expression is downregulated.[19] The release from BCL6 transcriptional repression is required for CSR, SHM, and further differentiation of centrocytes into memory B cells and plasma cells.[20] Therefore, the majority of the sGC B cells seem to be differentiated into centrocyte stage much more quickly than in a natural GC reaction, possibly due to the ubiquitous activation with CD40-signaling.

Figure 13C:
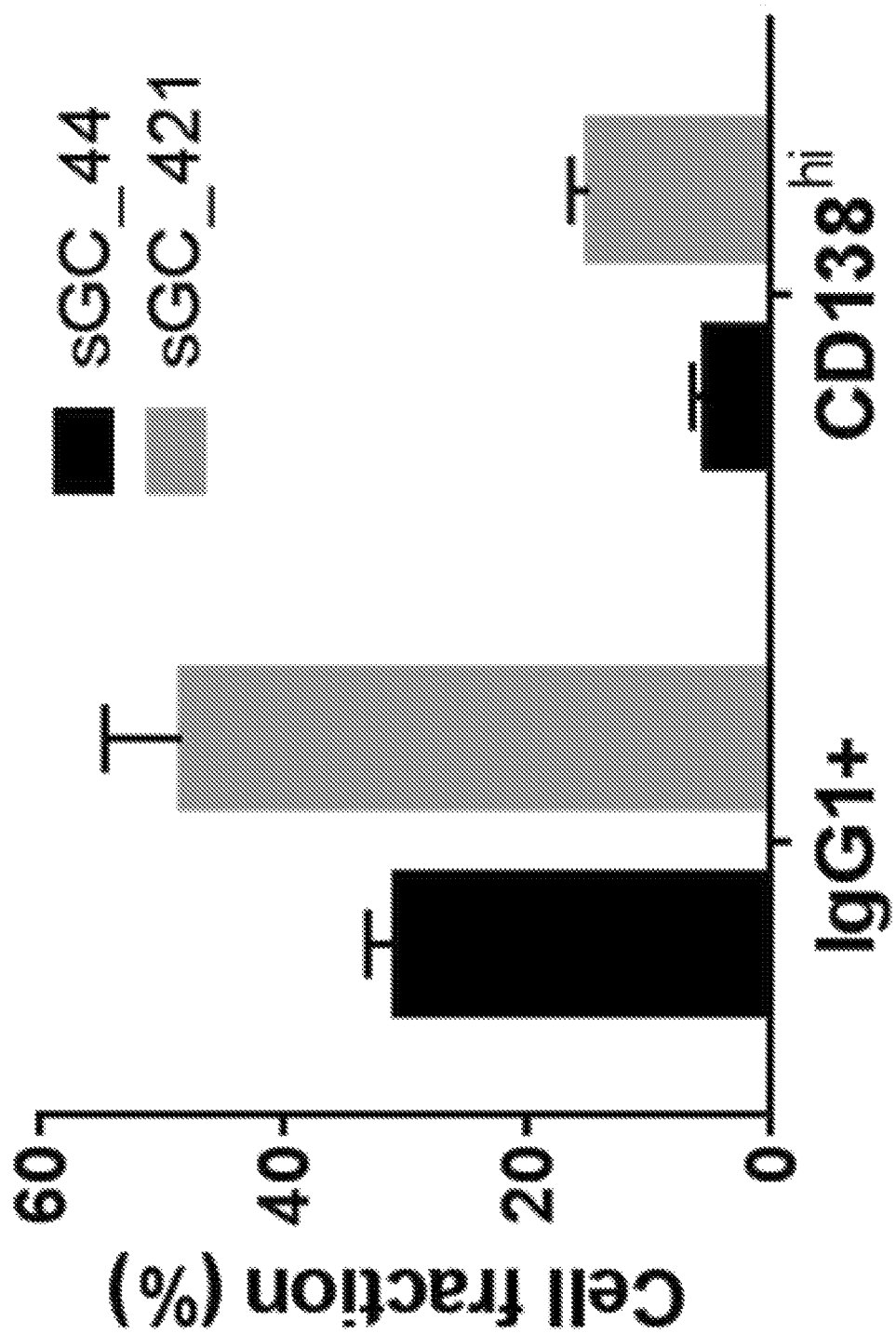

In a separate experiment, it was observed that switching the exogenous cytokine from IL-4 to IL-21 on Day 3 of sGC culture (sGC_421) enhanced the IgG1-expressing populations and the plasma cell marker, CD138-positive populations, compared to maintaining IL-4 for the whole sGC culture period of 6 days (sGC_44) (FIG. 13). In order to understand these cytokine-induced phenotypic changes at a transcriptional level, the sGC_44 and sGC_421 cells were also examined by RT-PCR analysis separately. Both AICDA and BCL6 are down-regulated when IL-4 is switched to IL-21 (FIG. 4a, 4b). Thus, switching to IL-21 seems to slow down the IL-4 induced sGC reactions such as CSR and SHM, but further appears to increase the speed of differentiation of GC B cells by suppressing BCL6. As it has been shown that IL-21 together with CD40L promote differentiation of centrocytes to plasma cells by upregulation of transcriptional factor Blimp-1,[21] the expression level of PRDM1 gene that encodes Blimp-1 was also examined. PRDM1 has been shown to be expressed in a small subset of centrocytes and is critically required for the formation and maintenance of plasma cells.[22,23] The sGC B cells at Day 3 under IL-4 already express higher levels of PRDM1 compared to follicular B cells or natural GC B cells (FIG. 4c). Among the sGC B cells that are maintained under IL-4 for 6 days (sGC_44), only the CD138+ cells express upregulated level of PRDM1. And upon switching IL-4 to IL-21, PRDM1 mRNA level was indeed greatly enhanced both in CD138− and CD138+ populations (FIG. 4c).

Altogether, the sGC B cells induced under IL-4 seem to be able to undergo AICDA-dependent GC reactions such as CSR and SHM, and rapidly differentiate into a centrocyte-like state by suppressing BCL6 activity. Upon switching cytokine environment from IL4- to IL-21, AICDA is down-regulated and differentiation commitment into plasma cell lineage is greatly enhanced.

Enriched Populations of Functional Antigen-Specific B Cells were Effectively Induced by sGC Reaction Following Fluorescence Activated Cell Sorting (FACS).

In order to fully recapitulate the induction of antigen-specific humoral immunity as a result of physiological GC reactions, the selection of B cell populations containing antigen-specific immunoglobulin membrane receptors were tested by use of fluorescence activated cell sorting (FACS). Whole protein ovalbumin (OVA) was first chosen as a model antigen, for which two labeling strategies were tried: i) labeling with unmodified OVA followed by FITC-conjugated rabbit polyclonal anti-OVA antibodies (Abcam); ii) labeling with OVA-tetramers formed between custom prepared biotinylated OVA and PE-conjugated streptavidin. The first strategy takes advantage of commercially available anti-OVA antibodies. Meanwhile, it is theoretically possible to apply the second labeling strategy to any antigen of interest. However, this method carries a risk of losing some natural epitopes of a protein antigen if the amino acid within an epitope is used for the biotin-modification. Nevertheless, both strategies typically yielded ~0.2% cells of spleen isolated naïve B cell populations that are positively stained at a varying degree of fluorescence signal with the antigen. This population is a mixture of naïve B cell clones that possess membrane immunoglobulin receptors with mixed levels of affinity toward the antigen. For the selection of a B cell population with receptors towards a more defined epitope, peptide-tetramers of an H-2b-restricted class II OVA epitope, OVA (323-339, ISQAVHAAHAEINEAGR (SEQ ID NO: 1)) were used. The peptide-tetramer was freshly prepared by incubation of PE-streptavidin with excess of N-terminal biotin-labeled OVA peptide followed by purification steps. Using this tetramer of a single OVA epitope, the fraction of positive staining naïve B cell population is reduced to 0.02%~0.1%, as expected.

Figure 5A:
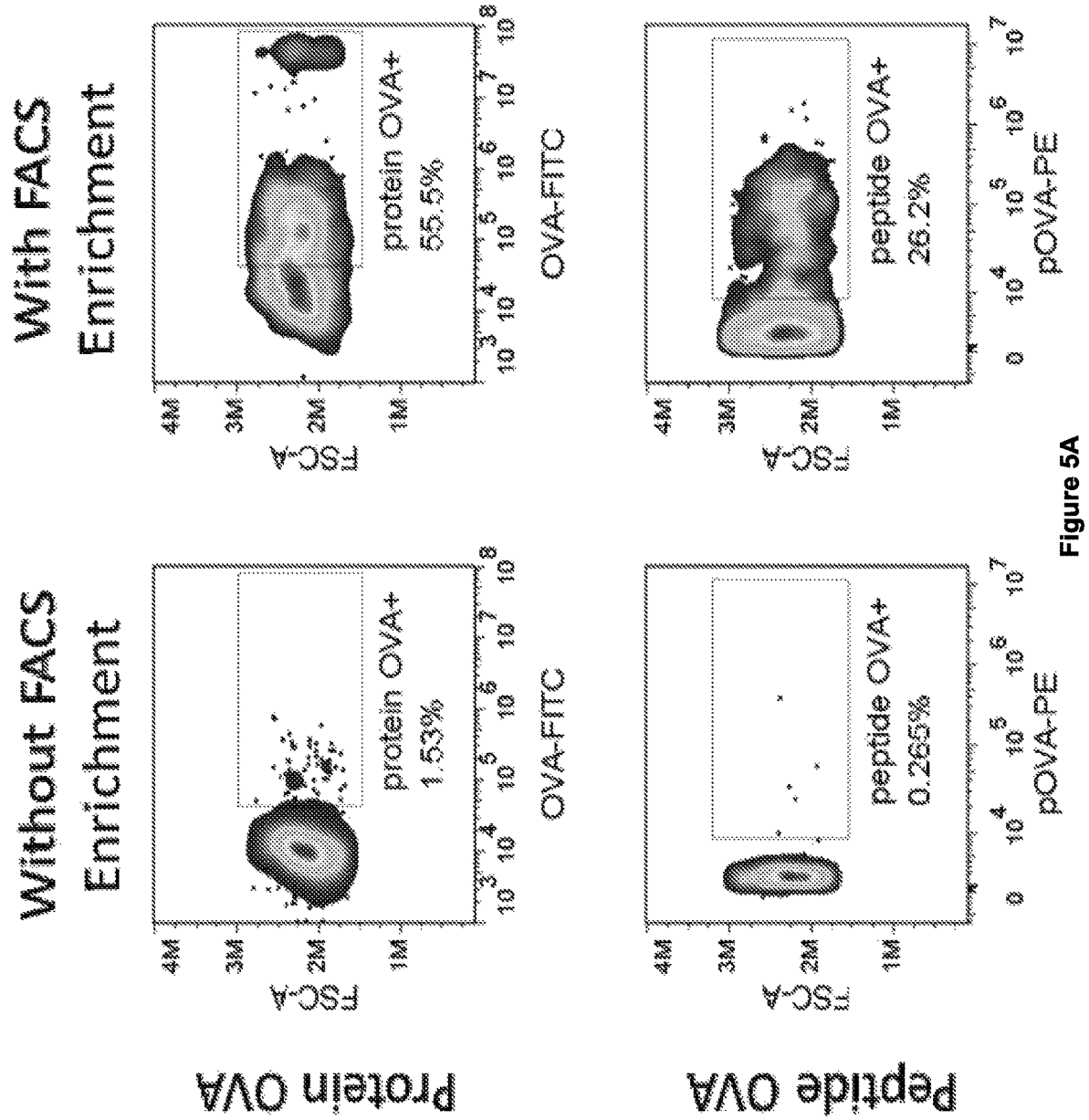
FIG. 5a-5c. sGC reaction for antigen-specific B cells isolated by FACS enrichment. (5a, 5b) Flow cytometry analysis for antigen-specificity of the resulting B cell populations after 6-day sGC cell culture. (5a) Representative flow cytometry data for the day-6 sGC B cells stained with whole protein OVA followed by detection using FITC-conjugated anti-OVA antibody (upper panel), or stained with PE-conjugated peptide-OVA (323-339) tetramer (lower panel), with (right panel) or without (left panel) after the initial FACS enrichment step. (5b) Percentage of antigen-specific B cell populations in total B cells after 6-day sGC culture with (FACS+) or without (FACS−) the initial FACS enrichment steps. The model antigens, protein OVA or peptide-OVA tetramer, were accordingly added into the sGC culture medium at 1 µg ml$^{-1}$ on Day 0 and Day 3. Mean and s.d. were calculated from 3 (protein OVA) and 5 (peptide OVA) separate experiments, and the indicated numbers are fold enrichments. (5c) The frequency of anti-OVA antibody secreting cells (ASCs) among the resulting B cells after 6-day sGC culture, determined by ELISPOT assay. Shown is the mean and s.d. of triplicates. Photographs are representative images of ELISPOT wells of each condition following the order of shown in graph from left to right.
Figure 5B:
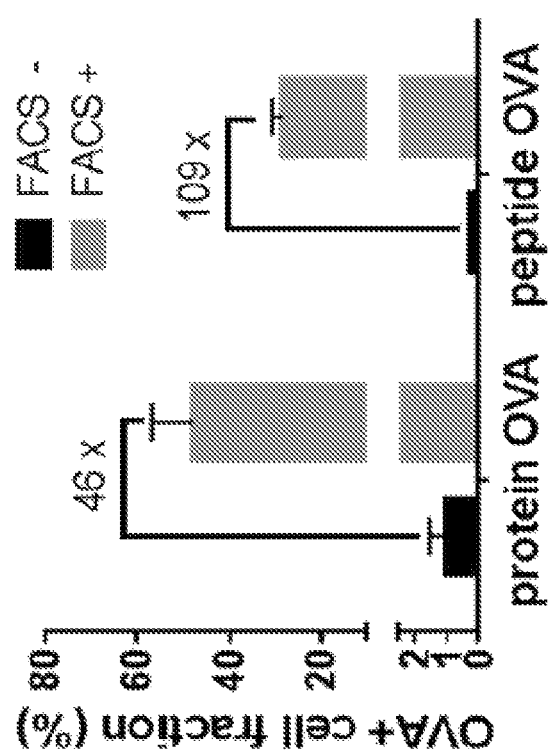
Figure 5C:
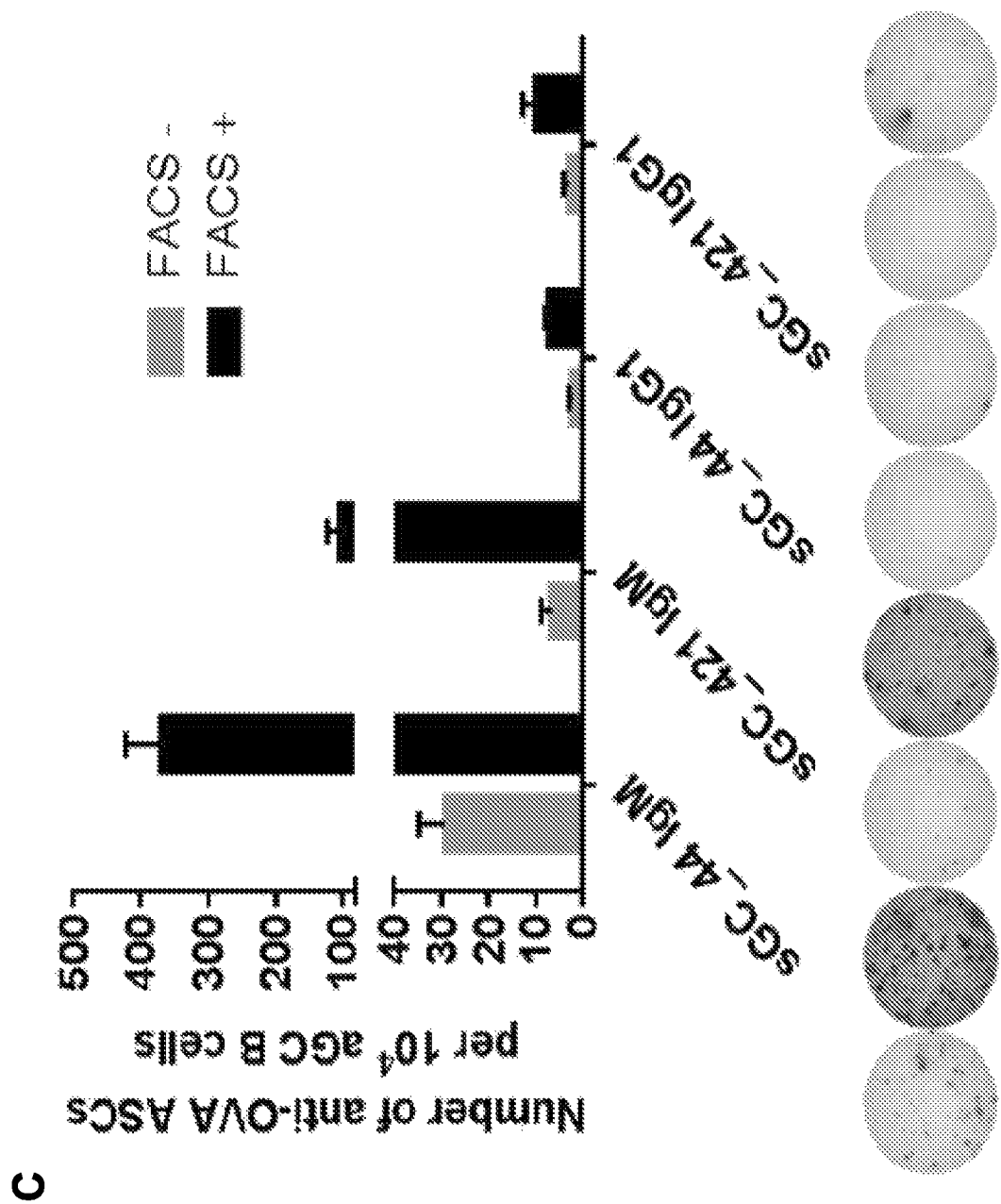

Using these fluorescence-labeling strategies, the antigen-specific B cell populations were enriched via FACS before introducing them to sGC cultures. Without FACS enrichment, the staining pattern after 6 days of sGC reaction was not very different from the staining pattern of naïve B cells (FIG. 5a, left panel). But the FACS-enriched populations showed a significantly enhanced positive fraction in both protein (>50%) and peptide (>25%) OVA staining (FIG. 5a, right panel). On average, FACS-enriched populations contained 46 and 109 times higher fractions of antigen-specific B cells after sGC reactions compared to the non-enriched B cells for protein and peptide OVA, respectively (FIG. 5b). Next, the number of OVA-specific antibody secreting cells (ASCs) created by sGC reactions were examined with and without the FACS enrichment by ELISPOT assay (FIG. 5c). For both sGC_44 and sGC_421 conditions, the FACS enrichment produced a significantly higher number (~14 times for IgM, ~3 times for IgG1) of OVA specific ASCs (FIG. 5c), which validated the use of FACS enrichment. Interestingly, the ASCs generated from the sGC reactions were still mostly of IgM isotype. This result is similar to the physiological immune responses, where IgM is always the first class of antibody secreted from the initially generated plasmablasts. Nevertheless, by combination of flow cytometry and ELISPOT, it was ultimately confirmed that the antigen-specific enrichment by FACS followed by sGC reaction will be useful for the generation of antigen-specific ASCs.

Microbead Surface-Bound Antigen Presentation During sGC Reaction Selectively Increased the Fraction of Antigen-Specific B Cell Population.

Figure 14:
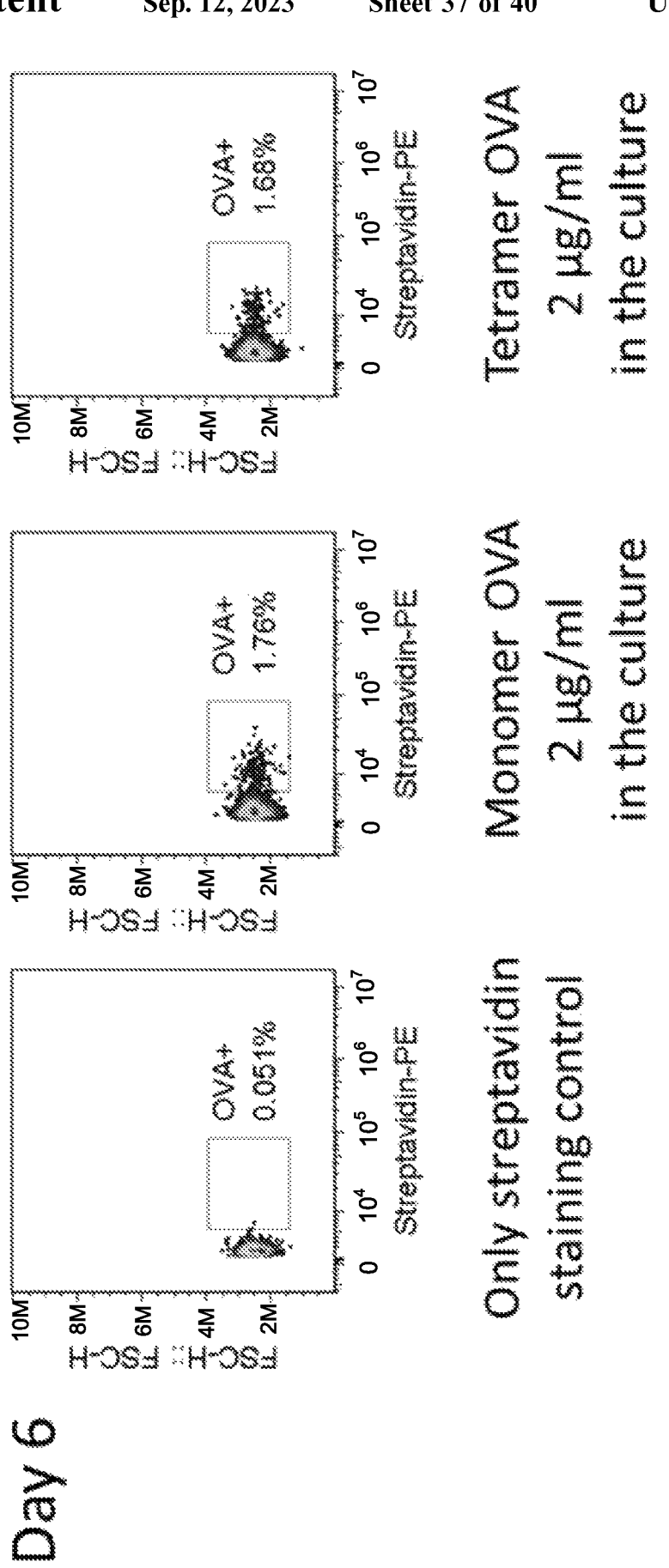
FIG. 14. Size of OVA-specific B cell populations before (Day 0) and after (Day 6) sGC cultures with or without the soluble OVA antigens (2 µg ml$^{-1}$). The OVA-specific B cell populations were detected by flow cytometry analysis followed by staining with PE-conjugated OVA-tetramer. The indicated numbers are the percentages of gated populations for the positively stained B cells.

In a physiological GC, B cells are given opportunities to survey the antigens presented by follicular dendritic cell. Those B cells that possess antigen-specific B cell receptors (BCRs) bind to, internalize, and process (degrade) the antigen, and further present the antigenic epitopes to the T cells in a major histocompatibility complex-restricted manner. This antigen-BCR interaction and cell-cycle-dependent subsequent signaling enables the clonal selection and proliferation of antigen-specific B cells by either enhancing survival of high-affinity B cells[11] or by better antigen presentation to the T cells[12]. Thus, it was tested how presenting antigens in the described sGC reaction affects the antigen-specific populations. First, the size of OVA-specific B cell populations after 6 days of sGC cultures with or without the presence of soluble OVA antigens were compared. When 2 µg ml$^{-1}$ of monomeric soluble OVA was added to sGC reactions, the OVA-specific populations grew to 1.76% compared to 0.26% without OVA during the culture (~6 times increase, FIG. 14). Using the same doses of OVA, multimeric OVA induced an expansion of OVA-specific B cells in similar quantity to the monomeric OVA.

Figure 6A:
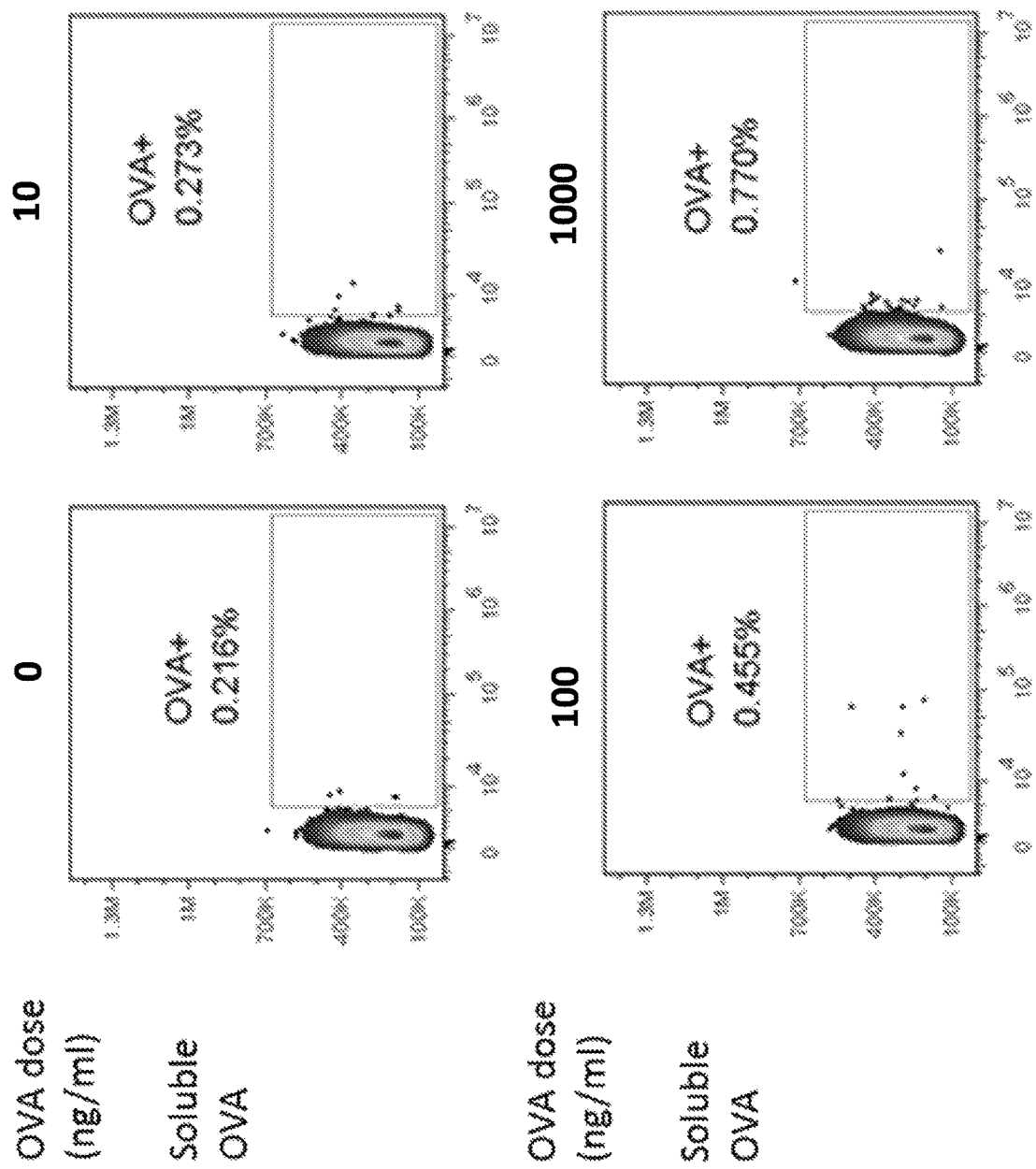
FIG. 6a-6b. Selective increase of antigen-specific B cell populations in the presence of antigens during sGC culture. (6a) Collection of representative flow cytometry data for resulting B cells after 6-day sGC culture stained with PE-conjugated OVA-tetramers. The indicated dose of OVA molecules was added into the culture in a soluble form (upper panel) or in a bead-bound form (lower panel). (6b) Percentage of OVA-specific B cell populations, shown as mean and s.d. from triplicates for each condition. Statistical significance for the difference between conditions was confirmed by Student t-test and indicated by * for P<0.05; ** for P<0.01.
Figure 6A:
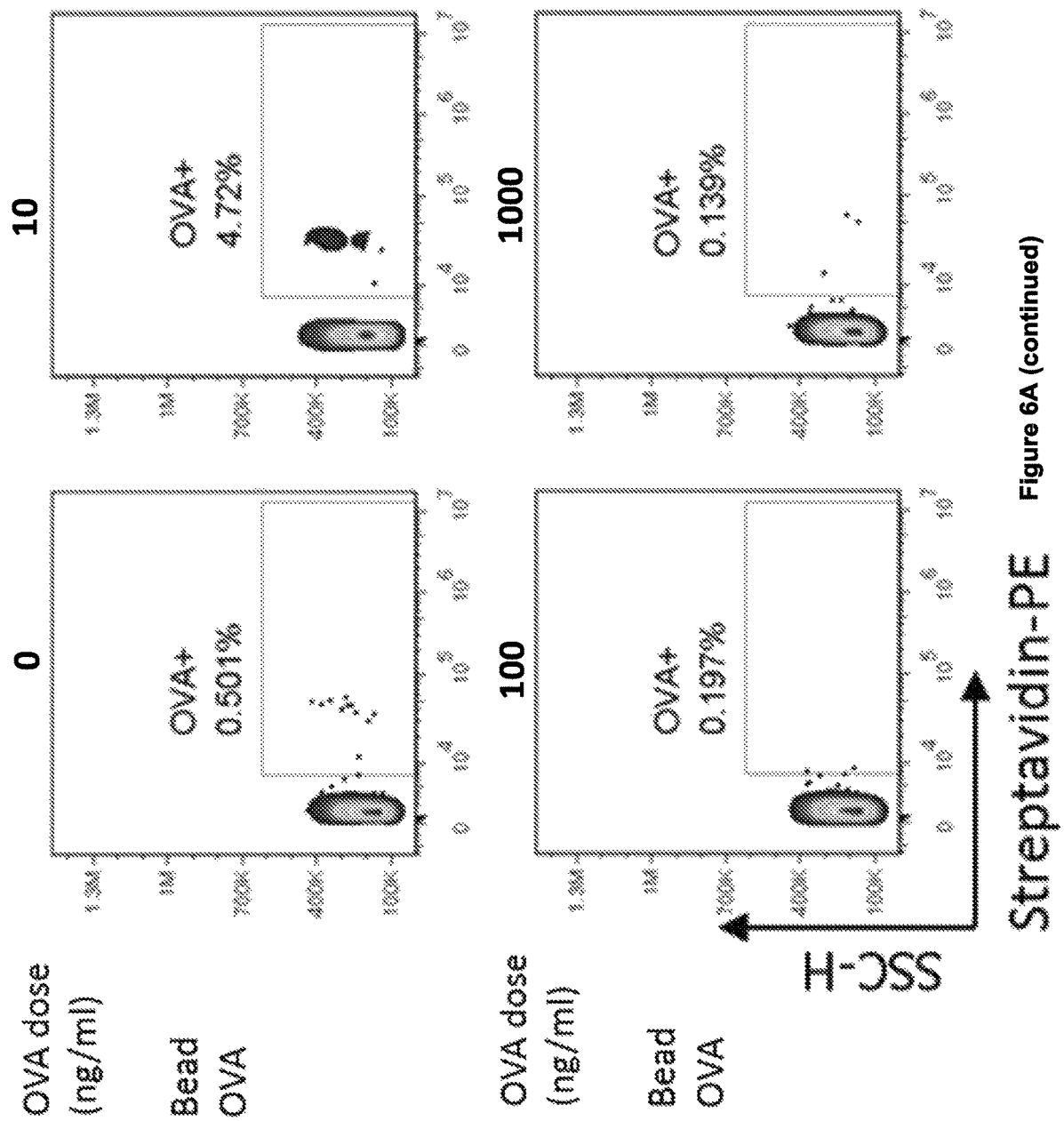
Figure 6B:
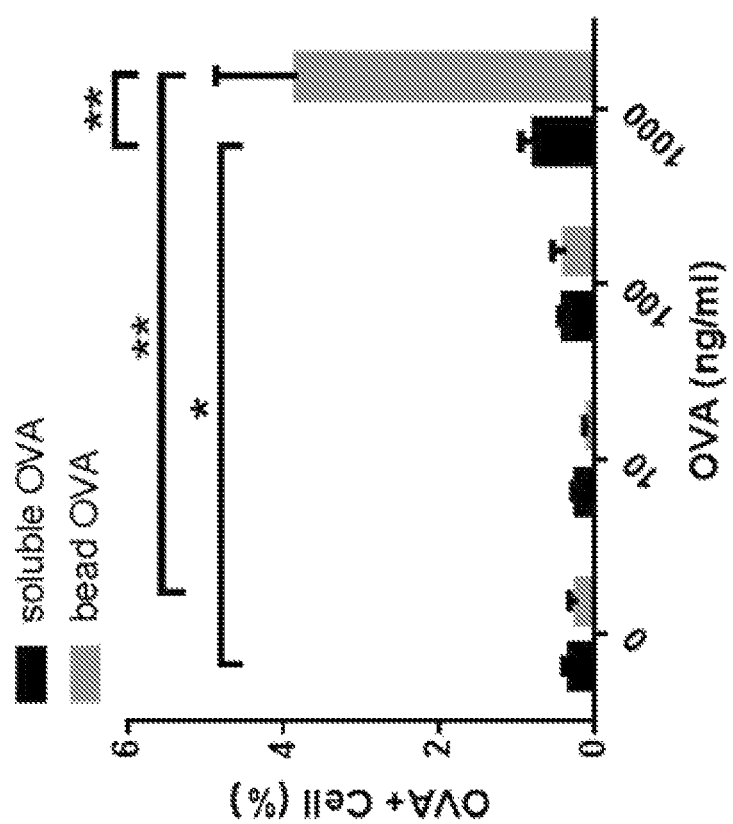

Even though BCRs can directly bind to soluble antigens, B cells in in vivo GC encounter a majority of antigens either as integral components of a membrane or in Fc- or complement receptor-tethered forms on the membrane of follicular dendritic cells (FDCs)[24-26]. Thus, simple artificial FDCs were developed for surface-bound presentation of OVA by incubating streptavidin-coated microbeads with biotinylated OVA molecules. The resulting artificial FDC surface presented OVA molecules in a maximum density of approximately $8.4 \times 10^4$ molecules $\mu m^{-2}$. Neither soluble nor bead-bound OVA brought about a significant increase in the size of OVA-specific population, up to 100 ng ml$^{-1}$, compared to that without using OVA. However, at the maximum dose tested, 1 µg ml$^{-1}$, soluble and bead presentation of OVA yielded 2.4 and 18 times higher OVA-specific populations compared to no-OVA-in-culture conditions, respectively (FIG. 6a). By direct comparison, the bead presentation created ~5 times higher fraction (avg. 3.82%) of OVA-specific cells than the soluble presentation (avg. 0.76%) (FIG. 6b). This data indicates that the antigen-BCR interactions in sGC reaction support the selective survival and/or proliferation of antigen specific B cell populations, and the surface-bound antigen induces stronger support than soluble antigen.

sGC Culture Induced Somatic Hypermutation Leading to a Potential Affinity Maturation.

Figure 7A:
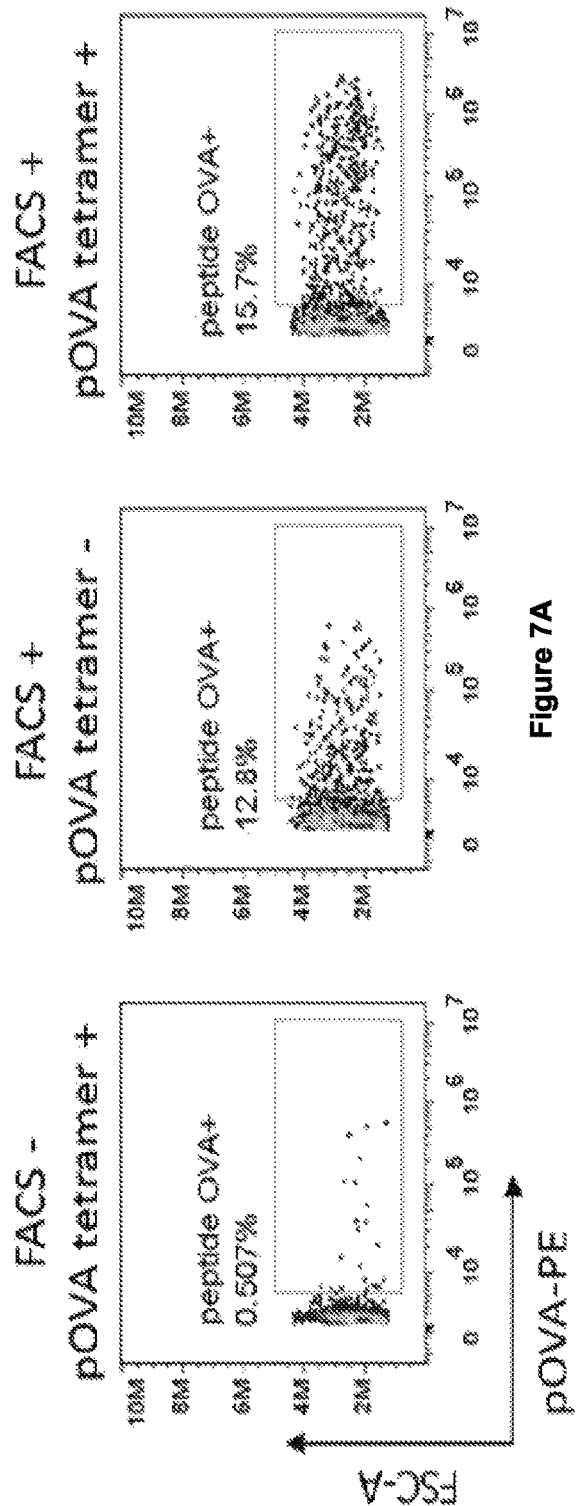

As a critical outcome of GC reactions, B cell containing high-affinity BCRs toward a specific antigen are selectively expanded to become long-lived plasma cells and memory B cells. In GCs, this affinity maturation of B cells is achieved by repeated cycles[27] of cell division and hypermutation of IgV region genes[28,29] under selective pressure toward higher affinity BCRs. In order to test if a similar affinity maturation can be induced during a sGC reaction, it was decided to limit the model antigen to a single epitope, peptide OVA 323-339. Without the FACS enrichment, the pOVA specific population comprised only about 0.2 to about 0.5% of the total B cells after sGC reaction with the concurrent use of pOVA-tetramer in culture (FIG. 7a).

Figure 7B:
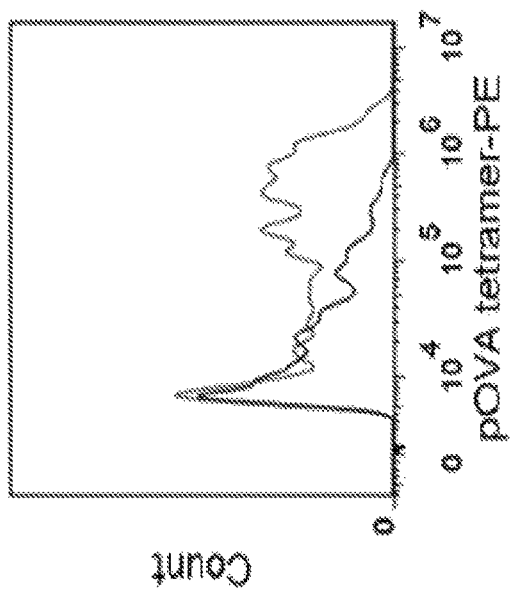

To study the antigen-driven effects, it was decided to enrich the pOVA specific populations by use of FACS before sGC reactions. As shown above, FACS enrichment gave rise to more than 10% of pOVA specific cells after 6 days of sGC cultures. It was intriguing that high-fluorescence staining populations emerged only from the culture with pOVA-tetramer (FIG. 7a, 7b). Notably, the similar emergence of brightly-staining populations was repeatedly observed in every sGC culture using different CD40-ligation methods, i.e., anti-CD40 antibody, soluble CD40L, and bead-bound CD40L, but only in the presence of tetrameric antigens during the culture.

Figure 7C:
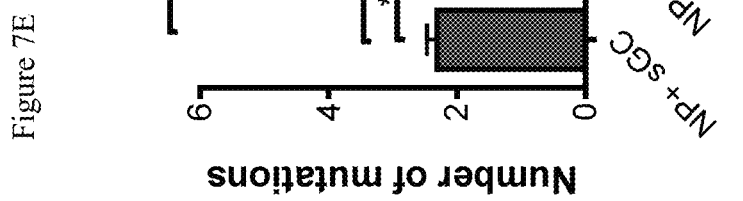
Figure 7D:
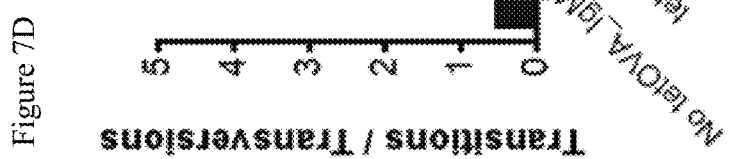
Figure 7E:

Next, a next-generation sequencing technology (454 Sequencing, Roche) was employed to investigate the occurrence of mutations in the heavy chain of resulting BCRs from sGC reactions. For the two pOVA-specific B cell populations harvested from sGC reactions, with or without the tetrameric pOVA during the cultures, a total of 1,644 sequences were acquired, representing 6 different VH gene families and 85 clones with shared CDR3 junctions. For each population, only productive, full-length heavy chain sequences were analyzed. The sequences acquired using forward primer (5' VHE) were analyzed separately from the sequences acquired using reverse primer (3' Cµ). Thus the forward sequencing data represent potentially all isotype classes, while the reverse sequencing data were IgM-specific. Interestingly, when the average number of mutations per sequence were calculated for each dataset, the forward sequencing data from the sGC culture with tetrameric pOVA gave rise to a significantly high number (8.83), compared to the others (forward sequencing data without the antigen (3.31), IgM-specific sequencing data with and without the antigen, 1.65 and 3.19, respectively) (FIG. 7c). This indicates a potential enhancement in mutations among the isotype-switched B cells in the presence of multimeric antigens. In a further analysis to calculate the ratio of total number of transition mutations (exchange of a purine for a purine or of a pyrimidine for a pyrimidine) to transversion mutations (exchange of a purine for a pyrimidine or vice versa) in each dataset, transitions were much more favored over transversions only in the forward sequencing data acquired from the B cells cultured with tetrameric pOVA (FIG. 7d). This data strongly suggest that the higher number of mutations observed in this dataset is likely due to the somatic hypermutation (SHM) triggered by activation-induced deaminase (AID)[30]. To verify these findings further, a similar experiment was performed using a second antigen, hapten 4-Hydroxy-3-nitrophenylacetyl (NP)-specific B cells. The sGC B cells were also compared to bone-marrow isolated pre-B cells as well as the natural GC B cells isolated from the spleen, 2 weeks after vaccination with $NP_{45}CGG$. From the NP-specific sGC B cells and natural GC B cells, a total of 711 productive, full-length heavy chain sequences were acquired. As expected, the average number of mutations per sequence calculated for the NP-specific sGC B cells cultured in the presence of $NP_{45}CGG$ (2.45) is higher than the average number for sGC B cells cultured without the antigen during culture (1.81) or the average from the Pre-B cell population (1.06), while the average number of mutations found in the natural GC B cells was the highest (4.75) (FIG. 7e).

When the ratio of transitions to transversions was examined in each dataset, transition mutations were favored over transversion mutations in both sGC B cell samples as well as in natural GC B cells, while the detected mutations in the Pre-B cell sample were quite randomly distributed and were more than likely simply sequencing artifacts (FIG. 7f). These data demonstrated that AID-assisted SHM are occurring in the sGC culture conditions, and the mutation rate is potentially enhanced by the presence of multimeric antigens. An intrinsic molecular mechanism of the physiological AID-assisted SHM favors mutations of regions of IgV genes that are implicated in antigen binding (complementarity determining regions, CDRs) compared to structurally important framework (FR) residues[30], which with other mechanisms selectively accumulate mutations that induce amino acid replacements (R) compared to silent (S) mutations in the CDRs of antigen-selected germinal center B cells[31]. Interestingly, it was found that replacement mutations accumulated within CDRs of the NP-specific sGC B cells and natural GC B cells, while no such accumulation of replacement mutations in CDRs of Pre-B cells was detected (FIG. 7g).

Figure 15:
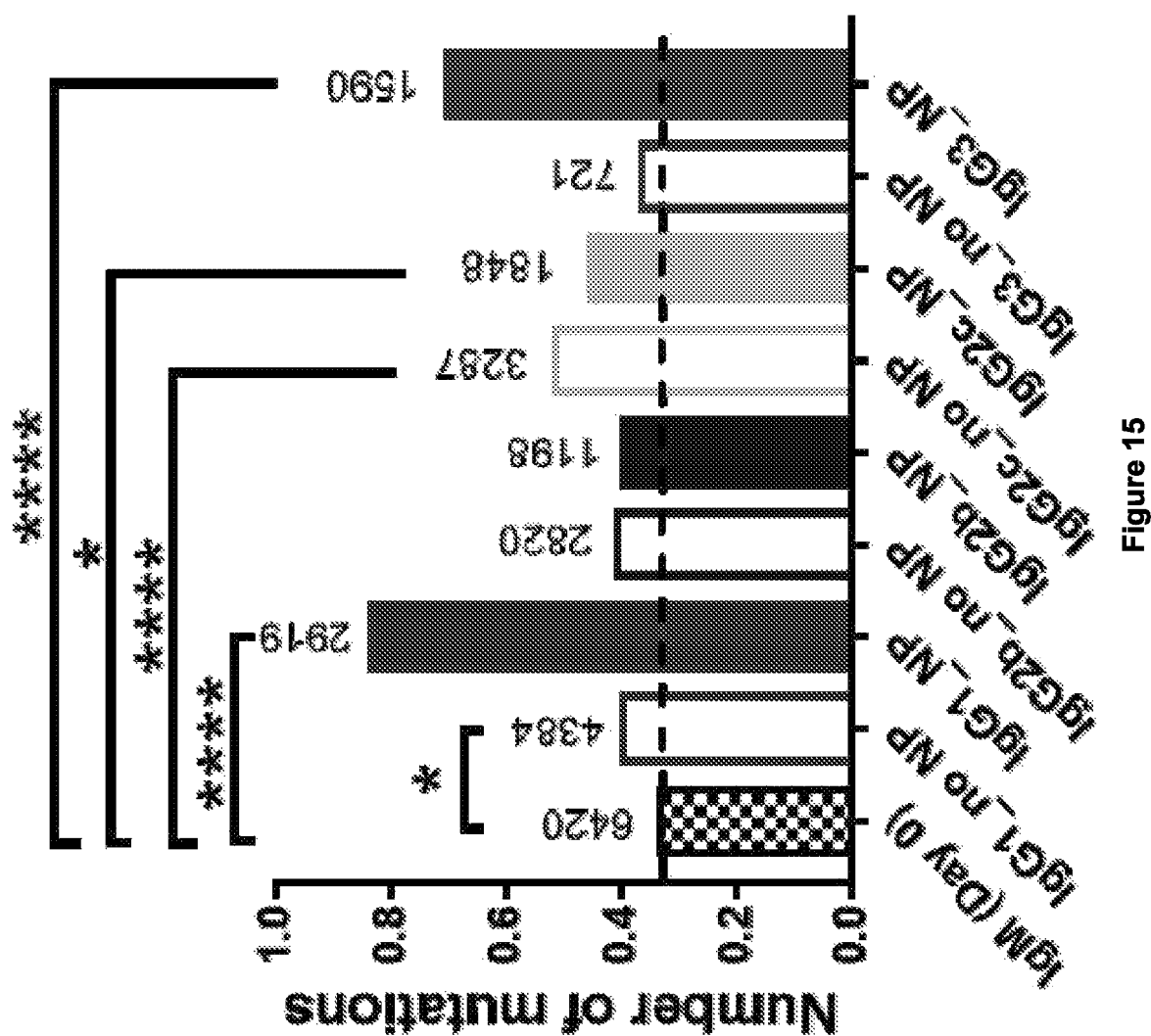
FIG. 15. Number of mutations per IgHV 186.2 sequence from B1-8 mouse B cells. Number of mutations within IgM chains (Day 0, check-filled bar) is compared with the values acquired from IgG chains after 6-day sGC culture. The empty and filled bar graphs represent the sequences acquired from the sGC cultures either in the absence of antigen (no NP) or in the presence of bead-presented NP-BSA (NP), respectively. The numbers on top of each bar graph denote the number of full-length IgV chain sequences employed for the analysis. Statistical significance from ordinary one-way ANOVA followed by Tukey's multiple comparisons test were represented as * ($p<0.05$) and **** ($p<0.0001$).

Even though it is unlikely, there remained a nominal possibility that the mutations found in isotype-switched IgGs came from the expansion of B cell clones that originally had possessed physiologically induced mutations (before Day 0 of sGC culture). In order to evaluate whether the ex vivo ligation of CD40L induced new mutations during sGC cultures, a B1-8 mouse model was employed, where a knock-in IgHV186.2 (IgV1-72) gene segment produces NP-specific antibody when paired with λ1 light chains. By employing FACS-sorted λ1+ B1-8 B cells, a large number of B cells that originated from the single germ-line IgHV gene sequence could be analyzed. As the investigators could not isolate detectable mRNAs of IgGs from the naïve B cells directly isolated from B1-8 mice (8-12 week old, non-vaccinated, kept under a pathogen-free condition), IgM sequences of naïve B cells were first analyzed as the starting population on Day 0 and compared with sequences acquired from newly generated IgG chains on Day 6 of sGC culture. It was consistent that the average number of mutations per sequence observed in IgG chains is consistently higher than the number acquired form IgM chains (FIG. 15). Among 6420 analyzed full-length sequences of IgM, 937 were detected to contain a limited number of mutations (mostly 1 mutation per sequence). Clonal tree analyses generated a wide, but very shallow clonal tree, which indicates that these detected mutations in IgM sequences on Day 0 were random and possibly sequencing/PCR errors (FIG. 8). Compared to this, among 2919 analyzed IgG1 sequences isolated from Day 6 of sGC B cells, 640 contained multiple numbers of mutations, and the clonal tree also clearly demonstrated many sub-lineages with an accumulation of mutations (FIG. 8). The same trend from the sequences of other IgG isotypes (IgG2a, IgG2b, and IgG3) was observed.

Altogether, these results indicate that sGC cultures clearly can induce a higher frequency of mutations in the Ig V region, mimicking the AID-targeted SHM that occurs in the physiological GCs, from which high affinity B cell populations can emerge when cultured with presentation of multimeric epitopes.

Adoptively Transferred sGC B Cells Engrafted in the Secondary Lymphoid Organs, Maintaining their Centrocyte or Memory B Phenotypes.

Figure 9A:
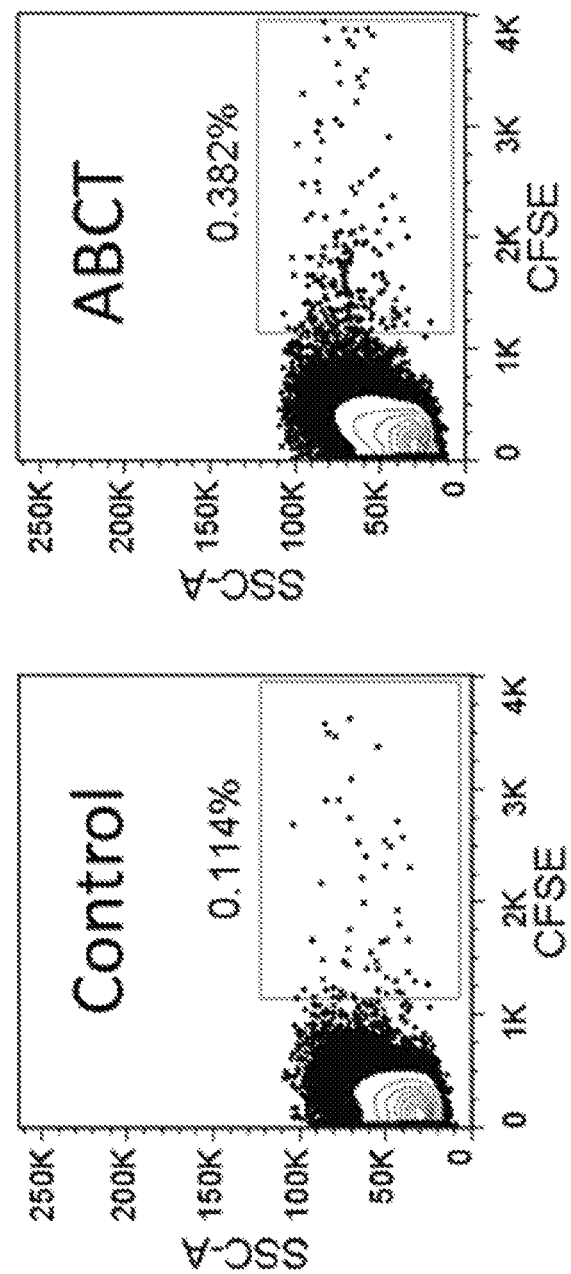
Figure 9D:
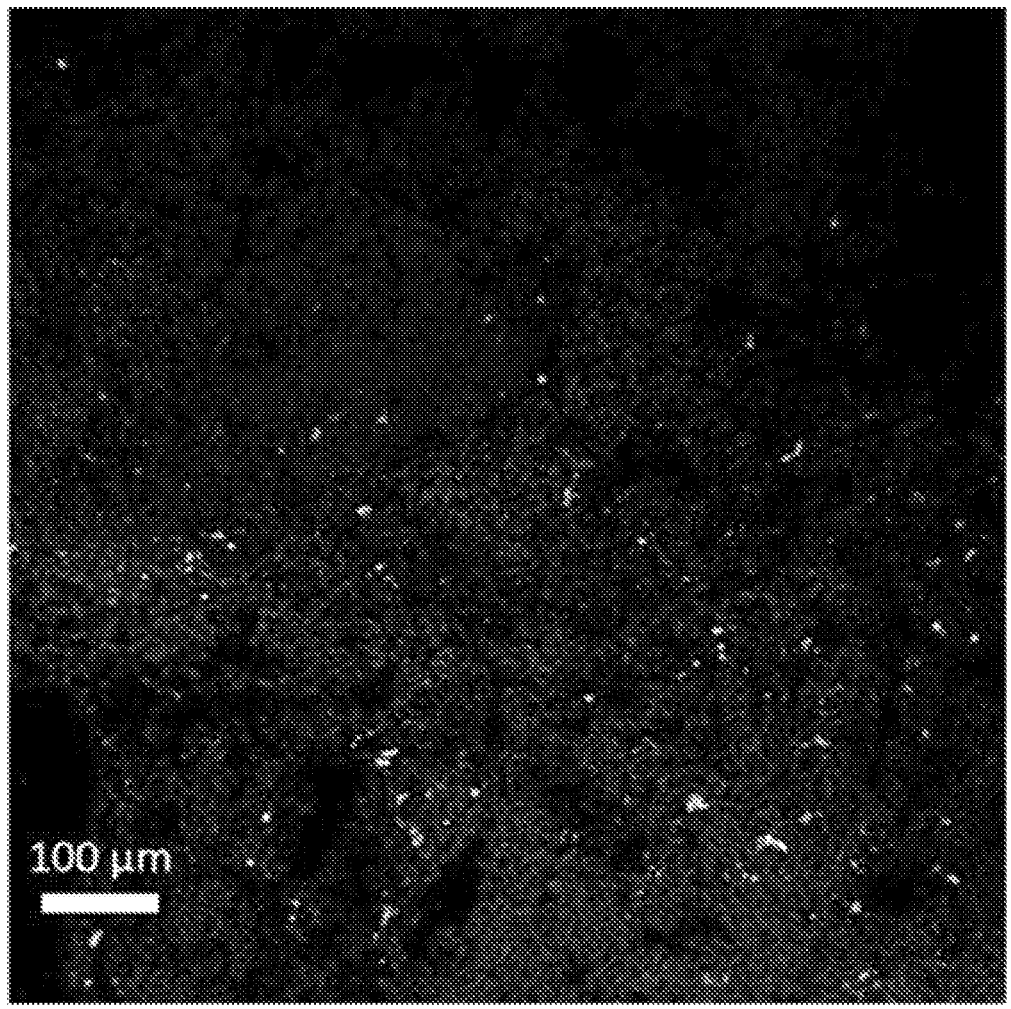

If the B cells generated from the described sGC reaction can be adoptively transferred, such method could potentially serve as a novel autologous cell therapy regimen for the induction of long-term antigen-specific humoral immunity. In order to test the feasibility of this method, approximately $1 \times 10^7$ CFSE-loaded B cells were adoptively transferred from a 6-day sGC culture into non-irradiated syngeneic mice. The spleen and lymph nodes were harvested 4 days after the adoptive B cell transfer (ABCT). In flow cytometry analyses, both the spleen and the pooled lymph nodes harvested from the mice after ABCT contained higher number of CFSE-positive cells compared to the control mice without the ABCT (FIG. 9a-9b). Further, these CD19+ CFSE+ double positive donor B cells expressed IgG1, CD80 (B7.1), and Fas, which were not expressed in the majority of CD19+CFSE− recipient mouse B cells (FIG. 9c). When lymph nodes harvested 4 days after ABCT were examined using immunofluorescence microscopy, the CFSE+ cells were scattered throughout the perifollicular regions, B-cell zone as well as some in the T-cell zone (FIG. 9d).

Figure 9E:
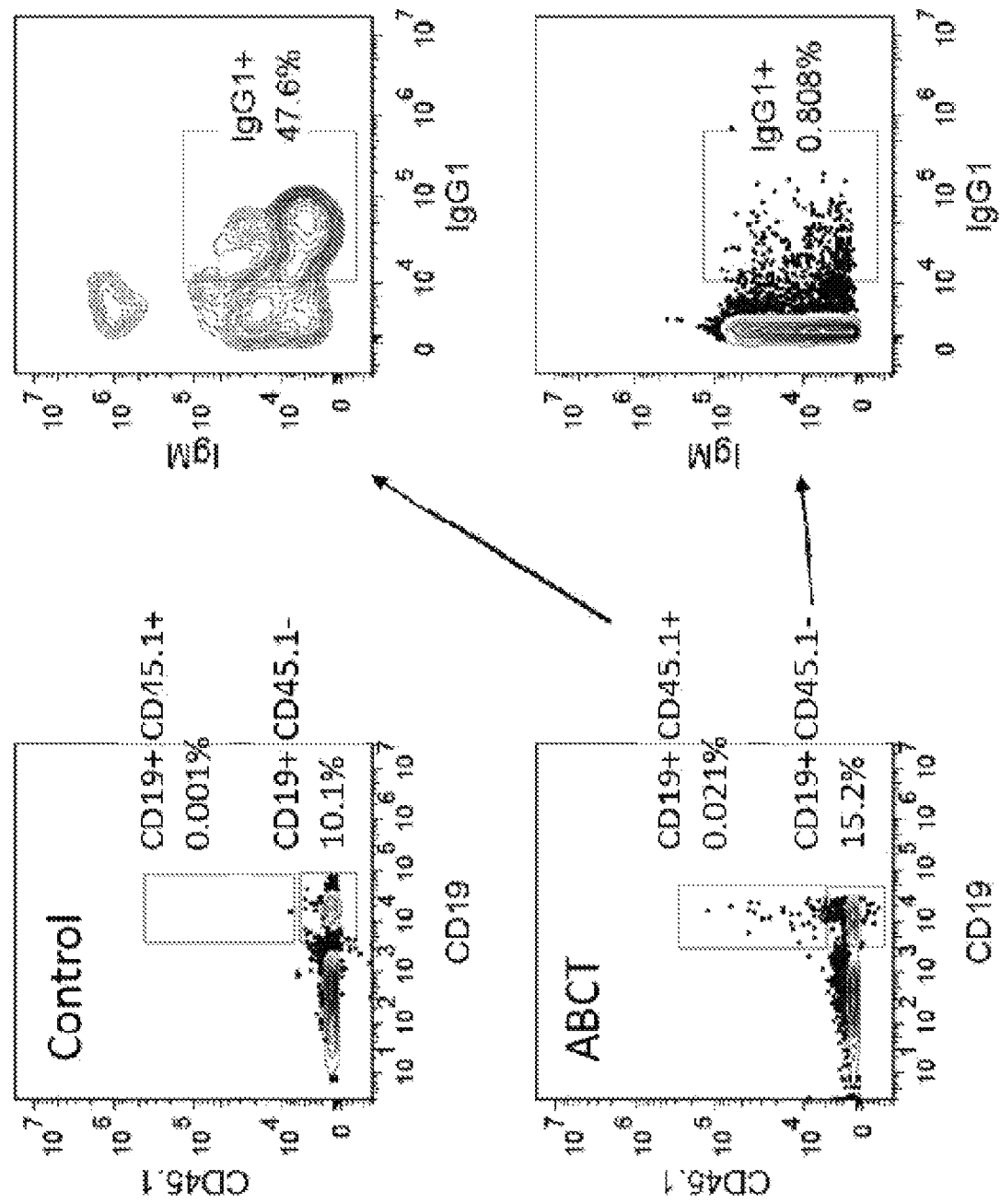
Figure 9F:
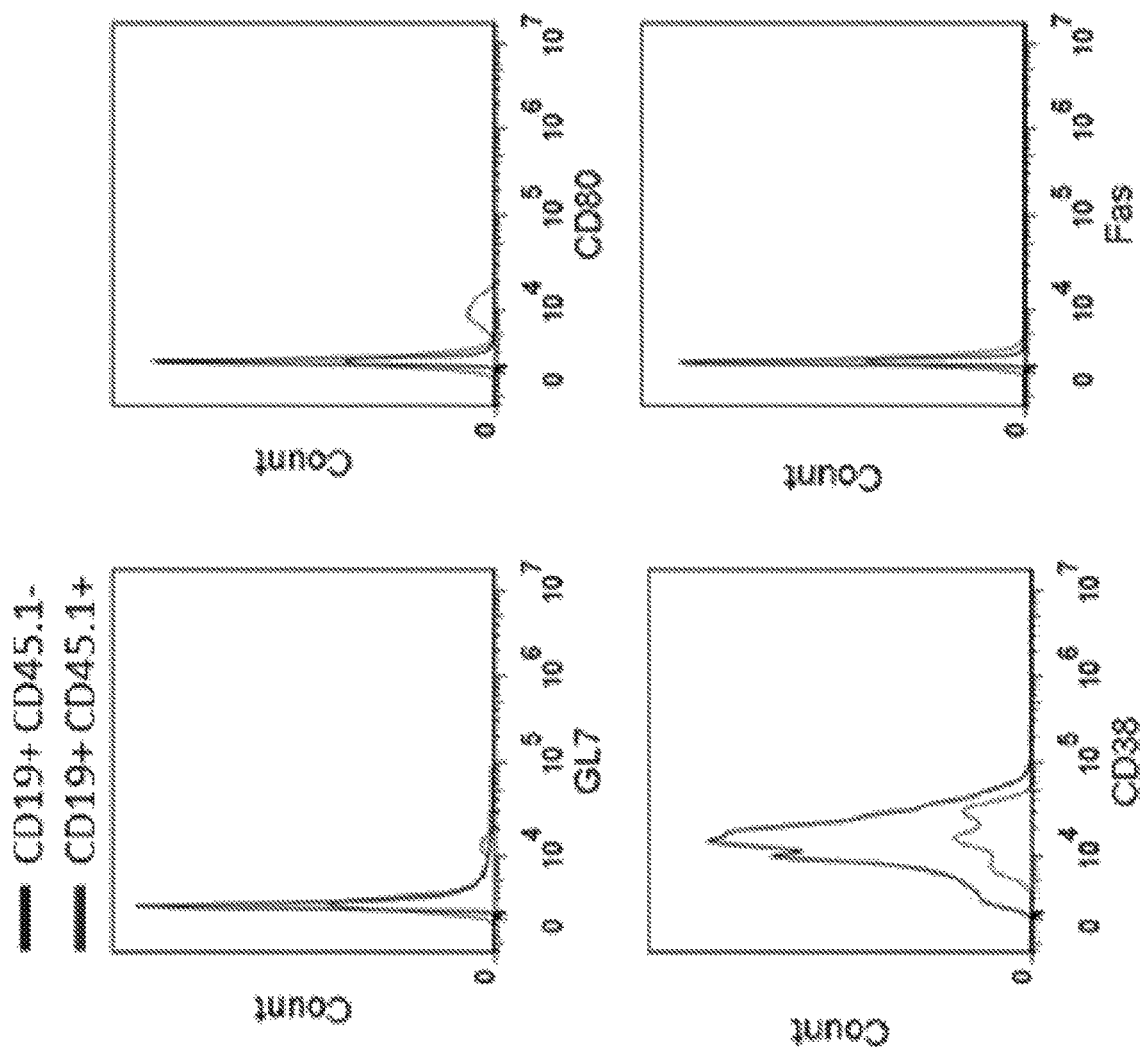
Figure 10:
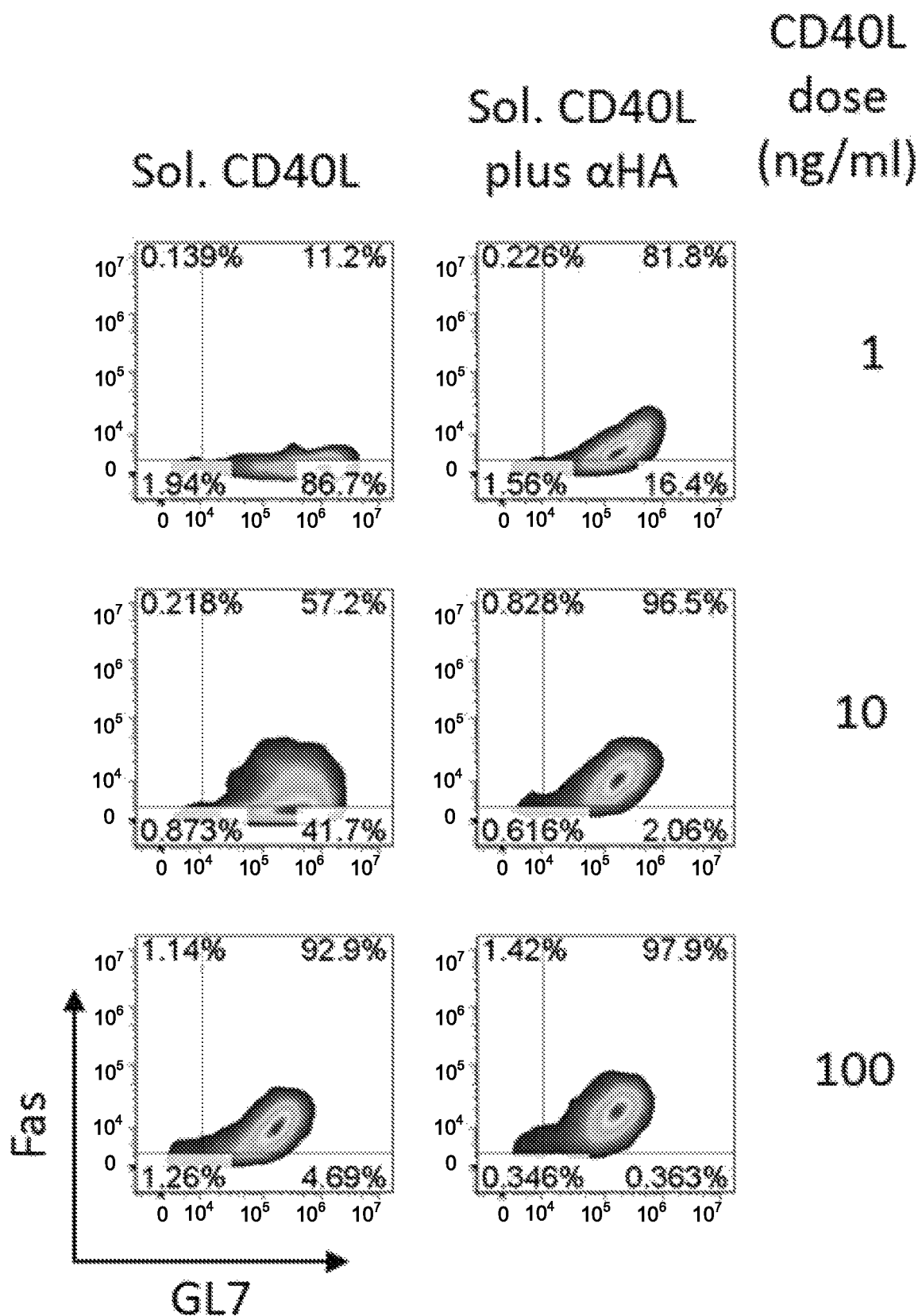
FIG. 10. Flow cytometry analysis to examine expression level of GL7 and Fas genes on B cells after 6-day culture in each indicated condition. Numbers indicate the percentages of cells in the respective quadrants. The GL7+Fas+ B cell populations are regarded as GC-like B cells, and their percentages were plotted in FIG. 3g.
Figure 10:
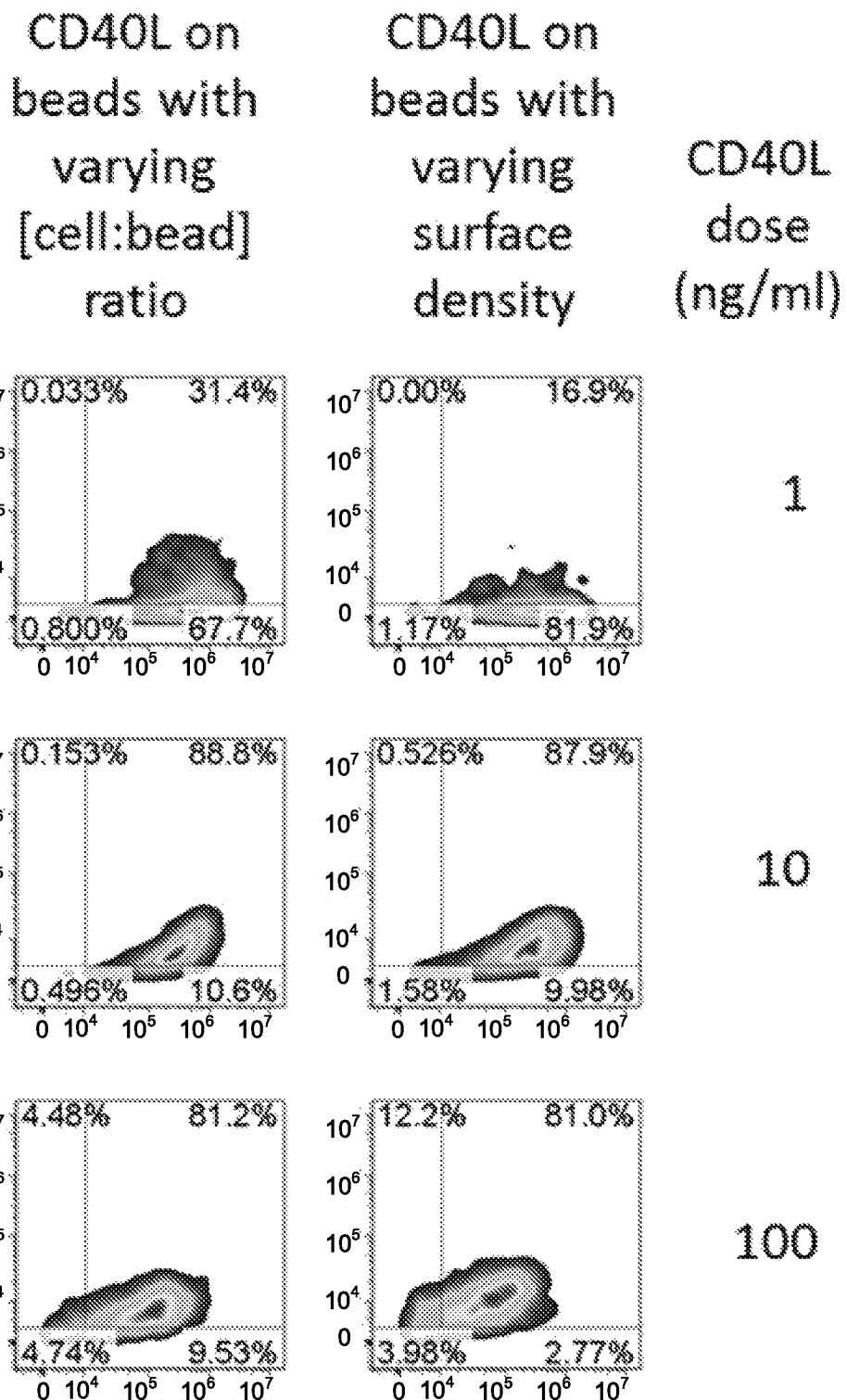
Figure 11:
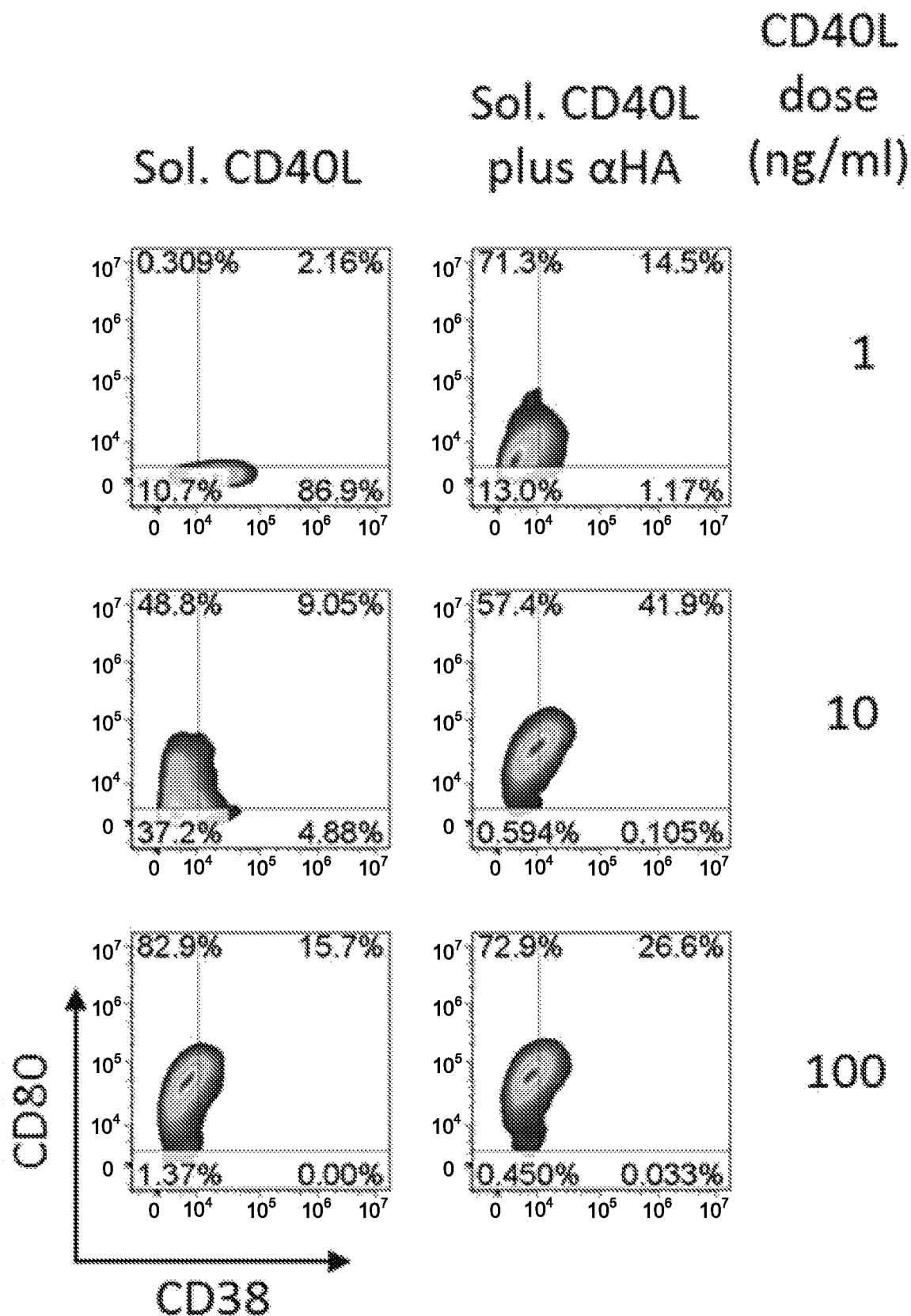
FIG. 11. Flow cytometry analysis to examine expression level of CD38 and CD80 genes on B cells after 6-day culture in each indicated condition. Numbers indicate the percentages of cells in the respective quadrants. The CD38-CD80+ B cell populations are regarded as GC-like B cells, and their percentages were plotted in FIG. 3h.
Figure 11:
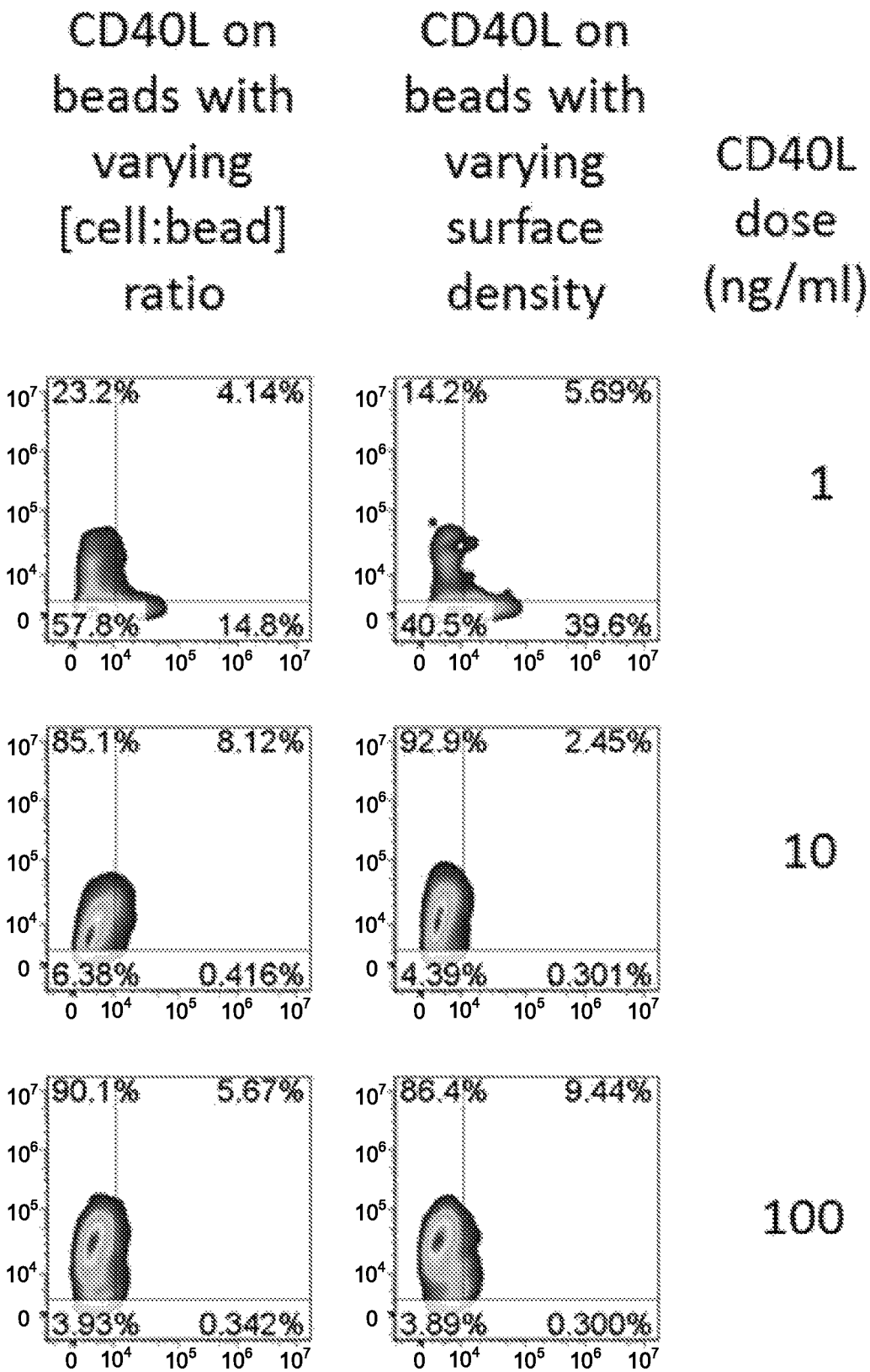

In order to track the adoptively transferred sGC B cells for a longer period, sGC B cells were generated expressing genetic marker (CD45.1+) and transferred them into non-lethally irradiated (6.5 Gy) congenic host mice intravenously. After 4 weeks, donor-derived B cells (CD45.1+ CD19+) were evidently detected both in the spleen and in the lymph nodes (FIG. 9e). Compared to the low percentage of IgG1+ populations in the recipient B cells, about half of the donor B cells were IgG1+(FIG. 9e). However, the distinctive expression levels of GC B cell makers, GL7, CD80, CD38, and Fas, which were maintained in the donor B cells for at least 4 days, had mostly disappeared by 4 weeks after ABCT to be very similar to the expression levels of naïve B cells from the recipient mice (FIG. 9f). These results suggest that the B cells cultured in sGC conditions can be adoptively transferred in during an autologous cell therapy to successfully engraft in the secondary lymphoid organs within short periods without losing their GC phenotype, and also survive long periods as latent B cells.

DISCUSSION

Previously, engagement of CD40 molecules on B cells using soluble anti-CD40 or CD40L were widely used to activate B cells without comprehensive studies on their potential usage in artificial GC reactions. Here, it was found that both of these approaches were only partially effective in recapitulating the GC reaction, i.e., the anti-CD40 antibody can induce isotype class switching in the activated B cells with minimal cell expansion and minimal expression of GC B cell phenotypes, while soluble CD40L enabled quite effective expansion and differentiation into GC-like B cells but only with minimal isotype class switching. In fact, CD40 engagement in B cells induces various biological outcomes including survival of B cells, expression and down-regulation of various surface proteins, production of numerous cytokines and chemokines, in addition to promoting germinal center formation[34], which are achieved by activation of multiple pathways including NF-κB, MAPK, and STAT3[35]. Multiple factors mediate these complex activation pathways by direct or indirect interactions with CD40 molecules[36,37], and it is likely that different methods of engagement for CD40 might induce an equal variety of gene expression profiles. In vivo, CD40L is expressed as a homotrimer on plasma membrane[2,38], and it was shown that clustering of membrane-bound CD40L molecules is necessary for CD40-mediacated B cell activation[39]. However, the 18 kDa soluble form of CD40L (which also naturally arises from proteolytic processing), as well as all of monomeric, dimeric and trimeric forms of soluble CD40L, bind to CD40 molecules on the B cell membrane and activate the B cells at a certain level.[4,40]

The described system of modifying microbeads with CD40L in a defined and controllable molecular density, mimicking $T_H$ cells, is a rational approach to controlling the quality and quantity of CD40-mediated B cell activation. The results herein demonstrate that varying doses of CD40L on artificial $T_H$ cells can effectively modulate the proliferation of B cells, CSR, and the expression of GC B cell phenotypes. Some optimal conditions to induce all of these canonical GC functions ex vivo have also been successfully determined. Together with RT-PCR analysis, it is demonstrated herein that this sGC reaction activates B cells to differentiate into the rapidly proliferating cytoblast-like cells in the initial phase, and then quickly differentiate into the centrocyte-like B cells in which downregulation of BCL6 initiates various signaling pathways[20]. As early as 3 days following sGC culture, a significant transcriptional upregulation of AICDA, which induces CSR and SHM, is observed. At this point, a small fraction of sGC centrocytes start committing into the plasma cell lineage (CD138+) with a transcriptional upregulation of PRDM1, which is enhanced by switching the cytokine environment from IL-4 to IL-21[21]. Notably, suppression of apoptosis by BCL6 is rapidly reduced in the sGC culture. Therefore, a novel culture strategy where antigen-presentation occurs for an optimal period of the centroblast stage for an extended survival and expansion, followed by provision of artificial $T_{FH}$ signals for induction of centrocyte stage, or even where these stepwise reactions are alternated, could be encompassed herein. In the same vein, artificial presentation of other molecular signals that are present in the immunological synapse between B cell and T cell such as adhesion, co-stimulatory, and accessory receptors and ligands[41] can be utilized in the described methods for better induction and maintenance of in vitro GC reactions.

In order to examine, recapitulate, and leverage the generation of antigen-specific B cells, a critical attribute of GC reactions, ex vivo, fluorochrome-conjugated multimers of whole protein model antigen OVA as well as a single B cell epitope peptide of OVA were used for detection and isolation of B cell populations with the corresponding BCR specificity[42-46] using flow cytometry. Using the described sGC reaction in conjunction with an isolation of antigen-specific B cells by FACS, highly enriched antigen-specific GC-like B cells were able to be routinely generated.

Without an extraneous enrichment step, simply including the soluble antigen in the sGC culture enhanced the fraction of antigen-specific B cell populations in a dose dependent manner. A more pronounced enhancement in the fraction of antigen-specific B cell population was achieved by providing the antigen in a surface-bound form on microbeads. In the described sGC reaction, CD40L and BAFF are provided in a nonselective manner regardless of the B cells' affinity toward the model antigen. Thus, this observed enhancement of a selective population of antigen-specific B cells is most likely due to the additional survival and proliferative signals provided by BCR-antigen interaction, which effectively mimic the selective survival and proliferation of GC B cells upon binding of their BCRs to antigen presented by FDCs[47,48]. As the concentration of antigen required for triggering effective BCR signaling is inversely proportional to the affinity toward the antigen[49], the observed antigen-dose-dependent increase of antigen-specific B cells might be due to the BCR-dependent activation of lower affinity B cells with an increasing amount of antigen up to a certain threshold.

Moreover, it is intriguing that a B cell population that is highly stained with pOVA tetramers was repeatedly observed to emerge in flow cytometry only when FACS-enriched antigen specific B cells were cultured in sGC conditions with pOVA tetramer in the culture. This brighter fluorescence could be due to either expression of higher number or BCRs or increased BCR affinity. While there is no simple explanation for the higher expression of BCRs in these centrocyte-like B cells, there are feasible mechanisms for the emergence of B cell populations with higher affinity BCRs. First, this could be the result of advantageous signals for survival and proliferation provided by BCR-antigen interactions to the high affinity B cell clones. Above, the same rationale was applied to account for the selective increase in antigen specific populations after sGC reactions in the presence of antigen even without the FACS enrichment step. The FACS enrichment step prior to the sGC culture simply made the selective increase in higher affinity B cells more visible. In this scenario, the presence of tetrameric epitope was essential to induce BCR-antigen affinity-dependent survival/proliferation signaling. Alternatively, the increase in BCR affinity toward the antigen could also be introduced to the antigen-specific B cell populations as a result of somatic hypermutation (SHM) of the immunoglobulin (Ig) genes. In the GC, affinity maturation of the antibody responses is enabled by SHM of the variable regions of immunoglobulin genes[50,51] and subsequent selection of higher-affinity B cell clones[52]. Similarly to CSR, SHM is known to be driven by AID (AICDA), which is largely expressed in GC B cells[14-16]. As previously described, RT-PCR analysis confirmed that AICDA mRNA expression is highly upregulated in the described sGC culture, even higher than in the natural GC B cells. Further, it was previously reported that SHM can be induced in vitro when the surface BCRs are cross-linked in the presence of help from cognate T cells[53,54]. From the high-throughput sequencing analyses for the V region gene of peptide-OVA-positive B cell clones as shown herein, B cells emerging from sGC reactions with the addition of tetrameric peptide OVA epitope showed a significantly higher number of mutations within their potentially isotype-switched Ig heavy chains. Among the increased number of mutations, transition mutations were much more favored over the transversion mutations, mimicking AID-initiated physiological SHMs[30]. An equivalent result was acquired from the sequencing of NP-positive sGC B cells. Compared to the pre-B cell control group in which the observed mutations might dominantly originate from spontaneous random mutations or other sequencing errors, lacking active SHM present, NP-specific sGC B cells showed higher number of mutations per sequence, with transitions favored over transversions.

Interestingly, a similar enhancement of mutations was observed within the NP-specific sGC B cells cultured in the absence of NP-CGG, even though the enhancement of mutations was slightly lower than the sGC B cells cultured in the presence of antigen. Whether this observation is due to the effect of residual NP-BSA-biotin labeling in the initial FACS step, or due to the BCR cross-reactivity of NP-specific B cells to the bovine serum proteins in the culture media, or to another cause, is unclear at this point. Nevertheless, in further analyses of the distribution of mutations, the described sGC B cells as well as the natural GC B cells show an increase in replacement mutations (those that alter the amino acid sequence) in the complementarity determining regions (CDRs) over those found in the frameworks (FRs), a hallmark of antigen-driven selection. In the present sGC model, artificial T-cell help signals are universally provided, thus this selection of higher affinity B cells is most likely not due to the competition in uptake of antigen for better presentation to the T cells[10]. Instead, the BCR-antigen interaction could provide not only selective signals for better proliferation and survival but could also enhance the number of mutations in Ig genes, which also positively correlates to the number of cell division. By analyzing mutation patterns of large number of B cells that share a common germline IgHV gene sequence IgHV 186.2, it is demonstrated herein that the mutations detected within the isotype-switched IgV chains are the mutations that are newly acquired and accumulated during the ex vivo culture, regardless of presence of antigen (FIG. 8).

Lastly, the clonal lineage trees formulated from peptide-OVA and NP-specific sequences show no more than 5 generations of accumulated mutations, and the majority of mutated sequences are within 3 generations from the germline sequences (FIGS. 8 and 16). This analysis agrees well with the fact that sGC B cells have lower number of mutations per sequence than natural sGC B cells. The majority of the described sGC B cells may only be given a chance to undergo a small number of cell divisions before they are subject to apoptosis once they enter a centrocyte-like stage. Therefore, the method may comprise additional steps for improvement to better support survival and increasing rounds of cell division for the antigen-selected sGC B cell populations.

Recently, cellular immunotherapies such as the adoptive transfer of antigen-specific T cells have been actively pursued for treatment of viral infections and multiple cancers including relapsed hematologic malignancies. CD40-activated B cells have been proposed either as effective antigen presenting cells (APCs) to augment T cell immunotherapies[55-57] or themselves as effector cells in cancer adoptive immunotherapies[8,57,58]. It was encouraging to observe that the resulting B cells from the described sGC reaction had migrated to and engrafted within the secondary lymphoid organs upon adoptive transfer into the non-irradiated syngeneic and non-lethally irradiated congenic host mice. Further, the isotype-switched donor B cells maintained Fas+ and CD80[hi] GC B cell phenotypes for a short period (~1 week), and survived for a long term (at least up to the tested period of 4 weeks) as latent B cells. Altogether, the described sGC cultured antigen-specific B cells show a tremendous potential as an alternative or an adjunct immunotherapy regimen to the costly development of monoclonal antibody drugs and T cell adoptive therapies against cancers and infections[59,60] for which no effective treatments are currently available.

Methods.

Mice and Isolation of Naïve B Cells.

Figure 17:
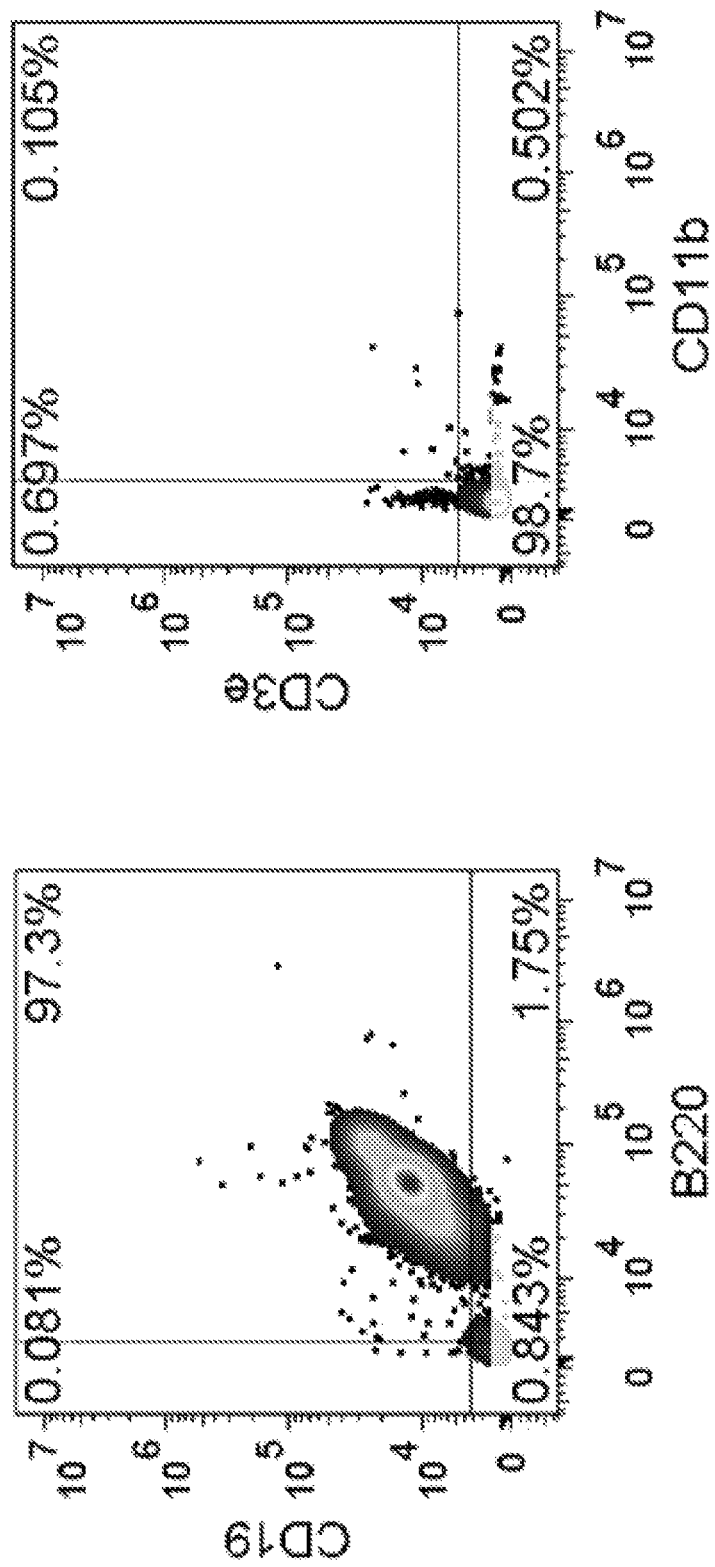
FIG. 17. Composition of the initial cell populations after MACS B cell isolation applied for RBC-depleted splenocytes. Shown are the representative flow cytometry data from at least 5 independent experiments. Majority (>97%) is B cells (CD19+ B220+) with a minimal contamination (<1%) with T cells (CD3e) and CD11b+ cells.

All experiments were performed using the B cells isolated from 8-12 week old C57BL/6J or C57BL/6-CD45.1 (B6.SJL-Ptprc$^a$ Pepc$^b$/BoyJ) mice purchased from the Jackson Laboratory (ME, USA). B1-8 mice were originally received from Dr. Garnett Kelsoe (Duke University), and have been inbred by the Jacob lab. All mice were maintained in the Georgia Institute of Technology or Emory University (B1-8) animal facility under pathogen-free conditions. Procedures involving mouse were under protocols approved by the IACUC of the Georgia Institute of Technology. From the spleen, single-cell suspensions of white blood cells were prepared by simply pushing the spleen through a 40 micron cell strainer (Falcon) and incubation in ammonium chloride RBC lysis buffer (eBioscience). For the PBMC, blood was drawn by cardiac puncture from a sacrificed mouse and directly diluted in PBS with 2 mM EDTA. The PBMC were collected from the interfacial layer after a density-gradient centrifugation using Histopaque (Sigma). From these single cell suspensions, naïve B cells were further purified using a negative magnetic sorting (B cell isolation kit, Miltenyi). After depletion of cells labelled with monoclonal antibodies against CD43, CD4, and Ter-119, the resulting cell suspension typically consist of more than 97% of B cells (FIG. 17).

sGC Cell Culture.

In a typical sGC cell culture, purified naïve B cells ($10^5$ cells per well) were cultured in a 24-well tissue culture plate (Corning) in RPMI-1640 medium (Gibco) supplemented with 10% FBS (Sigma), 1 mM sodium pyruvate, 10 mM HEPES, $5.5 \times 10^{-5}$ M β-ME, 100 units ml$^{-1}$ penicillin, and 100 μg ml$^{-1}$ streptomycin (Gibco). Murine recombinant IL-4 (20 ng ml$^{-1}$, Peptrotech) and BAFF (50 ng ml$^{-1}$, R&D Systems) were added in the initial culture medium and supplemented in every 2-3 days. For sGC_421 culture, IL-4 was replaced by murine recombinant IL-21 (10 ng ml$^{-1}$, Peptrotech) on day 3. The CD40-CD40L ligation conditions and addition of model antigens were varied as specified in the text. For the initial comparative test for soluble CD40L vs. anti-CD40 antibody, CD40L (E61-L260, R&D Systems) or anti-CD40 antibody (clone 1C10, eBioscience) was used at 1 μg ml$^{-1}$. For the direct comparison between soluble CD40L and microbead-bound CD40L, recombinant murine CD40L (M112-L260; SEQ ID NO: 18) with N-terminal HA tag (YPYDVPDYA (SEQ ID NO: 2) was employed. For the crosslinking of soluble CD40L, mouse anti-HA peptide antibody (clone 543851, R&D Systems) was added at 1 μg ml$^{-1}$. The microbeads with surface-bound CD40L molecules (SEQ ID NO: 19) were prepared as artificial $T_{FH}$ cells freshly, not more than 3 hours before initial application to sGC cell culture. Superparamagnetic microbeads (diameter of 1 μm) with covalently attached anti-HA peptide antibody (Pierce) were washed by repeating magnetic precipitation (DynaMag, Invitrogen) and resuspension in fresh PBS for at least 3 times, before incubation with CD40L molecules for 2 hours at 4° C. under rotation. For the exact control for surface density of CD40L, the binding capacity of CD40L molecules to microbeads was determined by measuring protein concentration (absorbance at 280 nm) of supernatant before and after incubation with microbeads. The dose of microbead-bound CD40L was controlled as specified in the main text for the direct comparison to the equivalent dose of soluble CD40L. In all the other subsequent sGC cultures, microbeads were employed as artificial $T_{FH}$ cells with surface density of approximately $5 \times 10^3$ $\mu m^{-2}$ and maintained for the cell to beads ratio of 1:10~1:50, unless otherwise specified. The live B cell number was counted using hemocytometer with trypan blue dye exclusion. All cultures were performed in a humidified atmosphere at 37° C. with 5% $CO_2$.

Flow Cytometry and FACS.

Cells suspended in PBS supplemented with 0.5% (w/v) BSA and 2 mM EDTA were incubated with anti-CD16/CD32 monoclonal antibody (clone 93, eBioscience) and simultaneously stained with combinations of the following antibodies: FITC-, PE-, PE-Cy7, or APC-conjugated anti-mouse CD19, IgM, IgE, IgG1, CD45R (B220), CD80 (B7.1), CD138, CD3c, CD11b, GL7 (Ly77), CD38, and CD95 (Fas) (eBioscience). Typically, 0.1 to 0.5 µg of antibody was used for staining of approximately $10^5$~$10^7$ cells in 100 µl. For the control staining experiment for OVA-specific B cells, the cells were first incubated with OVA (1 µg ml$^{-1}$), washed two times, and stained with FITC-conjugated rabbit polyclonal anti-OVA antibody (Abcam). The live cells were gated out from the dead cells and the microbeads based on FSC versus SSC. The positive gating was made based on the negative and/or isotype staining controls. All samples were analyzed using a Accuri C6 or LSR II (BD Biosciences), and fluorescence-activated cell sorting (FACS) was performed using FACSAria III cell sorter (BD Biosciences). The data were analyzed suing FlowJo software.

Detection and Enrichment of Antigen-Specific B Cells.

The model antigen protein OVA (Hyglos) was biotinylated using reaction with sulfo-NHS-LC-biotin (Pierce), followed by purification (Zeba spin desalting columns with 7000 MWCO, Pierce) and lyophilization. Using HABA assay (Pierce), the level of biotin incorporation was measured and the number of biotin per modified OVA molecule was determined to be 2.65. For the detection and FACS of OVA-specific B cells, multimeric OVA was freshly prepared by incubation of biotinylated OVA with PE- or APC-conjugated streptavidin in 4:1 molar ratio for 30 min at 4° C. The incubated protein mixture was directly added into cell suspensions for the flow cytometry at 1~10 µg ml$^{-1}$ per $10^6$ cells. For the preparation of microbeads with surface-bound OVA molecules, streptavidin-coated superparamagnetic beads (Dynabeads with a diameter of 2.8 µm, Invitrogen) was incubated with biotinylated OVA for 1 hour at 4° C. with rotation after preparative washing steps. The loading of OVA onto the microbeads was confirmed by measuring protein concentration (absorbance at 280 nm) of supernatant before and after incubation with microbeads, and the surface density was calculated accordingly. For a model peptide epitope, N-terminal biotinylated OVA 323-339 (biotin-ISQAVHAAHAEINEAGR (SEQ ID NO: 1)) was purchased from AnaSpec and used without further purification. For pOVA tetramer formation, 1 volume of 100 µM pOVA stock solution in DMSO was slowly added into 4 volume of 2 µM PE-streptavidin (eBioscience) or non-conjugated streptavidin (Pierce) in PBS and incubated for 2 hours at 4° C. with rotation, which was followed by repeated purification by filtration (Amicon Ultra, MWCO 10k, EMD Millipore). For staining of pOVA-specific population, 3~10 nM of pOVA-tetramer was used per $10^6$ cells. For detection and sorting of NP-specific B cells, $NP_5$—BSA-Biotin (Biosearch Technologies) were directly added to B cell suspensions at 1~10 µg ml$^{-1}$ per $10^6$ cells. Following 20 min incubation at 4° C., cells were washed 3 times before subsequently incubated with PE-conjugated streptavidin for 30 min at 4° C. Upon washing, the B cells were analyzed.

RT-PCR Analysis.

RNA from each sorted B cell population was prepared with RNeasy kit (Qiagen). The cDNA was prepared by using SuperScript III First-Strand Synthesis kit and Oligo(dT)$_{20}$ (Invitrogen). Quantitative real-time PCR was performed using RT$^2$ SYBR® Green qPCR Mastermix (Qiagen) and a Step One Plus Real-Time PCR System (Applied Biosystems). Gene expression was normalized to that of β-actin (ACT), and a fold difference of the normalized values relative to that of follicular B cells are reported (2 to the power of –ΔΔCT). All the gene-specific primers for AICDA, BCL6, PRDM1, and β-actin were purchased from Qiagen and used without further purification steps.

Elispot Assays.

OVA-specific antibody secreting cells (ASCs) generated by sGC cell cultures were detected and quantified by ELISPOT assay on a 96-well MultiScreenHTS-IP filter plate (Millipore). The plate was coated with 10 µg ml$^{-1}$ OVA for overnight at 4° C. The cells harvested from sGC culture were washed twice before a defined number of cells were added to each well in triplicate for at least three orders of serial dilution with complete RPMI-1640 cell culture media as described above. After overnight incubation in a humidified atmosphere at 37° C. with 5% $CO_2$, anti-OVA IgM and anti-OVA IgG1 spots were detected by AP-conjugated goat anti-mouse IgM and IgG1 antibodies (Southern Biotech) in conjunction with Vector Blue AP substrate (Vector Laboratories). The image of wells were acquired using CTL-ImmunoSpot plate reader (Cellular Technology Limited).

Immunization for Generation of NP-Specific Natural Germinal Center B Cells.

8~12 week old mice were immunized with 100 µg of $NP_{45}$-CGG mixed with Alum (2% Alhydrogel®, Brenntag Biosector) intraperitoneally. 2 weeks after vaccination, NP+, CD19+, CD43–, GL7+, Fas+ physiological GC B cells were isolated from the spleen via FACS.

Next Generation Sequencing.

The pOVA- or NP-positive B cells were sorted by FACS upon 6-day sGC cultures. The total RNA from each sample was purified using RNeasy kit (Qiagen). From the RNA, cDNA was synthesized using random hexamers and Superscript III or AccuScript High Fidelity reverse transcriptase (Agilent Technologies) for sequencing experiment for pOVA- and NP-specific B cells, respectively. From the cDNA, mouse Ig heavy chain V region gene transcripts were amplified by two rounds of semi-nested PCR. The PCR reaction scheme and the basic primer designs were adapted from the previous literature[61] and slightly modified. The adapted primers originally designed by examining published Ig gene segment nucleotide sequences from the IGMT®, the international ImMunoGeneTics information system (www.imgt.org) and NCBI (www.ncbi.nlm.nih.gov/igblast/) databases were modified with the 454 Sequencing adaptor sequences and multiplex identifiers (MIDs) (Table 1). All PCR reactions were performed in a total reaction volume of 50 µl per reaction containing 4 µl of cDNA from the previous RT-PCR as template, 200 nM each primer, 300 µM each dNTP (Invitrogen) and 1.5 U HotStar Taq DNA polymerase (Qiagen) or Q5 Hot Start High-Fidelity DNA polymerase (New England Biolabs) for pOVA- and NP-specific B cells, respectively. The first round of PCR was performed at 94° C. for 15 min followed by 50 cycles of 94° C. for 30 seconds, 56° C. for 30 seconds, 72° C. for 55 seconds, and final incubation at 72° C. for 10 minutes. Semi-nested second round PCR was performed with 4 μl of unpurified first round PCR product with the same reaction mixture at 94° C. for 15 minute followed by 50 cycles of 94° C. for 30 seconds, 60° C. for 30 seconds, 72° C. for 45 seconds, and final incubation at 72° C. for 10 minutes. The resulting PCR products were analyzed on 2% agarose gels, which clearly showed DNA bands corresponding to heavy chain genes with IgGs and IgM isotype. The DNA were purified from the cutout bands using Gel Extraction Kit (Qiagen). The next-generation sequencing was performed using 454 Sequencing System (Roche). All analyses for the resulting sequences were performed using IMGT/highV-Quest. The sequences showing V region identity of less than 90%, fewer than 200 base pairs, or unproductive protein translations were excluded from the analyses. Ig lineage trees were produced using IgTree software[62], information for which can be found at immsilico2.lnx.biu.ac.il/Software.html. Clones were identified by their CDR3 sequences and aligned with the germline variable sequence as identified by IGMT/highV-Quest.

suspended in 200 ul of physiological saline per mouse were injected into mice via tail vein. For the short-term syngeneic or the long-term congenic transfer experiments, sGC B cells derived from C57BL6/J or C57BL6-CD45.1 mice were transferred into C57BL6/J mice (CD45.2+) with or without the non-lethal irradiation (6.5 Gy), respectively. 4 days or 4 weeks after injections, B cells isolated from pooled lymph nodes (inguinal, axillary, and brachial) and the spleen of the recipient mice and control mice were analyzed by flow cytometry and immunofluorescence microscopy.

Immunofluorescence Microscopy.

The inguinal lymph nodes harvested from the recipient mice embedded in O.C.T. compound (Sakura) were frozen in liquid nitrogen and kept at −80° C. Frozen sections (7 μm thick) were fixed in cold acetone for 1 min. After washing 3 times with PBS, the sections were incubated with a blocking buffer (eBioscience) for 2 hours at room temperature. The sections were stained with 5 μg ml-1 anti-CD4-eFluor570 (eBioscience) and anti-CD45R-APC (eBiosci-

TABLE 1

The list of primer designs employed for two rounds of semi-nested PCR for amplification of mouse Ig heavy chain V region gene transcripts. For the 2$^{nd}$ round of PCR, adaptor sequences used in 454 Sequencing System ($^a$) and multiplex identifiers ($^b$) were added onto the template specific primer sequences ($^c$).

| 1$^{st}$ PCR | Primer Name | Primer Sequence (5' to 3') | | | |
|---|---|---|---|---|---|
| | 5' MsVHE | GGGAATTCGAGGTGCAGCTGCAGGAGTCTGG (SEQ ID NO: 3) | | | |
| | 3' Cμ outer | AGGGGGCTCTCGCAGGAGACGAGG (SEQ ID NO: 4) | | | |
| | 3' Cγ1 outer | | | | |

| 2$^{nd}$ PCR | Primer Name | 454 Adaptor$^a$ | MID$^b$ | Template Specific Primer$^c$ | Modification |
|---|---|---|---|---|---|
| | 5' MsVHE-1 | CGTATCGCCT CCCTCGCGCCATCAG (SEQ ID NO: 6) | ACGAGTGCGT (SEQ ID NO: 8) | GGGAATTCGAGG TGCAGCTGCAGG AGTCTGG (SEQ ID NO: 3) | |
| | 5' MsVHE-2 | CGTATCGCCT CCCTCGCGCCATCAG (SEQ ID NO: 6) | ACGCTCGACA (SEQ ID NO: 9) | GGGAATTCGAGG TGCAGCTGCAGG AGTCTGG (SEQ ID NO: 3) | |
| | 3' Cμ inner-1 | CTATGCGCCT TGCCAGCCCGCTCAG (SEQ ID NO: 7) | ACGAGTGCGT (SEQ ID NO: 8) | AGGGGGAAGAC ATTTGGCAAGGAC (SEQ ID NO: 10) | 5' biotinylation |
| | 3' Cμ inner-2 | CTATGCGCCT TGCCAGCCCGCTCAG (SEQ ID NO: 7) | ACGCTCGACA (SEQ ID NO: 9) | AGGGGGAAGAC ATTTGGCAAGGAC (SEQ ID NO: 10) | 5' biotinylation |
| | 3' Cγ1 inner-1 | CTATGCGCCT TGCCAGCCCGCTCAG (SEQ ID NO: 7) | ACGAGTGCGT (SEQ ID NO: 8) | GCTCAGGGAAAT AGCCCTTGAC (SEQ ID NO: 11) | 5' biotinylation |
| | 3' Cγ1 inner-2 | CTATGCGCCT TGCCAGCCCGCTCAG (SEQ ID NO: 7) | ACGCTCGACA (SEQ ID NO: 9) | GCTCAGGGAAAT AGCCCTTGAC (SEQ ID NO: 11) | 5' biotinylation |

Adoptive Transfer.

sGC B cells were derived by sGC_44 cultures for 5~6 days. For a short-term tracking of the transferred syngeneic B cells, the sGC cells were loaded with CFSE (Molecular Probes) by incubation in 5 μM CFSE for 15 min at room temperature followed by washing and incubation in complete RPMI-1640 medium for 10 min at room temperature. The microbeads and dead cells were sequentially depleted from the cell suspension using a magnetic precipitation (DynaMag, Invitrogen) and negative MACS sorting by Dead Cell Removal Kit (Miltenyi) applied on LS column (Miltenyi), respectively. Approximately 1×10$^7$ purified cells ence) in TBS with 1% BSA for 4 hours at 4° C. After 3 times of rinsing with 5 minute gentle agitation in TBS containing 0.025% Triton-X and 3 times of final washing with TBS, the sections were mounted with ProLong Gold antifade medium (Molecular Probes). All the samples were examined using Zeiss LSM 700 confocal microscope (Zeiss).

Statistical Analysis.

The Student's t-test was performed for verification of statistical significance. For multiple group comparison, ordinary one-way ANOVA analyses followed by Tukey's test were performed using GraphPad Prism software.

SEQUENCE LISTING

| SEQ ID NO: | Type | Source | Sequence |
|---|---|---|---|
| 1 | Protein | Synthetic | ISQAVHAAHAEINEAGR |
| 2 | Protein | Synthetic | YPYDVPDYA |
| 3 | DNA | Synthetic | GGGAATTCGAGGTGCAGCTGCAGGAGTCTGG |
| 4 | DNA | Synthetic | AGGGGGCTCTCGCAGGAGACGAGG |
| 5 | DNA | Synthetic | GGAAGGTGTGCACACCGCTGGAC |
| 6 | DNA | Synthetic | CGTATCGCCTCCCTCGCGCCATCAG |
| 7 | DNA | Synthetic | CTATGCGCCTTGCCAGCCCGCTCAG |
| 8 | DNA | Synthetic | ACGAGTGCGT |
| 9 | DNA | Synthetic | ACGCTCGACA |
| 10 | DNA | Synthetic | AGGGGGAAGACATTTGGGAAGGAC |
| 11 | DNA | Synthetic | GCTCAGGGAAATAGCCCTTGAC |
| 12 | DNA | Synthetic | CGTATCCCTCCCTCGCGCCATCAGACACGAGTGCGTGG GAATTCGAGGTGCAGCTGCAGGAGTCTGG |
| 13 | DNA | Synthetic | CGTATCGCCTCCCTCGCGCCATCAGACACGCTCGACAG GGAATTCGAGGTGCAGCTGCAGGAGTCTGG |
| 14 | DNA | Synthetic | CTATGCGCCTTGCCAGCCCGCTCAGACGAGTGCGTAGG GGGAAGACATTTGGGAAGGAC |
| 15 | DNA | Synthetic | CTATGCGCCTTGCCAGCCCGCTCAGACGCTCGACAAGG GGGAAGACATTTGGGAAGGAC |
| 16 | DNA | Synthetic | CTATGCGCCTTGCCAGCCCGCTCAGACGAGTGCGTGCTC AGGGAAATAGCCCTTGAC |
| 17 | DNA | Synthetic | CTATGCGCCTTGCCAGCCCGCTCAGACGCTCGACAGCTC AGGGAAATAGCCCTTGAC |
| 18 | Protein | Synthetic | IEKKIEAIEKKIEAIEKKIEAIEKKIEAGGGSGGGSGGGSMQ RGDEDPQIAAHVVSEANSNAASVLQWAKKGYYTMKSNL VMLENGKQLTVKREGLYYVYTQVTFCSNREPSSQRPFIVG LWLKPSSGSERILLKAANTHSSSQLCEQQSVHLGGVFELQ AGASVFVNVTEASQVIHRVGFSSFGLLKL |
| 19 | Protein | Synthetic | YPYDVPDYAIEKKIEAIEKKIEAIEKKIEAIEKKIEAGGGSG GGSGGGSMQRGDEDPQIAAHVVSEANSNAASVLQWAKK GYYTMKSNLVMLENGKQLTVKREGLYYVYTQVTFCSNR EPSSQRPFIVGLWLKPSSGSERILLKAANTHSSSQLCEQQSV HLGGVFELQAGASVFVNVTEASQVIHRVGFSSFGLLKL |

REFERENCES

1 Banchereau, J., Depaoli, P., Valle, A., Garcia, E. & Rousset, F. Long-Term Human B-Cell Lines Dependent on Interleukin-4 and Antibody to Cd40. *Science* 251, 70-72, doi:DOI 10.1126/science.1702555 (1991).

2 Hollenbaugh, D. et al. The human T cell antigen gp39, a member of the TNF gene family, is a ligand for the CD40 receptor: expression of a soluble form of gp39 with B cell co-stimulatory activity. *The EMBO journal* 11, 4313-4321 (1992).

3 Spriggs, M. K. et al. Recombinant human CD40 ligand stimulates B cell proliferation and immunoglobulin E secretion. *The Journal of experimental medicine* 176, 1543-1550 (1992).

4 Mazzei, G. J. et al. Recombinant soluble trimeric CD40 ligand is biologically active. *The Journal of biological chemistry* 270, 7025-7028 (1995).

5 Cocks, B. G., Malefyt, R. D., Galizzi, J. P., Devries, J. E. & Aversa, G. Il-13 Induces Proliferation and Differentiation of Human B-Cells Activated by the Cd40-Ligand. *International immunology* 5, 657-663, doi:DOI 10.1093/intimm/5.6.657 (1993).

6 Arpin, C. et al. Generation of Memory B-Cells and Plasma-Cells in-Vitro. *Science* 268, 720-722, doi:DOI 10.1126/science.7537388 (1995).

7 Nojima, T. et al. In-vitro derived germinal centre B cells differentially generate memory B or plasma cells in vivo. *Nature communications* 2, 465, doi:10.1038/ncomms1475 (2011).

8 Moutai, T., Yamana, H., Nojima, T. & Kitamura, D. A novel and effective cancer immunotherapy mouse model using antigen-specific B cells selected in vitro. *PloS one* 9, e92732, doi:10.1371/journal.pone.0092732 (2014).

9 Purwada, A. et al. Ex vivo engineered immune organoids for controlled germinal center reactions. *Biomaterials* 63, 24-34, doi:10.1016/j.biomaterials.2015.06.002 (2015).

10 Zhang, Y. et al. Germinal center B cells govern their own fate via antibody feedback. *The Journal of experimental medicine* 210, 457-464, doi:10.1084/jem.20120150 (2013).

11 Anderson, S. M. et al. Taking advantage: high-affinity B cells in the germinal center have lower death rates, but similar rates of division, compared to low-affinity cells. *Journal of immunology* 183, 7314-7325, doi:10.4049/jimmunol.0902452 (2009).

12 Khalil, A. M., Cambier, J. C. & Shlomchik, M. J. B Cell Receptor Signal Transduction in the GC Is Short-Circuited by High Phosphatase Activity. *Science* 336, 1178-1181, doi:10.1126/science.1213368 (2012).

13 Kalled, S. L. Impact of the BAFF/BR3 axis on B cell survival, germinal center maintenance and antibody production. *Semin Immunol* 18, 290-296, doi:10.1016/j.smim.2006.06.002 (2006).

14 Muramatsu, M. et al. Class switch recombination and hypermutation require activation-induced cytidine deaminase (AID), a potential RNA editing enzyme. *Cell* 102, 553-563 (2000).

15 Revy, P. et al. Activation-induced cytidine deaminase (AID) deficiency causes the autosomal recessive form of the Hyper-IgM syndrome (HIGM2). *Cell* 102, 565-575 (2000).

16 Peled, J. U. et al. The biochemistry of somatic hypermutation. *Annu Rev Immunol* 26, 481-511, doi:10.1146/annurev.immunol.26.021607.090236 (2008).

17 Ye, B. H. et al. The BCL-6 proto-oncogene controls germinal-centre formation and Th2-type inflammation. *Nat Genet* 16, 161-170, doi:10.1038/ng0697-161 (1997).

18 Dent, A. L., Shaffer, A. L., Yu, X., Allman, D. & Staudt, L. M. Control of inflammation, cytokine expression, and germinal center formation by BCL-6. *Science* 276, 589-592 (1997).

19 Basso, K. et al. Tracking CD40 signaling during germinal center development. *Blood* 104, 4088-4096, doi:10.1182/blood-2003-12-4291 (2004).

20 Basso, K. & Dalla-Favera, R. BCL6: master regulator of the germinal center reaction and key oncogene in B cell lymphomagenesis. *Adv Immunol* 105, 193-210, doi: 10.1016/S0065-2776(10)05007-8 (2010).

21 Ding, B. B., Bi, E., Chen, H., Yu, J. J. & Ye, B. H. IL-21 and CD40L synergistically promote plasma cell differentiation through upregulation of Blimp-1 in human B cells. *Journal of immunology* 190, 1827-1836, doi:10.4049/jimmunol.1201678 (2013).

22 Shapiro-Shelef, M. et al. Blimp-1 is required for the formation of immunoglobulin secreting plasma cells and pre-plasma memory B cells. *Immunity* 19, 607-620 (2003).

23 Angelin-Duclos, C., Cattoretti, G., Lin, K. I. & Calame, K. Commitment of B lymphocytes to a plasma cell fate is associated with Blimp-1 expression in vivo. *Journal of immunology* 165, 5462-5471 (2000).

24 Tew, J. G., Kosco, M. H., Burton, G. F. & Szakal, A. K. Follicular dendritic cells as accessory cells. *Immunological reviews* 117, 185-211 (1990).

25 Klaus, G. G., Humphrey, J. H., Kunkl, A. & Dongworth, D. W. The follicular dendritic cell: its role in antigen presentation in the generation of immunological memory. *Immunological reviews* 53, 3-28 (1980).

26 Batista, F. D., Iber, D. & Neuberger, M. S. B cells acquire antigen from target cells after synapse formation. *Nature* 411, 489-494, doi:10.1038/35078099 (2001).

27 Kepler, T. B. & Perelson, A. S. Cyclic Reentry of Germinal Center B-Cells and the Efficiency of Affinity Maturation. *Immunol Today* 14, 412-415, doi:Doi 10.1016/0167-5699(93)90145-B (1993).

28 Berek, C., Berger, A. & Apel, M. Maturation of the Immune-Response in Germinal-Centers. *Cell* 67, 1121-1129, doi:Doi 10.1016/0092-8674(91)90289-B (1991).

29 Jacob, J., Kelsoe, G., Rajewsky, K. & Weiss, U. Intraclonal Generation of Antibody Mutants in Germinal-Centers. *Nature* 354, 389-392, doi:Doi 10.1038/354389a0 (1991).

30 Di Noia, J. M. & Neuberger, M. S. Molecular mechanisms of antibody somatic hypermutation. *Annu Rev Biochem* 76, 1-22, doi: 10.1146/annurev.biochem.76.061705.090740 (2007).

31 Dorner, T. et al. Delineation of selective influences shaping the mutated expressed human Ig heavy chain repertoire. *Journal of immunology* 160, 2831-2841 (1998).

32 Dadgostar, H. et al. Cooperation of multiple signaling pathways in CD40-regulated gene expression in B lymphocytes. *Proceedings of the National Academy of Sciences of the United States of America* 99, 1497-1502, doi:10.1073/pnas.032665099 (2002).

33 Elgueta, R. et al. Molecular mechanism and function of CD40/CD40L engagement in the immune system. *Immunological reviews* 229, 152-172, doi:10.1111/j.1600-065X.2009.00782.x (2009).

34 Pype, S. et al. TTRAP, a novel protein that associates with CD40, tumor necrosis factor (TNF) receptor-75 and TNF receptor-associated factors (TRAFs), and that inhibits nuclear factor-kappa B activation. *The Journal of biological chemistry* 275, 18586-18593, doi:10.1074/jbc.M000531200 (2000).

35 Brown, K. D., Hostager, B. S. & Bishop, G. A. Differential signaling and tumor necrosis factor receptor-associated factor (TRAF) degradation mediated by CD40 and the Epstein-Barr virus oncoprotein latent membrane protein 1 (LMP1). *The Journal of experimental medicine* 193, 943-954 (2001).

36 Armitage, R. J. et al. Molecular and biological characterization of a murine ligand for CD40. *Nature* 357, 80-82, doi:10.1038/357080a0 (1992).

37 Grassme, H., Bock, J., Kun, J. & Gulbins, E. Clustering of CD40 ligand is required to form a functional contact with CD40. *The Journal of biological chemistry* 277, 30289-30299, doi:10.1074/jbc.M200494200 (2002).

38 Graf, D. et al. A soluble form of TRAP (CD40 ligand) is rapidly released after T cell activation. *European journal of immunology* 25, 1749-1754, doi:10.1002/eji.1830250639 (1995).

39 McHeyzer-Williams, M., Okitsu, S., Wang, N. & McHeyzer-Williams, L. Molecular programming of B cell memory. *Nat Rev Immunol* 12, 24-34, doi:10.1038/nri3128 (2012).

40 Bardelli, M. et al. Ex vivo analysis of human memory B lymphocytes specific for A and B influenza hemagglutinin by polychromatic flow-cytometry. *PloS one* 8, e70620, doi:10.1371/journal.pone.0070620 (2013).

41 Franz, B., May, K. F., Jr., Dranoff, G. & Wucherpfennig, K. Ex vivo characterization and isolation of rare memory B cells with antigen tetramers. *Blood* 118, 348-357, doi:10.1182/blood-2011-03-341917 (2011).

42 Moody, M. A. & Haynes, B. F. Antigen-specific B cell detection reagents: use and quality control. *Cytometry A* 73, 1086-1092, doi:10.1002/cyto.a.20599 (2008).

43 Newman, J., Rice, J. S., Wang, C., Harris, S. L. & Diamond, B. Identification of an antigen-specific B cell population. *J Immunol Methods* 272, 177-187 (2003).

44 Kodituwakku, A. P., Jessup, C., Zola, H. & Roberton, D. M. Isolation of antigen-specific B cells. *Immunol Cell Biol* 81, 163-170, doi:10.1046/j.1440-1711.2003.01152.x (2003).

45 Wilker, P. R. et al. Transcription factor Mef2c is required for B cell proliferation and survival after antigen receptor stimulation. *Nature immunology* 9, 603-612, doi:10.1038/ni.1609 (2008).

46 Kurosaki, T., Shinohara, H. & Baba, Y. B cell signaling and fate decision. *Annu Rev Immunol* 28, 21-55, doi: 10.1146/annurev.immunol.021908.132541 (2010).

47 Batista, F. D. & Neuberger, M. S. Affinity dependence of the B cell response to antigen: a threshold, a ceiling, and the importance of off-rate. *Immunity* 8, 751-759 (1998).

48 Berek, C., Berger, A. & Apel, M. Maturation of the immune response in germinal centers. *Cell* 67, 1121-1129 (1991).

49 Jacob, J., Kelsoe, G., Rajewsky, K. & Weiss, U. Intraclonal generation of antibody mutants in germinal centres. *Nature* 354, 389-392, doi:10.1038/354389a0 (1991).

50 Klein, U. & Dalla-Favera, R. Germinal centres: role in B-cell physiology and malignancy. *Nat Rev Immunol* 8, 22-33, doi:10.1038/nri2217 (2008).

51 Denepoux, S. et al. Induction of somatic mutation in a human B cell line in vitro. *Immunity* 6, 35-46 (1997).

52 Kallberg, E., Jainandunsing, S., Gray, D. & Leanderson, T. Somatic mutation of immunoglobulin V genes in vitro. *Science* 271, 1285-1289 (1996).

53 Schultze, J. L. et al. CD40-activated human B cells: an alternative source of highly efficient antigen presenting cells to generate autologous antigen-specific T cells for adoptive immunotherapy. *The Journal of clinical investigation* 100, 2757-2765, doi:10.1172/JC1119822 (1997).

54 Wennhold, K., Shimabukuro-Vornhagen, A., Theurich, S. & von Bergwelt-Baildon, M. CD40-activated B cells as antigen-presenting cells: the final sprint toward clinical application. *Expert review of vaccines* 12, 631-637, doi: 10.1586/erv.13.39 (2013).

55 Li, Q. et al. Adoptive transfer of tumor reactive B cells confers host T-cell immunity and tumor regression. *Clinical cancer research: an official journal of the American Association for Cancer Research* 17, 4987-4995, doi: 10.1158/1078-0432.CCR-11-0207 (2011).

56 Namm, J. P. et al. B lymphocytes as effector cells in the immunotherapy of cancer. *Journal of surgical oncology* 105, 431-435, doi:10.1002/jso.22093 (2012).

57 Klenovsek, K. et al. Protection from CMV infection in immunodeficient hosts by adoptive transfer of memory B cells. *Blood* 110, 3472-3479, doi:10.1182/blood-2007-06-095414 (2007).

58 de Wit, J. et al. Antigen-specific B cells reactivate an effective cytotoxic T cell response against phagocytosed *Salmonella* through cross-presentation. *PloS one* 5, e13016, doi:10.1371/journal.pone.0013016 (2010).

59 Tiller, T., Busse, C. E. & Wardemann, H. Cloning and expression of murine Ig genes from single B cells. *J Immunol Methods* 350, 183-193, doi:10.1016/j.jim.2009.08.009 (2009).

60 Barak, M., Zuckerman, N. S., Edelman, H., Unger, R. & Mehr, R. IgTree: creating Immunoglobulin variable region gene lineage trees. *J Immunol Methods* 338, 67-74, doi:10.1016/j.jim.2008.06.006 (2008).

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

All patents, applications, publications, test methods, literature, and other materials cited herein are hereby incorporated by reference in their entirety as if physically present in this specification.

What is claimed is:

1. A method of ex vivo generation of B cells in a synthetic germinal center comprising:

exposing naïve B cells to a protein comprising the amino acid sequence of SEQ ID NO: 18 and to an antigen in the synthetic germinal center, wherein at least one of the protein or the antigen is presented on a three dimensional surface; and obtaining B cells with one or more characteristics selected from the group consisting of efficient B cell proliferation, class switching recombination (CSR), expression of activated B cell phenotypes, expression of germinal center B cell phenotypes, expression of plasma cell phenotypes, expression of memory B cell phenotypes, expression of regulatory B cell phenotypes, antibody secretion, and somatic hypermutation (SHM) and resulting affinity maturation.

2. A method of ex vivo generation of B cells in a synthetic germinal center comprising:

exposing naïve B cells to a protein comprising the amino acid sequence of SEQ ID NO: 18 and to an antigen selected from the group consisting of polypeptides and proteins, at least one kind of the protein comprising the amino acid sequence of SEQ ID NO: 18 or the antigen is in a soluble form;

eliminating at least a portion of dead B cells; and obtaining antigen-specific B cells with one or more characteristics selected from the group consisting of efficient B cell proliferation, class switching recombination (CSR), expression of activated B cell phenotypes, expression of memory B cell phenotypes, expression of regulatory B cell phenotypes, expression of plasma cell phenotypes, antibody secretion, and somatic hypermutation (SHM) and resulting affinity maturation.

3. The method of claim 1, wherein exposing the naïve B cells comprises exposing the naïve B cells isolated from a primary source to the protein and to the antigen; and wherein at least one of the protein and the antigen are present in multivalent form.

4. The method of claim 1 further comprising sorting the naïve B cells prior to exposure to the antigen.

5. The method of claim 1, wherein the three dimensional surface comprises a microbead or a microcarrier.

6. The method of claim 1, wherein during the exposing, soluble factors are added to the synthetic germinal center.

7. The method of claim 6, wherein the soluble factors are selected from the group consisting of cytokines, B cell growth factors, B cell activation factors, and toll-like receptor ligands.

8. The method of claim 7, wherein the cytokines are selected from the group consisting of IL-2, IL-4, IL-5, IL-10, and IL-21.

9. The method of claim 2, wherein eliminating at least a portion of dead B cells comprises one or more of centrifugation, fluorescence-activated cell sorting (FACS), magnetic-activated cell sorting (MACS), enzymatic degradation, filtration, microfluidic cell sorting, and size exclusion chromatography.

10. The method of claim 1, wherein obtaining the B cells comprises obtaining antigen-specific B cells; and
wherein the method further comprises purifying the antigen-specific B cells.

11. The method of claim 10, wherein purifying the antigen-specific B cells comprises one or more of fluorescence-activated cell sorting (FACS), magnetic-activated cell sorting (MACS), centrifugation, microfluidic cell sorting, and size exclusion chromatography.

12. A method of ex vivo generation of B cells comprising:
exposing naïve B cells to a protein comprising the amino acid sequence of SEQ ID NO: 18 and to an antigen, wherein at least one of the protein or the antigen is presented on a three dimensional surface of a microbead or a microcarrier; and
obtaining B cells with one or more characteristics selected from the group consisting of efficient B cell expansion, efficient B cell proliferation, class switching recombination (CSR), expression of activated B cell phenotypes, expression of germinal center B cell phenotypes, expression of plasma cell phenotypes, expression of memory B cell phenotypes, expression of regulatory B cell phenotypes, antibody secretion, and somatic hypermutation (SHM) and resulting affinity maturation.

13. The method of claim 1 further comprising classifying the naïve B cells prior to exposure to the antigen;
wherein the antigen is selected from the group consisting of polypeptides and proteins.

14. The method of claim 2 further comprising purifying the naïve B cells prior to exposure to the antigen.

15. The method of claim 1 further comprising, in between the exposing and the obtaining, eliminating at least a portion of three dimensional surface by one or more of centrifugation, degradation, dissolution, filtration, sorting, and size exclusion chromatography.

16. The method of claim 1, wherein the three dimensional surface is a three dimensional surface of an artificial/synthetic structure.

17. The method of claim 1, wherein the antigen is presented on the three dimensional surface; and
wherein the three dimensional surface is not a three dimensional surface of a naturally occurring structure or a three dimensional surface of a genetically modified biological cell.

18. The method of claim 5, wherein exposing the naïve B cells comprises exposing the naïve B cells isolated from a primary source to the protein and to the antigen; and
wherein at least one of the protein and the antigen is bound to the microbead or microcarrier.

* * * * *